(12) United States Patent
Olson et al.

(10) Patent No.: US 6,962,798 B2
(45) Date of Patent: Nov. 8, 2005

(54) METHODS AND COMPOSITIONS RELATING TO A CARDIAC-SPECIFIC NUCLEAR REGULATORY FACTOR

(75) Inventors: Eric N. Olson, Dallas, TX (US); Da-Zhi Wang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 79 days.

(21) Appl. No.: 10/029,217

(22) Filed: Dec. 21, 2001

(65) Prior Publication Data

US 2002/0164735 A1 Nov. 7, 2002

Related U.S. Application Data

(60) Provisional application No. 60/257,761, filed on Dec. 21, 2000.

(51) Int. Cl.[7] .......................... C12P 21/02; C12N 15/63; C12N 1/21; C12N 1/19; C07H 21/04
(52) U.S. Cl. .............. 435/69.1; 435/252.3; 435/254.11; 435/320.1; 435/325; 536/23.5
(58) Field of Search .............................. 435/69.1, 252.3, 435/254.11, 320.1, 325; 536/23.5

(56) References Cited

U.S. PATENT DOCUMENTS

| | | | |
|---|---|---|---|
| 5,792,453 A | 8/1998 | Hammond et al. | 424/93.21 |
| 6,100,242 A | 8/2000 | Hammond et al. | 514/44 |
| 6,569,662 B1 * | 5/2003 | Tang et al. | 435/212 |

OTHER PUBLICATIONS

GenBank Accession No. AQ028029.*
Edmonson et al., "Mef2 gene expression marks the cardiac and skeletal muscle lineages during mouse embryogenesis," *Development*, 120:1251–1263, 1994.
GenBank Accession No. AC005358.
GenBank Accession No. AI607474.
GenBank Accession No. AW500597.
GenBank Accession No. BE311634.
Hammond et al., "Adenoviral based in–vivo gene transfer in the pig," *Clin. Res.*, 42:123A, 1994.
Harvey, "Nk–2 homeobox genes and heart development," *Dev. Biol.*, 178:203–216, 1996.
Kodama, et al., "Leukemia inhibitory factor, a potent cardiac hypertrophic cytokine, activates the JAK/STAT pathway in rat cardiomyocytes," *Cir. Res.* 81:656–663, 1997.

Leor et al., "Transplantation of fetal myocardial tissue into the infarcated myocardium of rat," *Circulation*, 94(Suppl. II):II–332–II–336, 1996.
Lin et al., "Control of mouse cardiac morphogenesis and myogenesis by transcription factor MEF2C," *Science*, 276:1404–1407, 1997.
Makino et al., "Cardiomyocytes can be generated from marrow stromal cells in vitro," *J. Clin. Invest.*, 103:697–105, 1999.
Molkentin, "Cooperative activation of muscle gene expression by MEF2 and myogenic bHLH proteins," *Cell*, 83:1125–1136, 1995.
Pan, et al., "Role of angiotensin II in activation of the JAK/STAT pathway induced by acute pressure overload in the rat heart," *Circ. Res.*, 81:611–617, 1997.
Srivastava et al., "A subclass of bHLH proteins required for cardiac morphogenesis," *Science*, 270:1995–1999, 1995.
Aravind and Koonin, "SAP—a putative DNA–binding motif involved in chromosomal organization," *TIBS*, 25:112–114, 2000.
Belaguli et al., "Cardiac tissue enriched factors serum response factor and GATA-4 are mutual coregulators," *Mol. Cell. Biol.*, 20:7550–7558, 2000.
EMBL Database Accession No. AF384055.
EMBL Database Accession No. AF532596.
Treisman, "Ternary complex factors: growth factor regulated transcriptional activators," *Curr. Opinion in Genetics and Development*, 4:96–101, 1994.
Wang et al., "Activation of cardiac gene expression by myocardin, a transcriptional cofactor for serum response factor," *Cell*, 105:851–562, 2001.
Wang et al., "Potentiation of serum response factor activity by a family of myocardin–related transcription factors," *Proc. Natl. Acad. Sci., USA*, 99:14855–14860, 2002.

* cited by examiner

*Primary Examiner*—Robert A. Wax
(74) *Attorney, Agent, or Firm*—Fulbright & Jaworski, LLP

(57) ABSTRACT

The present invention relates to a novel cardiac-specific transcription factor, myocardin. This molecule modulates the development and differentiation of cardiomyocytes and is a potent inhibitor of cell growth. Methods to exploit these observations are provided and include respecifiying non-cardiac cells into cardiac cells, stimulating cardiac tissue regeneration, and methods for treating cardiomyopathies, myocardial infarction.

28 Claims, 17 Drawing Sheets

Cardi-Act1

```
GGAATTCGGCACGAGGCCACCCTCAGAGGA GGAGGGTCCTGCCTGCTGGGAGTTAATTAG 60
CCTTAAGCCGTGCTCCGGTGGGAGTCTCCT CCTCCCAGGACGGACGACCCTCAATTAATC

CCTCGCGAGCGGCGAGGGGGGAGGCGCCAG TTTTCTGGGGACACTGGCGGCCACTGTGCG 120
GGAGCGCTCGCCGCTCCCCCCTCCGCGGTC AAAAGACCCCTGTGACCGCCGGTGACACGC

TCCTCCTACCCAAGGGAGCTCCCCAAGAGT TGGATGAATTCTGGGTTGTTAGCTGCTGTC 180
AGGAGGATGGGTTCCCTCGAGGGGTTCTCA ACCTACTTAAGACCCAACAATCGACGACAG

CTCTGGGCTCCCGGGAGCCAGTTTCTGGTG GAAAGCGGGGCGCCTGGCCAACGACCAGCG 240
GAGACCCGAGGGCCCTCGGTCAAAGACCAC CTTTCGCCCCGCGGACCGGTTGCTGGTCGC

GCTTGCTGAGACTCACCATGACACTCCTGG GGTCTGAACACTCTTTGCTGATTAGAAGGA 300
CGAACGACTCTGAGTGGTACTGTGAGGACC CCAGACTTGTGAGAAACGACTAATCTTCCT

AGTTCCGATCAGTCTTACAGTTACGGCTTC AACAGAGAAGGACCCAGGAGCAGCTGGCTA 360
TCAAGGCTAGTCAGAATGTCAATGCCGAAG TTGTCTCTTCCTGGGTCCTCGTCGACCGAT

ACCAAGGCTTAATACCGCCACTGAAAGGTC CAACTGAATTCCATGACCCGAGAAAACAAT 420
TGGTTCCGAATTATGGCGGTGACTTTCCAG GTTGACTTAAGGTACTGGGCTCTTTTGTTA

TGGATAGTGCCAAGACTGAAGATTCCCTGA GGCGCAAGGGCAGAAACAGGTCCGACCGTG 480
ACCTATCACGGTTCTGACTTCTAAGGGACT CCGCGTTCCCGTCTTTGTCCAGGCTGGCAC

CCAGCCTGGTTACTATGCACATTCTCCAAG CCTCCACGGCAGAAAGGTCCATTCCAACTG 540
GGTCGGACCAATGATACGTGTAAGAGGTTC GGAGGTGCCGTCTTTCCAGGTAAGGTTGAC

CTCAGATGAAGCTCAAAAGAGCCCGCCTTG CAGATGACCTCAATGAGAAGATCGCTCTCC 600
GAGTCTACTTCGAGTTTTCTCGGGCGGAAC GTCTACTGGAGTTACTCTTCTAGCGAGAGG

GCCAAGGCCCTTGGAACTGGTGGAGAAGAA CATTCTGCCGATGGATTCTTCCGTGAAAGA 660
CGGTTCCGGGAACCTTGACCACCTCTTCTT GTAAGACGGCTACCTAAGAAGGCACTTTCT
                                M  D  S  S  V  K  E
GGCTATAAAAGGTACTGAGGTGAGCCTCTC CAAGGCAGCAGATGCATTCGCCTTTGAGGA 720
CCGATATTTTCCATGACTCCACTCGGAGAG GTTCCGTCGTCTACGTAAGCGGAAACTCCT
 A  I  K  G  T  E  V  S  L  S  K  A  A  D  A  F  A  F  E  D

TGACAGCAGTAGAGATGGGCTCTCTCCAGA TCAGGCTAGGAGCGAGGACCCCCAGGGCTC 780
ACTGTCGTCATCTCTACCCGAGAGAGGTCT AGTCCGATCCTCGCTCCTGGGGGTCCCGAG
 D  S  S  R  D  G  L  S  P  D  Q  A  R  S  E  D  P  Q  G  S

TACAGGATCCACCCCAGACATCAAATCCAC TGAGGCTCCTCTGGACACAATCCAGGATCT 840
ATGTCCTAGGTGGGGTCTGTAGTTTAGGTG ACTCCGAGGAGACCTGTGTTAGGTCCTAGA
 T  G  S  T  P  D  I  K  S  T  E  A  P  L  D  T  I  Q  D  L

CACTCCTGGCTCAGAAAGTGACAAGAATGA TGCAGCCTCCCAGCCAGGCAACCAGTCAGA 900
GTGAGGACCGAGTCTTTCACTGTTCTTACT ACGTCGGAGGGTCGGTCCGTTGGTCAGTCT
 T  P  G  S  E  S  D  K  N  D  A  A  S  Q  P  G  N  Q  S  D

CCCTGGGAAGCAGGTTCTCGGCCCCCTCAG CACCCCGATTCCTGTGCACACTGCTGTAAA 960
GGGACCCTTCGTCCAAGAGCCGGGGGAGTC GTGGGGCTAAGGACACGTGTGACGACATTT
 P  G  K  Q  V  L  G  P  L  S  T  P  I  P  V  H  T  A  V  K

GTCCAAGTCTTTGGGTGACAGTAAGAACCG CCACAAAAAGCCCAAAGACCCCAAACCAA 1020
CAGGTTCAGAAACCCACTGTCATTCTTGGC GGTGTTTTTCGGGTTTCTGGGGTTTGGTTT
 S  K  S  L  G  D  S  K  N  R  H  K  K  P  K  D  P  K  P  K

GGTGAAGAAGCTCAAATACCATCAGTACAT CCCCCCAGACCAGAAGGCAGAGAAGTCTCC 1080
CCACTTCTTCGAGTTTATGGTAGTCATGTA GGGGGGTCTGGTCTTCCGTCTCTTCAGAGG
 V  K  K  L  K  Y  H  Q  Y  I  P  P  D  Q  K  A  E  K  S  P

CCCACCCATGGACTCTGCCTATGCCCGGCT GCTCCAGCAACAGCAGCTATTCCTGCAGCT 1140
GGGTGGGTACCTGAGACGGATACGGGCCGA CGAGGTCGTTGTCGTCGATAAGGACGTCGA
 P  P  M  D  S  A  Y  A  R  L  L  Q  Q  Q  Q  L  F  L  Q  L

ACAGATCCTCAGCCAGCAGCAGCAACAGCA GCAGCAACAGCAGCAGCAACAGCAGCA 1200
TGTCTAGGAGTCGGTCGTCGTCGTTGTCGT CGTCGTTGTCGTCGTCGTCGTTGTCGTCGT
```

FIG. 2

```
         Q  I  L  S  Q  Q  Q  Q  Q  Q    Q  Q  Q  Q  Q  Q  Q  Q  Q  Q
      GCAGCAGCAGCAGCAGCGGTTCAGCTACCC  TGGGATGCACCAAACACACCTCAAAGAACC  1260
      CGTCGTCGTCGTCGTCGCCAAGTCGATGGG  ACCCTACGTGGTTTGTGTGGAGTTTCTTGG
        Q  Q  Q  Q  Q  R  F  S  Y  P     G  M  H  Q  T  H  L  K  E  P

AAATGAACAGATGGCCAGAAATCCGAATCC  TTCTTCAACACCACTGAGCAATACCCCTCT  1320
      TTTACTTGTCTACCGGTCTTTAGGCTTAGG  AAGAAGTTGTGGTGACTCGTTATGGGGAGA
        N  E  Q  M  A  R  N  P  N  P     S  S  T  P  L  S  N  T  P  L

ATCCCCTGTCAAAAATAGCATTTCTGGACA  AACTGGTGTTTCTTCTCAAACCAGGCCC  1380
      TAGGGGACAGTTTTTATCGTAAAGACCTGT  TTGACCACAAAGAAGAGAGTTTGGTCCGGG
        S  P  V  K  N  S  I  S  G  Q     T  G  V  S  S  L  K  P  G  P

CCTCCCACCCAACCTGGATGATCTCAAGGT  GTCAGAGTTAAGACAACAGCTTCGAATCCG  1440
      GGAGGGTGGGTTGGACCTACTAGAGTTCCA  CAGTCTCAATTCTGTTGTCGAAGCTTAGGC
        L  P  P  N  L  D  D  L  K  V     S  E  L  R  Q  Q  L  R  I  R

GGGCTTGCCAGTGTCAGGCACCAAGACAGC  GCTGGTGGACCGGCTTCGTCCCTTCCAGGA  1500
      CCCGAACGGTCACAGTCCGTGGTTCTGTCG  CGACCACCTGGCCGAAGCAGGGAAGGTCCT
        G  L  P  V  S  G  T  K  T  A     L  V  D  R  L  R  P  F  Q  D

TTGTGCTGGCAACCCTGTGCCCAACTTTGG  GGACATCACAACTGTCACCTTTCCTGTCAC  1560
      AACACGACCGTTGGGACACGGGTTGAAACC  CCTGTAGTGTTGACAGTGGAAAGGACAGTG
        C  A  G  N  P  V  P  N  F  G     D  I  T  T  V  T  F  P  V  T

GCCCAACACCTTGCCCAGTTATCAGTCCTC  CCCGACAGGCTTCTACCACTTTGGCAGCAC  1620
      CGGGTTGTGGAACGGGTCAATAGTCAGGAG  GGGCTGTCCGAAGATGGTGAAACCGTCGTG
        P  N  T  L  P  S  Y  Q  S  S     P  T  G  F  Y  H  F  G  S  T

AAGCTCCAGCCCACCCATCTCCCCCGCCTC  ATCTGACTTGTCCGCTGCAGGGTCCCTGCC  1680
      TTCGAGGTCGGGTGGGTAGAGGGGGCGGAG  TAGACTGAACAGGCGACGTCCCAGGGACGG
        S  S  S  P  P  I  S  P  A  S     S  D  L  S  A  A  G  S  L  P

AGACACCTTCACCGATGCGTCACCTGGCTT  CGGCCTGCACGCATCTCCGGTGCCCGCCTG  1740
      TCTGTGGAAGTGGCTACGCAGTGGACCGAA  GCCGGACGTGCGTAGAGGCCACGGGCGGAC
        D  T  F  T  D  A  S  P  G  F     G  L  H  A  S  P  V  P  A  C

CACGGACGAGAGTCTGCTGAGCAGCCTGAA  TGGGGGCTCGGGCCCCTCCGAGCCTGATGG  1800
      GTGCCTGCTCTCAGACGACTCGTCGGACTT  ACCCCCGAGCCCGGGGAGGCTCGGACTACC
        T  D  E  S  L  L  S  S  L  N     G  G  S  G  P  S  E  P  D  G

GCTAGACTCTGAGAAGGACAAGATGCTGGT  GGAGAAGCAGAAAGTGATCAACCAGCTCAC  1860
      CGATCTGAGACTCTTCCTGTTCTACGACCA  CCTCTTCGTCTTTCACTAGTTGGTCGAGTG
        L  D  S  E  K  D  K  M  L  V     E  K  Q  K  V  I  N  Q  L  T

CTGGAAGCTGCGGCAAGAGCAGCGGCAGGT  GGAAGAGCTGAGAATGCAACTGCAGAAGCA  1920
      GACCTTCGACGCCGTTCTCGTCGCCGTCCA  CCTTCTCGACTCTTACGTTGACGTCTTCGT
        W  K  L  R  Q  E  Q  R  Q  V     E  E  L  R  M  Q  L  Q  K  Q

GAAGAGCAGCTGCAGCGACCAGAAGCCACT  GCCCTTCTTGGCCACCACCATCAAACAGGA  1980
      CTTCTCGTCGACGTCGCTGGTCTTCGGTGA  CGGGAAGAACCGGTGGTGGTAGTTTGTCCT
        K  S  S  C  S  D  Q  K  P  L     P  F  L  A  T  T  I  K  Q  E

AGATGTCTCCAGCTGCCCCTTCGCACCCCA  GCAGGCGTCTGGGAAGGGACAGGGCCACAG  2040
      TCTACAGAGGTCGACGGGGAAGCGTGGGGT  CGTCCGCAGACCCTTCCCTGTCCCGGTGTC
        D  V  S  S  C  P  F  A  P  Q     Q  A  S  G  K  G  Q  G  H  S

CTCTGACAGTCCCCCTCCGGCTTGTGAGAC  GGCTCAGCTGCTGCCTCACTGTGTGGAGTC  2100
      GAGACTGTCAGGGGGAGGCCGAACACTCTG  CCGAGTCGACGACGGAGTGACACACCTCAG
        S  D  S  P  P  P  A  C  E  T     A  Q  L  L  P  H  C  V  E  S

CTCAGGTCAAACCCATGTACTCTCGTCCAC  GTTTCTCAGCCCCCAGTGCTCCCCTCAGCA  2160
      GAGTCCAGTTTGGGTACATGAGAGCAGGTG  CAAAGAGTCGGGGTCACGAGGGGAGTCGT
        S  G  Q  T  H  V  L  S  S  T     F  L  S  P  Q  C  S  P  Q  H

CTCGCCCCTGGGGGGCCTGAAGAGCCCGCA  GCACATCAGCCTGCCTCCATCACCCAACAA  2220
      GAGCGGGGACCCCCCGGACTTCTCGGGCGT  CGTGTAGTCGGACGGAGGTAGTGGGTTGTT
        S  P  L  G  G  L  K  S  P  Q     H  I  S  L  P  P  S  P  N  N

CCATTACTTCCTGGCTTCCTCTTCGGGAGC  TCAGAGAGAGAACCATGGGGTCTCTTCACC  2280
```

FIG. 2 CONT.

```
GGTAATGAAGGACCGAAGGAGAAGCCCTCG AGTCTCTCTCTTGGTACCCCAGAGAAGTGG
  H  Y  F  L  A  S  S  S  G  A   Q  R  E  N  H  G  V  S  S  P

CAGCAGCAGCCAAGGGTGCGCACAGATGAC TGGTTTACAATCTTCTGACAAGGTGGGGCC 2340
GTCGTCGTCGGTTCCCACGCGTGTCTACTG ACCAAATGTTAGAAGACTGTTCCACCCCGG
  S  S  S  Q  G  C  A  Q  M  T    G  L  Q  S  S  D  K  V  G  P

AACGTTTTCAATTCCATCCCCAACTTTTTC TAAGTCAAGTTCAGCAGTTTCAGATATCAC 2400
TTGCAAAAGTTAAGGTAGGGGTTGAAAAAG ATTCAGTTCAAGTCGTCAAAGTCTATAGTG
  T  F  S  I  P  S  P  T  F  S   K  S  S  A  V  S  D  I  T

CCAGCCCCCATCCTATGAAGATGCAGTGAA GCAGCAAATGACTCGGAGTCAGCAGATGGA 2460
GGTCGGGGGTAGGATACTTCTACGTCACTT CGTCGTTTACTGAGCCTCAGTCGTCTACCT
  Q  P  P  S  Y  E  D  A  V  K   Q  Q  M  T  R  S  Q  Q  M  D

CGAACTCCTGGATGTCCTCATTGAAAGTGG AGAAATGCCAGCCGATGCCAGGGAAGATCA 2520
GCTTGAGGACCTACAGGAGTAACTTTCACC TCTTTACGGTCGGCTACGGTCCCTTCTAGT
  E  L  L  D  V  L  I  E  S  G   E  M  P  A  D  A  R  E  D  H

TTCATGTCTTCAGAAAATTCCAAAGATCCC TGGGTCCTCCTGCAGCCCAACTGCCATCCC 2580
AAGTACAGAAGTCTTTTAAGGTTTCTAGGG ACCCAGGAGGACGTCGGGTTGACGGTAGGG
  S  C  L  Q  K  I  P  K  I  P   G  S  S  C  S  P  T  A  I  P

CCCGAAGCCCTCGGCTTCCTTTGAGCAGGC ATCTTCGGGAGGCCAGATGGCCTTCGGTCA 2640
GGGCTTCGGGAGCCGAAGGAAACTCGTCCG TAGAAGCCCTCCGGTCTACCGGAAGCCAGT
  P  K  P  S  A  S  F  E  Q  A   S  S  G  G  Q  M  A  F  G  H

CTACGCCAACGACAGTGACGAACACCTGGA AGTCTTATTGAATTCTCACAGCCCCATCGG 2700
GATGCGGTTGCTGTCACTGCTTGTGGACCT TCAGAATAACTTAAGAGTGTCGGGGTAGCC
  Y  A  N  D  S  D  E  H  L  E   V  L  L  N  S  H  S  P  I  G

AAAGGTGAGCGATGTTACCCTCCTCAAAAT CGGAAGCGAGGAGCCTCCTTTTGACAGCAT 2760
TTTCCACTCGCTACAATGGGAGGAGTTTTA GCCTTCGCTCCTCGGAGGAAAACTGTCGTA
  K  V  S  D  V  T  L  L  K  I   G  S  E  E  P  P  F  D  S  I

CATGGATGGCTTCCCAGGGAAGGCTGCGGA AGATCTCTTCAGTGCTCACGAGCTCTTGCC 2820
GTACCTACCGAAGGGTCCCTTCCGACGCCT TCTAGAGAAGTCACGAGTGCTCGAGAACGG
  M  D  G  F  P  G  K  A  A  E   D  L  F  S  A  H  E  L  L  P

TGGGCCCCTCTCCCCGATGCATGCACAGTT GTCACCTCCTTCTGTGGACAGCAGTGGTCT 2880
ACCCGGGGAGAGGGGCTACGTACGTGTCAA CAGTGGAGGAAGACACCTGTCGTCACCAGA
  G  P  L  S  P  M  H  A  Q  L   S  P  P  S  V  D  S  S  G  L

GCAGCTGAGCTTCACGGAATCTCCTTGGGA AACAATGGAATGGCTGGACCTCACTCCACC 2940
CGTCGACTCGAAGTGCCTTAGAGGAACCCT TTGTTACCTTACCGACCTGGAGTGAGGTGG
  Q  L  S  F  T  E  S  P  W  E   T  M  E  W  L  D  L  T  P  P

TAGTTCCACGCCAGGCTTCAGCAACCTTAC CTCCAGTGGGCCCAGCATTTTCAACATCGA 3000
ATCAAGGTGCGGTCCGAAGTCGTTGGAATG GAGGTCACCCGGGTCGTAAAAGTTGTAGCT
  S  S  T  P  G  F  S  N  L  T   S  S  G  P  S  I  F  N  I  D

TTTTCTGGATGTTACAGATCTTAATCTGAA TTCCCCTATGGATCTCCACTTACAGCAGTG 3060
AAAAGACCTACAATGTCTAGAATTAGACTT AAGGGGATACCTAGAGGTGAATGTCGTCAC
  F  L  D  V  T  D  L  N  L  N   S  P  M  D  L  H  L  Q  Q  W

GTAAACACCCGAGGTACAAGAGCTACGAGA GCTCAGTGGGAATTCAATGGAGGAAAGCAC 3120
CATTTGTGGGCTCCATGTTCTCGATGCTCT CGAGTCACCCTTAAGTTACCTCCTTTCGTG
  *

GATACCGAAATGTGTGTTCCAAAAGATGA AGGGGGGAAAATGGGGAGGGAAAAAAAAAA 3180
CTATGGCCTTTACACACAAGGTTTTCTACT TCCCCCCTTTTACCCCTCCCTTTTTTTTTT

ACAGCAACGGAGGTTTTTGTGACAACTAAC CAGAACAAACAGAAGTCAGCTATTAAAATA 3240
TGTCGTTGCCTCCAAAAACACTGTTGATTG GTCTTGTTTGTCTTCAGTCGATAATTTTAT

TGTCTAAATGTAATATCTACCAGCATTCAG TAACTGTTAATAACTTCAGTGATGCATTCA 3300
ACAGATTTACATTATAGATGGTCGTAAGTC ATTGACAATTATTGAAGTCACTACGTAAGT

AAAATGTGCTTTGTCAGAATAAGAATGCCA AAAATGTTTTTTCGCTGCCTTATCTCATAC 3360
TTTTACACGAAACAGTCTTATTCTTACGGT TTTTACAAAAAAGCGACGGAATAGAGTATG
```

FIG. 2 CONT.

```
CAGTTTTTTTGGGTTTTTTTTTGTTTGTTT GTTTTTTGGTTTTTTTTTTTTGTGTGTGT 3420
GTCAAAAAAACCCAAAAAAAAACAAACAAA CAAAAAACCAAAAAAAAAAAAACACACACA

TGTTATTTGGTTTTCTTTTTGCCCACAGTT TGTCTCAGGCAATACTGGGACATAGGCTGA 3480
ACAATAAACCAAAAGAAAAACGGGTGTCAA ACAGAGTCCGTTATGACCCTGTATCCGACT

CCCCATTAGCTTTTGTTATGAATTTACTAA ACTTTCTGTGGAAGGAGAACAGAGCCTCTG 3540
GGGGTAATCGAAAACAATACTTAAATGATT TGAAAGACACCTTCCTCTTGTCTCGGAGAC

CCGCGGGTGTGGGAAGCCATCCTGTGCTT GAGGCAGCACACGTGTGTCCATCATCATCA 3600
GGCGCCCACACCCCTTCGGTAGGACACGAA CTCCGTCGTGTGCACACAGGTAGTAGTAGT

GTCAGAAGAGCAGGGCCTGTCTCACCCAAT CGAGTCCTTAAGACAGAATAATCAGAATGG 3660
CAGTCTTCTCGTCCCGGACAGAGTGGGTTA GCTCAGGAATTCTGTCTTATTAGTCTTACC

TCAGAGGGACAGACCAATCAATTCCCAGGA AAGCAAAAGTGACTCAATGTCCCTTGACTC 3720
AGTCTCCCTGTCTGGTTAGTTAAGGGTCCT TTCGTTTTCACTGAGTTACAGGGAACTGAG

CCAAATGGTCCCACTGGACTGGTGATCACT GGTGACAACTAACTAGCTTTGTCCAGAGAA 3780
GGTTTACCAGGGTGACCTGACCACTAGTGA CCACTGTTGATTGATCGAAACAGGTCTCTT

TCCACCCAGAACACGGTGCTTTTTAGCCAG TAGTCCACCTCTATGTGCATCAGCAATGCA 3840
AGGTGGGTCTTGTGCCACGAAAAATCGGTC ATCAGGTGGAGATACACGTAGTCGTTACGT

TAGCAGGTGAGAACTTGAATCACAGAAACT TCATGCCATGGATGGAGACTCCTGAGGCGC 3900
ATCGTCCACTCTTGAACTTAGTGTCTTTGA AGTACGGTACCTACCTCTGAGGACTCCGCG

TCAAATACTACTACCTCTAGTTCCAAAGAC TAGAGCTAGATGATCAGAAAGGCAACTGGA 3960
AGTTTATGATGATGGAGATCAAGGTTTCTG ATCTCGATCTACTAGTCTTTCCGTTGACCT

GGCCCAGGGAGCCGTACTGGGACAAGTTAG AATTAGAGAACGATGTCATTTAACATTCCG 4020
CCGGGTCCCTCGGCATGACCCTGTTCAATC TTAATCTCTTGCTACAGTAAATTGTAAGGC

AGAAAGAAATAACCATGAATTGCTATTACA GGAGTAACACACAGGGCCAGCTTCTTTTTT 4080
TCTTTCTTTATTGGTACTTAACGATAATGT CCTCATTGTGTGTCCCGGTCGAAGAAAAAA

CTTCTTTTTATTTTTCTTTTCTTATTGTG AGCAGAGGGAATTCACCTCAGTTCATCTTT 4140
GAAGAAAAATAAAAAGAAAAGAATAACAC TCGTCTCCCTTAAGTGGAGTCAAGTAGAAA

CTCTCAGTACTTTTCTTTCAAGATATCAAT CCTTTATGACTCTTTTGCTTTTAATTCTCT 4200
GAGAGTCATGAAAAGAAAGTTCTATAGTTA GGAAATACTGAGAAAACGAAAATTAAGAGA

CTCTCTCTCTCTCTCTCTCTCTCTCTCTTT CTCTCAAAGGAGAGGTTTCAGTTCTAACAA 4260
GAGAGAGAGAGAGAGAGAGAGAGAGAGAAA GAGAGTTTCCTCTCCAAAGTCAAGATTGTT

GCTACCATAGTCCTATTAAAGCCATTTTTT TTTTTAGAATATTAAAAGTCCAAACTCTCT 4320
CGATGGTATCAGGATAATTTCGGTAAAAAA AAAAATCTTATAATTTTCAGGTTTGAGAGA

TGCCAAACTCTTTCTTCACATGCGCATTGG CTGAAAACAGAATTTACAAGAATTTCTTTA 4380
ACGGTTTGAGAAAGAAGTGTACGCGTAACC GACTTTTGTCTTAAATGTTCTTAAAGAAAT

GGAAGAAACTGGGGATGTGGCCCATTGGTC ACAAAGTTTTTTGTTTGTTTTTGTTTTTG 4440
CCTTCTTTGACCCCTACACCGGGTAACCAG TGTTTCAAAAAAACAAACAAAAACAAAAAC

TTTCAATTCTTGTTTGATTTATGGACAATC TTTGGTTTGTATTGCTCTCGAGAAATTGCA 4500
AAAGTTAAGAACAAACTAAATACCTGTTAG AAACCAAACATAACGAGACCTCTTTAACCT

AATCATTGCAGAGTGAAGATAAATCAGGGC ACCATGTATAGTAGAGAATGTTTCAGTAGT 4560
TTAGTAACGTCTCACTTCTATTTAGTCCCG TGGTACATATCATCTCTTACAAAGTCATCA

TTTCCAAACGAGAACACAATTGCACACTGT AAACAACAGGAGTGTGAAGGACCACAGTCT 4620
AAAGGTTTGCTCTTGTGTTAACGTGTGACA TTTGTTGTCCTCACACTTCCTGGTGTCAGA

TGAGGAGTTCTTGTTGCCCTGTGTTTGGTG AAGGCGTTGGGGACCGAGGAAGACAACATA 4680
ACTCCTCAAGAACAACGGGACACAAACCAC TTCCGCAACCCCTGGCTCCTTCTGTTGTAT

CAGTTTGGCCAAGGCTCTCAGAGGCTTGCT GTGGCGCCAATTCAAGTATTACAATGTTGC 4740
GTCAAACCGGTTCCGAGAGTCTCCGAACGA CACCGCGGTTAAGTTCATAATGTTACAACG

ATGCTGTAGAAAGTAGCTGTTGCTGTTGTT TTGTTTTGTTTTAATTTAAGTCACCAAGGC 4800
TACGACATCTTTCATCGACAACGACAACAA AACAAAACAAAATTAAATTCAGTGGTTCCG
```

FIG 2 CONT.

```
ACTGTTTTATTCTTTTGTAAAAAAAAAAAA AGTTCACTGTGCACTTATAGAGAAAATAAT 4860
TGACAAAATAAGAAAACATTTTTTTTTTT  TCAAGTGACACGTGAATATCTCTTTTATTA

CAACAATGTTGTGAATTTTTGAGAAGACTT TTTTTTTTTTGATAAACCAAAGATTTAGAA 4920
GTTGTTACAACACTTAAAAACTCTTCTGAA AAAAAAAAAACTATTTGGTTTCTAAATCTT

ATCATTCCATTGTCAACTTGTAAAAAAAAA AAAAAAAAA
TAGTAAGGTAACAGTTGAACATTTTTTTTT TTTTTTTTT
```

FIG. 2 CONT.

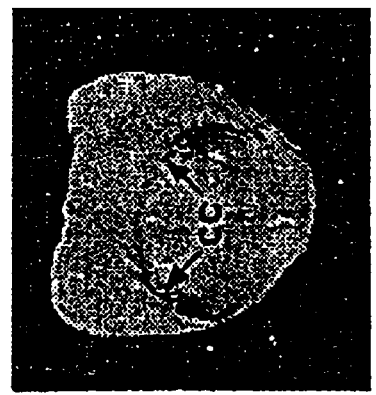
FIG. 3A-C

METHODS AND COMPOSITIONS RELATING TO A CARDIAC-SPECIFIC NUCLEAR REGULATORY FACTOR

This application claims benefit of priority to U.S. Provisional Application Ser. No. 60/257,761 filed Dec. 21, 2000.

The government owns rights in the application pursuant to NIH Grant Nos. P01 HL49953 and HL63926.

BACKGROUND OF THE INVENTION

1. Field of the Invention

The present invention relates generally to the fields of developmental biology and molecular biology. More particularly, it concerns proteins involved in the regulation of cardiomyocyte cell growth and development.

2. Description of Related Art

The leading cause of morbidity and mortality in industrialized countries is heart disease, particularly heart disease that is associated with myocardial infarction. Myocardial infarction results in the loss of cardiomyocytes. Cardiomyocytes are post-mitotic cells and generally do not regenerate after birth. Furthermore, it has been discovered that they respond to mitotic signals by cell hypertrophy (Kodama et al., 1997; Pan et al., 1997) rather than by cell hyperplasia. The loss of cardiomyocytes leads to regional contractile dysfunction. In addition, the necrotized cardiomyocytes in the infarcted regions in the ventricular tissues are progressively replaced by fibroblasts to form scar tissue.

Recently, fetal cardiomyocytes transplanted in heart scar tissue limited scar expansion and prevented postinfarction heart failure (Leor et al., 1996). Although the transplantation of fetal cardiomyocytes is a proposed treatment of heart failure, it remains impractical in the clinical setting, in part because of the difficulty of obtaining fetal heart donor tissue. Thus, it is desirable to develop a cardiomyogenic cell line that could be used to facilitate the understanding of cardiomyocyte development and to facilitate the treatment of heart diseases, such as those associated with loss of cardiomyocytes.

Although it is known that the loss of post-mitotic cardiomyocytes results in increased morbidity and mortality, very little is known about the genes that are involved in heart development. It is known that transcription factors such as d-HAND, e-HAND (Srivastava et al., 1995), MEF-2C (Edmondson et al. 1994; Lin et al. 1997), Nkx2.5/Csx, GATA4, and TEF-1 play important roles in cardiac development (Harvey, 1996), but the lack of a model for cardiomyocyte differentiation has hindered the understanding of the interactions of these genes.

A recent report revealed that murine marrow stromal cells that are treated with 5-azacyidine, a cytosine analog capable of altering expression of certain genes that may regulate differentiation, results in a cell line that differentiates into cardiomyocytes in vitro (Makino et al., 1999). This cardiomyogenic cell line demonstrated several phenotypic characteristics that are specific to cardiomyocytes, e.g., adjoining cells via intercalated discs, forming myotubes, and beating spontaneously. In addition, the expression of cardiomyocyte specific genes, such as homeobox gene Nkx2.5, alpha-myosin heavy chain and atrial natriuretic factor, also are considered characteristic.

Although the proposed transplantation of fetal cardiomyocytes and cardiomyogenic cell lines are possible treatments, it is preferable to discover a treatment that eliminates any donor/species problems. Thus, identifying new regulators of cardiomyocyte growth and differentiation is an important goal in the search for therapeutics to treat myocardial tissue damage.

SUMMARY OF THE INVENTION

The present invention provides polypeptides capable of modulating cell phenotype, particularly phenotypic characteristics of cardiomyocyte cells, and polynucleotides encoding such polypeptides. In particular, provided herein is a family of peptides, known as myocardins, that share certain sequence homology and functional activities, as described herein. In one aspect, the polypeptides of the present invention comprise mycardin peptides and biologically active fragments thereof. In another aspect, the present invention provides isolated polynucleotides encoding a myocardin peptide including fragments thereof. Exemplary biologically active fragments of myocardin polypeptides are also provided herein.

In a further aspect, there are provided expression cassettes comprising polynucleotides encoding the polypeptides of the present invention. Preferably, such expression cassettes further comprise one or more regulatory sequences operably linked to said polynucleotide, capable of enhancing or otherwise modulating transcription and/or translation of said polynucleotide in a target cell, for example a mammalian cell. By way of illustration, in one embodiment, an expression cassette comprising a polynucleotide encoding a myocardin polypeptide operably linked to a promoter is provided. The promoter may be an inducible promoter or a constitutive promoter. The promoter may be heterologous to the myocardin coding sequence. Further, the promoter may be a ubiquitous promoter, for example a cytomeglovirus (CMV) promoter, rous sarcoma virus (RSV) promoter or human elongation factor (e.g., hEF-1α) promoter, or it may be active only in certain tissues/cells for example a fibroblast specific promoter (e.g., an alpha collagen promoters) or a muscle-specific promoter (e.g., a myosin light chain-2 promoter or a α-myosin heavy chain). The regulatory sequence of the expression cassette may further comprise a polyadenylation signal. The expression cassette may be a viral expression construct, for example, a retroviral vector, an adenoviral vector, an adeno-associated viral vector, a vaccina viral vector, a herpesviral vector, a polyoma viral construct, lentiviral vector or a Sindbis viral vector. The expression cassette may further comprise a second polynucleotide encoding a second polypeptide. The second polypeptide may be, for example, a cardiac transcription factor.

In another aspect of the present invention, there is provided an isolated nucleic acid segment comprising at least 15 contiguous nucleotides of SEQ ID NO: 1, SEQ ID NO: 25, SEQ ID NO: 27 or SEQ ID NO: 29. Also provided is an isolated nucleic acid segment of SEQ ID NO: 1, SEQ ID NO: 25, SEQ ID NO: 27 or SEQ ID NO: 29 comprising 15–2000 nucleotides in length. In a related aspect, there is provided a peptide of 8–50 residues comprising at least 8–12 consecutive residues of SEQ ID NO: 2, SEQ ID NO: 26, SEQ ID NO: 28 or SEQ ID NO: 30. In another related aspect, there are provided antibodies, which may be produced by a hybridoma cell, that bind immunologically to a polypeptide comprising SEQ ID NO: 2, SEQ ID NO: 26, SEQ ID NO: 28 or SEQ ID NO: 30, or an antigenic fragment thereof. The antibodies may be monoclonal or polyclonal antisera.

In a further aspect of the present invention, as described further below, myocardin peptides from different species are provided. By way of illustration, murine myocardin 1 (e.g., SEQ ID NOS: 2 and 30), human myocardin 1 (e.g. SEQ ID NOS: 26 and 28), human myocardin 2 (SEQ ID NO: 4) and human myocardin 3 (SEQ ID NO: 6) are described. These myocardin peptides share localized regions of high amino acid sequence homology, particularly in the carboxyl-terminal transcription activation domain, and, particularly with respect to myocardin 1 and 2, in glutamine (Q) rich domains.

In still a further aspect of the invention, there is provided a transformed host cell comprising a polynucleotide encoding a myocardin polypeptide and a promoter heterologous to the myocardin-encoding polynucleotide which promoter directs the expression of the myocardin polypeptide. The host cell may be prokaryotic or eukaryotic. In a related aspect of the invention, there is provided a method of using the transformed host cell and culturing it under conditions suitable for the expression of the myocardin polypeptide. In yet another aspect, there is provided a fusion protein comprising a myocardin protein or peptide fused to a second protein or peptide.

As discussed above, heart disease, especially that resulting in a heart attack, typically results in significant cardiac dysfunction. This dysfunction can be the result of the activities of cells, especially non-cardiomyocyte cells, in the region of disease of the heart. In a further aspect of the present invention, compositions and methods are provided that alleviate the deleterious activities of such non-cardiomyocyte target cells on the functioning of the heart by modulating the phenotype of said target cells. In preferred embodiments, the compositions and methods not only alleviate the deleterious activities of the target cell population but stimulate the target cells to engage in one or more functions typical of cardiomyocytes thereby improving myocardial functioning in the diseased region. By way of illustration, fibroblast cells typically are recruited to form scar tissue in areas of myocardium where cardiomyocyte necrosis has occurred (for example, as the result of myocardial infarction) thereby resulting in permanent, regional cardiac dysfunction. Introduction of a composition in accordance herewith into such fibroblasts can prevent those cells from engaging in such deleterious activity and, in preferred embodiments, can actually stimulate the fibroblasts to engage in one or more functions phenotypical of cardiomyocytes (for example, spontaneous beating, formation of microtubules or adjoining to neighboring cells via intercalated discs, and expression of cardiomyocyte specific genes, such as homeobox gene Nkx2.5, alpha-myosin heavy chain and atrial natriuretic factor) thereby assisting heart function. Advantageously, introduction of such compositions in accordance herewith may additionally improve the functioning of existing cardiomyocytes by, for example, inducing hypertrophy therein. Thus, the present compositions may serve the dual roles of stimulating fibroblast cells to engage in function(s) phenotypic of cardiomyocytes and stimulating hypertrophy in existing cardiomyocytes.

In yet a further and related aspect of the present invention, there is provided a method of converting a non-cardiomyocyte target cell, such as a cardiac fibroblast into a cardiac myocyte-like cell comprising introducing into the target cell an expression cassette. The expression cassette comprises a polynucleotide encoding a myocardin polypeptide as well as one or more regulatory sequences, for example, a promoter with or without enhancer sequences, which regulatory sequences are active in the target cell and direct the expression of the polypeptide. The method may further comprise measuring cardiac and muscle cell lineage markers. In another aspect, the expression cassette may further comprise one or more additional polynucleotides encoding one or more polypeptides. By way of illustration, a second polypeptide may be a cardiac transcription factor, for example, GATA4. In a related aspect, expression of the additional polynucleotides may be under the control of the same regulatory sequences as the first polynucleotide or may be separately controlled by additional regulatory sequences.

In another aspect of the present invention, the method further comprises introducing one or more additional expression cassettes into target cells separately from introduction of the myocardin expression cassette. By way of illustration, a second expression cassette comprising a polynucleotide encoding a second polypeptide and including a second promoter able to direct expression of the second polypeptide in the target cells may be delivered to the target cell using a separate gene delivering means from that used to introduce the myocardin expression cassette. Thus, for example, a first gene delivery vector comprising a myocardin expression cassette may be delivered simultaneously or contemporaneously with a second gene delivery vector comprising a second expression cassette. If desired, polypeptide expression may be measured, for example, by measuring transcription by RNA hybridization, RT-PCR or Western analysis.

In yet another aspect, there is provided a method of generating a cardiomyocyte comprising introducing into a cardiac fibroblast an expression cassette. The expression cassette comprising, for example, a polynucleotide encoding a myocardin polypeptide operatively linked to a promoter capable of directing expression of the polypeptide. The promoter may be heterologous to the coding sequence and may be a ubiquitous (e.g., CMV) or a specific promoter (e.g., an alpha collagen promoter). The expression cassette may be introduced into the fibroblast by any of a variety of means known to those of skill in the art. By way of illustration, lipid-based vectors (e.g., liposomes), viral vectors (e.g., retroviral vectors, vaccina viral vectors, herpesviral vectors, polyoma viral constructs, lentiviral vectors or Sindbis viral vectors), or other macromolecular complexes capable of mediating delivery of the polynucleotide to the fibroblast or other target cell, may be employed. In a further aspect the gene delivery vector may be modified, for example by means known to those of skill in the art, to target one or more specific cell types. The expression cassette may also comprise a selectable marker, e.g., an immunologic marker. The expression cassette may further comprise a second polynucleotide encoding a second polypeptide, such as the GATA4 cardiac transcription factor. Such a second polynucleotide may be under control of a second promoter or the same promoter as the first polynucleotide. Alternatively, an internal ribosomal entry site (IRES) may be employed between the two transgenes to permit expression of the second transgene.

In a further aspect of the present invention, there is provided a method of stimulating cardiac tissue regeneration comprising inhibiting the function of myocardin in a post-mitotic cardiomyocyte. Inhibiting may comprise providing antisense nucleic acid that inhibits transcription or translation of a myocardin mRNA. The antisense nucleic acid may be provided by introducing an expression cassette encoding myocardin antisense RNA.

In still another aspect, there is provided a non-human transgenic animal, e.g., a mouse, comprising an expression cassette. The expression cassette comprises a polynucleotide encoding a myocardin peptide or protein and a promoter operably linked thereto which promoter may be heterologous to the myocardin peptide or protein encoding region. The promoter may be a constitutive or an inducible promoter. The expression cassette may further comprise selectable marker(s). In a related aspect of the present invention, the non-human transgenic animal may comprise a defective germ-line myocardin allele or two defective germ-line myocardin alleles.

In a further aspect of the invention, there is provided a method of treating a heart disease, such as cardiomyopathy (for example, myocardial infarction or hypertension). The method comprises administering to an animal suffering from a heart disease an expression cassette, which may comprise a polynucleotide encoding a myocardin peptide or protein and a promoter operable in eukaryotic cells. The promoter may be a tissue-specific promoter. The expression cassette may be comprised within a viral expression vector, for example, a retroviral vector, an adenoviral vector, an adeno-associated viral vector, a vaccina viral vector, a herpesviral vector, a polyoma viral construct, a lentiviral vector or a Sindbis viral vector or within a non-viral vector, for example a lipid-based vector. In a related aspect, the method may comprise providing to an animal suffering therefrom a myocardin antisense nucleic acid.

In another related aspect, there is provided a method of alleviating one or more symptoms of a heart disease comprising inhibiting the function of myocardin in post-mitotic cardiomyocytes in the subject. Another method of alleviating one or more symptoms of a heart disease, for example in a subject with heart failure, comprises increasing the level of myocardin in fibroblasts to generate cardiomyocytes in the subject.

An additional aspect of the present invention is to provide compositions and methods for the identification of downstream target genes of myocardin polypeptides. A gene delivery vector, for example an adenoviral vector, can be employed to deliver a myocardin gene to isolated cardiomyocytes thereby permitting over-expression of the myocardin polypeptide. Differences in gene profiling between control (i.e., non-transfected) cardiomyocytes and trans-fected (i.e., myocardin-overexpressing) cardiomyocytes can then be assessed by standard methods, such as differential display and microarray (e.g., gene chip) technology. Genes that are activated by myocardin in cardiomyocytes can subsequently be evaluated as potential therapeutics, for example, using bioinformatics techniques. In yet another aspect of the present invention, there is provided a method of screening for a candidate substance for an effect on myocardin regulation of cardiomyocyte development comprising: (a) providing myocardin and GATA to a cell; (b) admixing myocardin and GATA in the presence of the candidate substance; and (c) measuring the effect of the candidate substance on the expression of a cardiac lineage marker, wherein a difference in the expression of the cardiac lineage marker, as compared to an untreated cell, indicates that the candidate substance effects myocardin regulation of cardiomyocyte development.

Exemplary cells include fibroblast and cardiomyocytes, which may be located in an animal. The modulator may increase or decrease the expression of the cardiac lineage marker. The cardiac lineage marker may be Nkx2.5. The measuring of the expression of the cardiac lineage marker may comprise RNA hybridization, RT-PCR, immunologic detection, ELISA or immunohisotchemistry, for example.

In still yet another aspect of the invention, there is provided a method of screening for a modulator of myocardin expression comprising: (a) providing a cell that expresses a myocardin polypeptide; (b) contacting the myocardin polypeptide with a candidate substance; and (c) measuring the expression of myocardin, wherein a difference in myocardin expression, indicates that the candidate substance is a modulator of myocardin expression. The modulator may be a pharmaceutical composition. The modulator may enhance or inhibit myocardin expression.

In another aspect of the invention, there is provided a method of screening a candidate substance for myocardin binding activity comprising: (a) providing a myocardin polypeptide; (b) contacting the myocardin polypeptide with the candidate substance; and (c) determining the binding of the candidate substance to the myocardin polypeptide. The assay may be performed in a cell free system, a cell or in vivo. The candidate substance may be an inhibitor or an enhancer of myocardin.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2 Amino acid and nucleotide sequence of N-terminally truncated myocardin 1. A nucleotide sequence encoding an N-terminally truncated myocardin 1 and the corresponding amino acid sequence are shown.

FIG. 3A–C Expression pattern of myocardin 1 during early heart development. FIG. 3A: Expression of myocardin 1 was determined by whole-mount to mouse embryos at E7.75. Myocardin 1 transcripts can be seen localized to the cardiac crescent. FIG. 3B: Expression of myocardin 1 was determined by section to mouse embryos at E8.0. Transcripts are present throughout the heart tube in a transverse section. FIG. 3C: Expression of myocardin 1 was determined by in situ hybridizations to mouse embryos at E12.5. Transcripts are seen throughout the developing heart in a sagittal section.

FIG. 7A: shows activity of the wild-type SM22 promoter, which is transactivated about 100-fold by myocardin 1. FIG. 7B: shows activity of the SM22 promoter with a mutation in the distal CArG box (CArG-far). This promoter is also activated by myocardin 1, but not to the same extent as the wild-type promoter. FIG. 7C: shows activity of the SM22 promoter with a mutation in the proximal CArG box (CArG-near). This promoter has lost almost all responsiveness to myocardin 1, as has the promoter with both CArG boxes mutated (FIG. 7D).

DESCRIPTION OF ILLUSTRATIVE EMBODIMENTS

Figure 1:
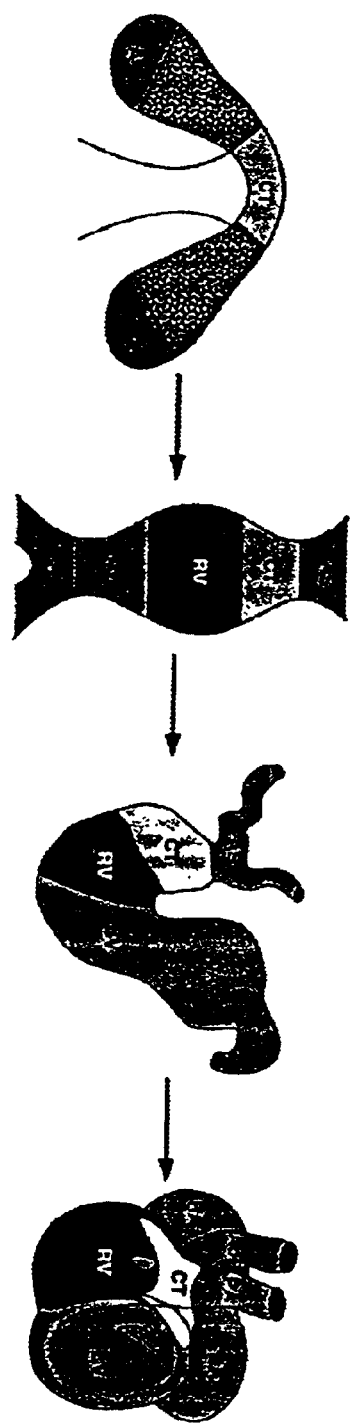
FIG. 1 Schematic diagram of the events of cardiac development. Cardiac precursors from the cardiac crescent (left) migrate to the midline of the embryo to form the linear heart tube, which undergoes rightward looping and eventual formation of the mature four-chambered heart. Different populations of cardiac precursor cells fated to form the aortic sac (AS), conotruncus (CT), right ventricle (RV), left ventricle (LV), and atria (A) are shown. A schematic diagram of the structure of the mouse myocardin 1 gene is also shown. Based on human genomic sequence in public databases, we have determined that the human gene maps to chromosome 17 and encompasses 170 kb.

Heart disease is the number one cause of death and hospitalization in the industrialized world, due in large part to the irreversible nature of the damage sustained by the heart following heart attack and other acquired and congenital diseases. At present, the only means of repairing a damaged heart is through complicated surgery and/or heart transplant, which have obvious financial and medical shortcomings for the patient. The possibility of regenerating cardiac muscle cells within the intact human heart following damage represents one of the most important challenges in cardiovascular medicine. Perhaps the greatest chance for success in this area is to identify "master" control genes for cardiac development and to use these genes to reprogram non-muscle cells to a cardiac muscle cell fate.

A major barrier to cardiac regeneration is the inability of postnatal cardiomyocytes to divide. In principle, cardiac repair could be achieved through a release from this block to cell cycle progression. However, such an approach, which might involve introduction of oncogenes or other powerful stimulators of cell proliferation into the heart, has an obvious downside unless such regulators were somehow cardiac-specific and could be prevented from inducing uncontrolled proliferation of other cell types. Because about 40% of the cells in the myocardium are fibroblasts, an alternate approach would be to reprogram these cells to a cardiomyocyte fate at sites of cardiac damage through targeted delivery of cardiac master control genes.

The loss of cardiomyocytes leads to reduced contractile function of the heart resulting in increased morbidity and mortality. The present inventors now report the discovery of novel cardiac-specific factors, referred to herein as myocardins. One such myocardin, myocardin 1, is expressed in cardiac and smooth muscle. Moreover, myocardin 1 is first expressed as early as the linear heart tube stage, embryonic day 8 (E8) in the mouse. This expression is restricted to the heart and to a subset of vascular smooth muscle cells throughout embryogenesis to adulthood. The subcellular distribution of myocardin 1 is localized in the nucleus. Moreover, expression of myocardin 1 in transfected cells appears to result in growth arrest of the cells.

To determine the functions of myocardin 1, the inventors transfected myocardin 1 expression plasmids into fibroblasts (Cos and HeLa cells) along with expression plasmids for the cardiac transcription factor GATA4. The cells were transiently transfected using FuGENE 6 (Boehringer-Mannheim), according to manufacturer's instructions. Briefly, 0.1 µg of expression plasmid encoding myocardin 1 or the other indicated cardiac transcription factors, along with the indicated luciferase plasmids, were mixed with 3 µl of FuGENE 6 and added to cells in six-well plates. Cells were harvested 48 hr later and luciferase activity was determined in cell extracts. In all transfections, the amount of DNA per well was kept constant by adding the corresponding vector. CMV-lacZ, which contains the lacZ gene under control of the constitutive cytomegalovirus promoter, was included in all transfections as an internal control to normalize for variations in transfection efficiency. The results demonstrated that myocardin 1, plus GATA4, transactivates regulatory sequences for the cardiac specific homeobox Nkx2.5, which is the earliest marker for the cardiac lineage in vertebrates. These results indicate that myocardin 1 plays an important role in regulating cardiomyocyte development.

Based upon the functional activity of the murine myocardin 1 and having its complete cDNA sequence, the inventors have been able to identify other myocardins, which they have characterized. Initial searches of DNA sequence databases with myocardin 1 sequence revealed a number of related sequences. Most of these sequences are short sequences (for example, ESTs) that share homology to only small regions of myocardin 1. None of the sequences located have been identified as encoding proteins having any particular function, much less any function related to cell regulation, particularly cardiac cell regulation. However, using these techniques in combination with the information obtained previously regarding the murine myocardin, the inventors have identified two sequences that share significant homology with myocardin 1. These appear to be partial sequences from two additional myocardin genes. cDNA clones for these two related genes, now designated myocardin 2 and myocardin 3, have been obtained. A comparison of the three myocardin species identified has revealed localized regions of high amino acid homology between the proteins, particularly in the carboxyl-terminal transcription activation domain. By Northern analysis, it was shown that that myocardin 2 is ubiquitous, and that myocardin 3 appears restricted to heart and liver. These factors may be dimerization partners for myocardin 1, and/or may serve analogous functions to myocardin 1 in the heart and/or other tissues.

Using similar techniques and information about the murine myocardin 1, the inventors have also been able locate the genomic sequence of the human homolog for myocardin 1 within a particular segment of chromosome 17 (Accession No. AC005358) and to determine the location of its exons and introns, enabling identification of the human cDNA sequence. The best EST match for myocardin 1 is Accession No. AI607474, for myocardin 2 is Accession No. BE311634, and for myocardin 3 is Accession No. AW500597.

The discovery of proteins that function to regulate cardiomyocyte growth and differentiation is important, both for advancing the basic understanding of heart development and to provide novel targets for the development of drugs and/or biotechnological methods to treat cardiac disease, for example by stimulating the growth and differentiation of cells into cardiomyocytes after a patient has suffered tissue damage as a result of cardiomyopathy. Since myocardin appears to act as an early cardiac inducing factor with the capacity to induce cardiomyocyte development, and has the potential to reprogram cardiac fibroblasts, which constitute 40% of the cell types in the heart, to a cardiomyocyte type fate, it may be used in a variety of ways to directly treat cardiac disease and to develop additional treatments for cardiac disease. Further, because myocardin also appears to induce hypertrophy in cardiomyocytes, its overexpression may provide an additional benefit in the treatment of heart disease by, for example, improving the functioning of dysfunctional or malfuctional cardiomyocytes.

I. Nucleic Acids

In one aspect, the present invention provides nucleic acid sequences encoding cardiac cell regulatory factors designated myocardins. In a further aspect the coding sequence (as well as substantial non-coding protions) of a novel, N-terminally truncated cardiac-specific factor, designated herein as myocardin 1, is provided (SEQ ID NOS1 and 25). In yet another aspect of the present invention, provided herein are nucleic acids encoding mouse and human myocardin 1, SEQ ID NOS: 29 and 27, respectively. The present invention is not limited in scope to any specific nucleic acid sequences disclosed herein as one of ordinary skill in the art could, using these nucleic acid sequences, readily identify related homologs, including, for example, homologs present in any of various species (e.g., rat, rabbit, dog, monkey, gibbon, chimp, ape, baboon, cow, pig, horse, sheep, cat and other species).

Figure 6:
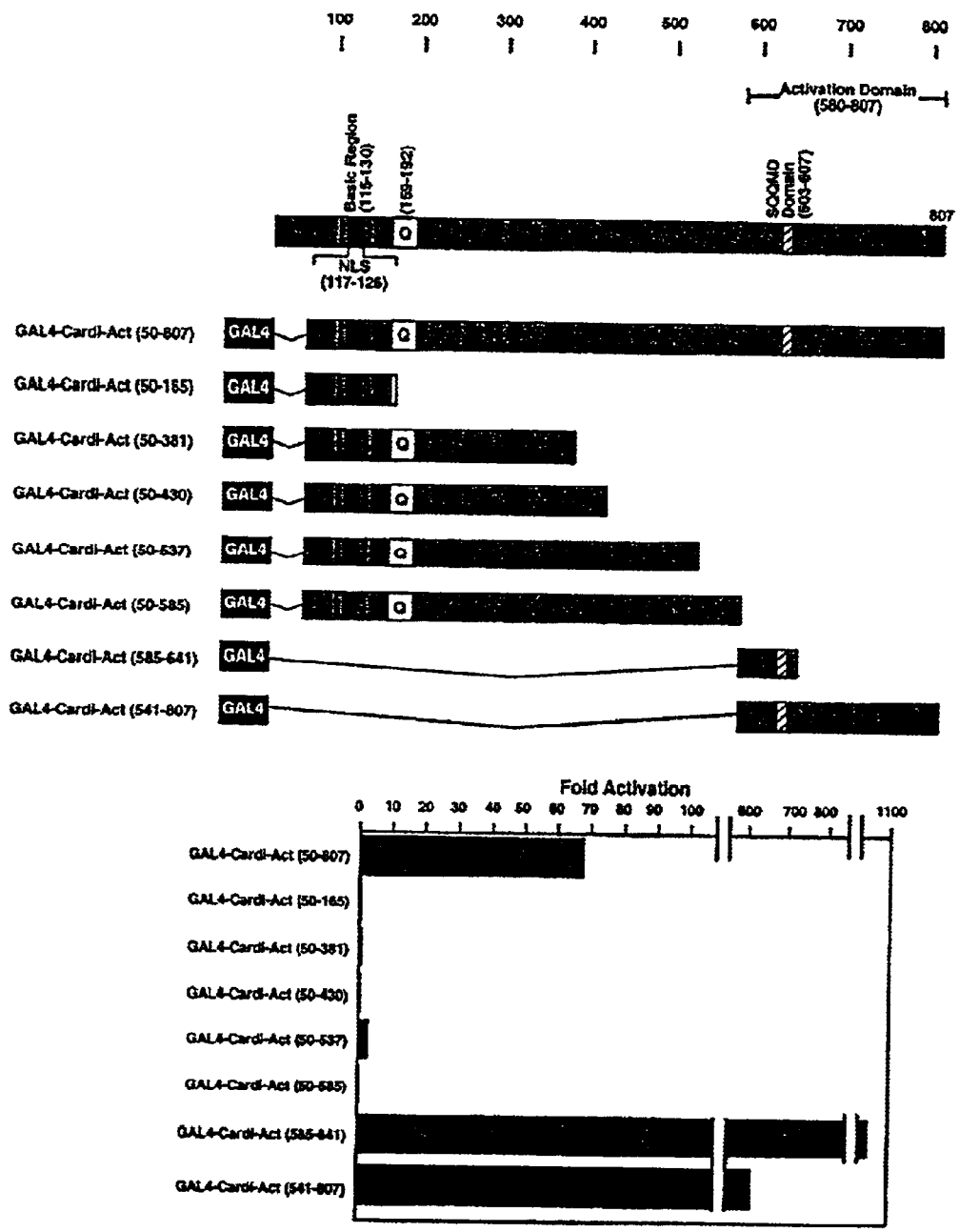
FIG. 6 Structure of myocardin 1 and mapping of transcription activation domains. A schematic diagram of myocardin 1 is shown at the top. The nuclear localization sequence (NLS) is located between residues 117 and 126, within a basic region. A glutamine-rich (Q) domain is located between residues 159–192. The transcription activation domain is located at the carboxyl-terminus. Portions of myocardin 1 were fused to the DNA binding domain of yeast GAL4 and tested in transfected Cos cells for transcriptional activity against a GAL4-dependent luciferase reporter. Relative transcriptional activities of different myocardin 1 fragments are shown at the bottom. The carboxyl-terminus is an extremely potent transcription activation domain, able to activate the reporter over 1000-fold, to a level comparable to that of the powerful viral coactivator VP16 (not shown).

As discussed below, a "myocardin nucleic acid sequence" may contain a variety of different bases and yet still produce a myocardin polypeptide according to the present invention. Such polypeptides will generally be functionally equivalent to, and/or structurally indistinguishable, from the human, mouse and other genes disclosed herein. Additionally, nucleic acid sequences encoding fragments of myocardin are provided herein. For example, fragments having increased activity (e.g., the carboxy terminal fragments described in FIG. 6) as compared with the full-length myocardin polypeptide are described. Similarly, it will be readily recognized that fragments may be employed as probes, for example in the isolation of homologous sequences. Thus, as will be apparent to those of skill in the art, fragments of the myocardin-encoding nucleic acid sequences as well as homologs thereof are likewise contemplated herein.

Similarly, any reference to a nucleic acid should be read as encompassing vectors and host cells containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of myocardin.

A. Nucleic Acids Encoding Myocardin

Nucleic acids according to the present invention may encode an entire myocardin gene, a domain of myocardin, or any other fragment of myocardin as set forth herein. The nucleic acid may be derived from genomic DNA, i.e., cloned directly from the genome of a particular organism. In preferred embodiments, however, the nucleic acid comprises complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given myocardin polynucleotide may be represented by natural or synthetic variants that have slightly different nucleic acid sequences but, nonetheless, encode the same or homologous protein (see Table 1 below).

As used in this application, the term "a polynucleotide encoding a polypeptide" refers to a nucleic acid molecule that is isolated free of total cellular nucleic acid, including for example, a synthetic polynucleotide. In exemplary embodiments, the invention concerns a nucleic acid sequence essentially as set forth in SEQ ID NO: 1, SEQ ID NO: 25, SEQ ID NO: 27 or SEQ ID NO: 29. The term "comprises SEQ ID NO: 1 or 27" means that the nucleic acid sequence substantially corresponds to a portion of the aforementioned SEQ ID NO: 1 or 27 and likewise for other SEQ ID NOS providing nucleic acid sequences. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of a sequence set forth herein, for example SEQ ID NO: 1 or 27 are contemplated. Sequences that are essentially the same as those set forth in SEQ ID NO: 1 or 27 also may be functionally defined as sequences that are capable of hybridizing to a nucleic acid segment containing the complement of SEQ ID NO: 1 or 27 under standard conditions and likewise for other nucleotide sequences set forth herein.

The DNA segments of the present invention include those encoding biologically functional equivalent myocardin proteins, peptides and fragments thereof, as described elsewhere herein. Such sequences may arise as a consequence of codon redundancy and/or amino acid functional equivalency that are known to those of skill in the art. For example, polynucleotides encoding myocardin peptides analogous to the exemplary myocardin protein of SEQ ID NO: 2 or 28 are likewise contemplated herein. As discussed further below, and as known to those of skill in the art, various amino acid substitutions, deletions and/or additions may be made to a known amino acid sequence without adversely affecting the function and/or usefulness thereof. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequences set forth herein, for example in SEQ ID NO:1. Nucleic acid sequences that are "complementary" are those that are capable of base-pairing according to the standard Watson-Crick complementary rules. As used herein, the terms "complementary sequences" and "essentially complementary sequences" means nucleic acid sequences that are substantially complementary to, as may be assessed by the same nucleotide comparison set forth above, or are able to hybridize to a nucleic acid segment of one or more sequences set forth herein, for example SEQ ID NO:1 or 27, under relatively stringent conditions such as those described herein. Such sequences may encode an entire myocardin protein or peptide or functional or non-functional fragments thereof.

The hybridizing segments may be short oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 750, 1000, 1250, 1500, 2000, 2500, 3000 or 4000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mm KCl, 3 mM MgCl$_2$, 10 mM dithiothreitol, at temperatures between approximately 20° C. to about 37° C. Other hybridization conditions utilized could include approximately 10 mM Tris-HCl (pH 8.3), 50 mM KCl, 1.5 μM MgCl$_2$, at temperatures ranging from approximately 40° C. to about 72° C. Formamide and SDS also may be used to alter the hybridization conditions.

One method of using probes and primers of the present invention is in the search for genes related to myocardin proteins and peptides, including for example, myocardin proteins from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred.

The technique typically employs a bacteriophage vector that exists in both a single stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and/or other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al, 1987; Forster and Symons, 1987). For example, a large number of ribozymes accelerate phosphoester transfer reactions with a high degree of specificity, often cleaving only one of several phosphoesters in an oligonucleotide substrate (Cook et al, 1981; Michel and Westhof, 1990; Reinhold-Hurek and Shub, 1992). This specificity has been attributed to the requirement that the substrate bind via specific base-pairing interactions to the internal guide sequence ("IGS")of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al, 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectors for Cloning, Gene Transfer and Expression

Within certain embodiments expression vectors are employed to express a myocardin polypeptide product, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, including, for example, various regulatory elements, such as enhancers/promoters from viral and/or mammalian sources that are involved in driving expression of the genes of interest in host cells. Elements designed to optimize messenger RNA stability and translatability in host cells also can be used. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" or "expression cassette" is meant to include any type of genetic construct containing a nucleic acid coding for a gene product in which part or all of the nucleic acid encoding sequence is capable of being transcribed. The transcript may be translated into a protein or polypeptide, but it need not be. In certain embodiments, expression includes both transcription of a gene and translation of mRNA into a gene product. In other embodiments, expression only includes transcription of the nucleic acid encoding a gene of interest.

As used herein, regulatory elements (or sequences) are nucleotide sequences that enhance or otherwise modulate transcription and/or translation or that stabilize transcription and/or translation products. Thus, for example, promoters operably linked to a coding sequence of an expression construct enhance transcription of that coding sequence and polyadenylation sequences operably linked to a coding sequence modulate polyadenylation of the gene transcript. Exemplary regulatory sequences can include, without limitation, promoters, enhancers, introns, termination sequences, polyadenylation sequences, stabilization sequences and the like.

In certain embodiments, the nucleic acid encoding a gene product is operably linked and under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are typically composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, the human cytomegalovirus (CMV) immediate early gene promoter, the SV40 early promoter, the Rous sarcoma virus (RSV) long terminal repeat, a human elongation factor (hEF) promoter, rat insulin promoter or glyceraldehyde-3-phosphate dehydrogenase promoter can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. By way of illustration, a ubiquitous, strong (i.e., high activity) promoter may be employed to provide abundant gene expression in a group of host cells, or a tissue-specific promoter may be employed to target gene expression to one or more specific cell types. Further, selection of a promoter that is regulated in response to specific physiologic signals can permit inducible expression of the gene product. Tables 2 and 3 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole is typically able to stimulate transcription at a distance; this need not be true of a promoter region or its component elements. On the other hand, a promoter typically has one or more elements that direct initiation of RNA synthesis at a particular site and in a particular orientation, whereas enhancers generally lack these specificities. Promoters and enhancers are often overlapping and contiguous, often seeming to have a very similar modular organization.

Tables 2 and 3, provided below, list several regulatory elements that may be employed, in the context of the present invention, to regulate the expression of the gene of interest. This list is not intended to be exhaustive of all the possible elements involved in the promotion of gene expression but, merely, to be exemplary thereof. Other promoter/enhancer combinations (see, e.g., the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Human Elongation Factor-1A (hEF-1A or hEF-1α) | Uetsuki, et al., 1989; Wakabayashi-Ito, et al., 1994 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |

TABLE 2-continued

Promoter and/or Enhancer

| Promoter/Enhancer | References |
|---|---|
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Rous sarcoma virus (RSV) | Gorman, et al., 1982; Guzman, et al., 1993 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et |

TABLE 3-continued

Inducible Elements

| Element | Inducer | References |
|---|---|---|
| β-Interferon | poly(rI)x poly(rc) | al., 1985; Sakai et al., 1988 Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

In one aspect, tissue-specific promoters, e.g., cardiac-specific and/or fibroblast-specific promoters, are of particular interest. By way of illustration, cardiac-specific promoters include the myosin light chain-2 promoter (Franz et al., 1994; Kelly et al., 1995), the alpha actin promoter (Moss et al., 1996), the troponin 1 promoter (Bhavsar et al, 1996); the $Na^+/Ca^{2+}$ exchanger promoter (Barnes et al., 1997), the dystrophin promoter (Kimura et al., 1997), the creatine kinase promoter (Ritchie, M. E., 1996), the alpha7 integrin promoter (Ziober & Kramer, 1996), the brain natriuretic peptide promoter (LaPointe et al, 1996) and the alpha B-crystallin/small heat shock protein promoter (Gopal-Srivastava, R., 1995), alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, in which cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome entry site (IRES) elements are used to create multigene, or polycistronic, messages. IRES elements is believed to allow bypassing of the ribosome scanning model of 5' methylated Cap dependent translation and facilitate translation at internal sites (Pelletier and Sonenberg, 1988). By way of illustration, IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Polyadenylation Signals

In expression, one will typically include a polyadenylation signal to effect proper polyadenylation of the transcript. The nature of the polyadenylation signal is not believed to be crucial to the successful practice of the invention, and any of a number of such sequences may be employed. Exemplary embodiments include the SV40 polyadenylation signal, the bovine growth hormone polyadenylation signal and others which are convenient and/or known to function well in various target cells. Also contemplated as an element of the expression cassette is a transcriptional termination site. These elements can serve to enhance message levels and/or to minimize read through from the cassette into other sequences.

(v) Vectors

The term "vector" is used to refer to carrier molecules with which a nucleic acid sequence can be associated for introduction into a cell. The nucleic acid sequence can be "exogenous," (e.g., foreign to the cell into which it is introduced) or "endogenous" (e.g., the same as a sequence in the cell into which it is introduced. Exemplary vectors include plasmids, cosmids, viruses (bacteriophage, animal viruses, and plant viruses), and artificial chromosomes (e.g., YACs), lipid-based vectors (e.g., liposomes) and other macromolecular complexes capable of mediating delivery of a polynucleotide to a host cell. One of skill in the art would be well equipped to construct a vector through standard techniques, for example standard recombinant techniques such as described in Sambrook et al., 1989 and Ausubel et al., 1994, both incorporated herein by reference.

A large number of viral and non-viral vectors (including lipid-based and other synthetic delivery systems known in the art) can likewise be employed to deliver polynucleotides of the present invention. Such vectors may be modified, as known to those of skill in the art, to confer or enhance cell specificity. By way of illustration, the surface of viral vectors may be modified such that they preferentially or exclusively bind to and/or infect a particular target cell population.

As used herein, the term "expression vector" refers to a vector containing a nucleic acid sequence coding for at least part of a gene product capable of being transcribed. In some cases, the transcription product(s) are then translated into a protein, polypeptide, or peptide. In other cases, these sequences are not translated, for example, in the production of antisense molecules or ribozymes. Expression vectors can contain a variety of "control sequences," which refer to nucleic acid sequences that regulate the transcription and possibly translation of an operably linked coding sequence in a particular host organism. In addition to control sequences that govern transcription and translation, vectors and expression vectors may contain nucleic acid sequences that serve other functions as well for example as described infra.

(vi) Host Cells

As used herein, the terms "cell," "cell line," and "cell culture" may be used interchangeably. These terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand conditions under which to incubate such host cells to maintain them and to permit replication of a vector. Also understood and known are techniques and conditions that would allow large-scale production of vectors, as well as production of the nucleic acids encoded by vectors and their cognate polypeptides, proteins, or peptides.

(vii) Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ baculovirus expression system from CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

(viii) Gene Delivery Means

There are a number of ways in which a gene of interest, for example within an expression vector, may be introduced into cells. In certain embodiments of the invention, the gene delivery means comprises a virus or engineered construct derived from a viral genome. The ability of certain viruses to enter cells for example via receptor-mediated endocytosis and to express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Although these viral vectors generally have a relatively fixed capacity for foreign DNA can accommodate up to 5-10 kb of foreign DNA and many different viral vectors can be readily introduced into a variety of different cells and animals (see, e.g., Nicolas and Rubenstein, 1988; Temin, 1986). Where viral vectors are employed to deliver the gene or genes of interest, it is generally preferred that they be replication-defective.

One of the preferred methods for in vivo gene delivery involves the use of an adenovirus expression vector. "Adenovirus expression vector" is meant to include those constructs containing adenovirus sequences sufficient to (a) support packaging of the construct and (b) to express polynucleotide that has been cloned therein. In this context, expression does not require that the gene product be synthesized.

An adenivorus expression vector comprises a genetically engineered form of adenovirus. Knowledge of the genetic organization of adenovirus, a linear, double-stranded DNA virus, allows substitution of large pieces of adenoviral DNA with foreign sequences (typically up to about 7 kB (Grunhaus and Horwitz, 1992)). Modified adenoviral and other viral vectors have also been constructed to provide for increased packaging capacity and are likewise contemplated herein. In contrast to retrovirus, the adenoviral infection of host cells does not generally result in chromosomal integration. Also, adenoviruses are structurally stable, and no genome rearrangement has been detected after extensive amplification. Adenovirus can infect various lineages of cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. In the case of adenovirus serotype 5 (Ad5), for example, both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is important to minimize this possibility by reducing or eliminating adnoviral sequence overlaps within the system and/or to isolate a single clone of virus from an individual plaque and examine its genomic structure.

Generation and propagation of replication-deficient adenovirus vectors depend on a unique helper cell line, such as the human 293 cell line, which was transformed from human embryonic kidney cells by Adenovirus type 5 DNA fragments to constitutively expresses E1 proteins (Graham et al., 1977). Since the E3 region is dispensable from the adenovirus genome (Jones and Shenk, 1978), the current adenovirus vectors, with the help of 293 cells, generally carry foreign DNA in either the E1, the E3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, up to about 7.5 kb of foreign DNA may be packaged in an adenovirus. Additionally, modified adenoviral vectors are now available which have an even greater capacity to carry foreign DNA.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the preference that the adenovirus vector be replication-defective, or at least conditionally defective, the nature of the adenovirus vector is not believed to be critical to the successful practice of the invention. The adenovirus may be selected from any of the 42 different known serotypes or subgroups A–F. Adenovirus serotype 5 of subgroup C is a preferred starting material for obtaining a conditional replication-defective adenovirus vector for use in the present invention. This is, in part, because Adenovirus type 5 is a human adenovirus about which a great deal of biochemical and genetic information is known, and it has historically been used for most constructions employing adenovirus as a vector. Additionally, various modifications can be made to adenovirus to facilitate cell targeting of the expression cassette and/or otherwise modify vector interaction with the host cell. By way of illustration, it is known that primary fibroblasts generally express low levels of the high-affinity Coxsackie virus and Adenovirus receptor (CAR), which receptor facilitates transduction of host cells by the adenoviral vector. However, it is also known that adenoviral vectors can be modified, for example by altering the adenovirus fiber, to improve binding to other cell-surface receptors where CAR receptors are limited (see, e.g. Hidaka et al., 1999).

As stated above, a preferred adenoviral vector according to the present invention lacks an adenovirus E1 region and thus, is replication defective. Typically, it is most convenient to introduce the polynucleotide encoding the gene of interest at the position from which the E1-coding sequences have been removed. However, the position of insertion of the construct within the adenovirus sequences is not critical to the invention. Further, other adenoviral sequences may be deleted and/or inactivated in addition to or in lieu of the E1 region. For example, the E2 and E4 regions are both necessary for adenoviral replication and thus may be modified to render an adenovirus vector replication-defective, in which case a helper cell line or helper virus complex may be employed to provide such deleted/inactivated genes in trans. The polynucleotide encoding the gene of interest may alternatively be inserted in lieu of a deleted E3 region, such as in E3 replacement vectors as described by Karlsson et al. (1986), or in the E4 region where a helper cell line or helper virus complements an E4 defect. Other modifications are known to those of skill in the art and are likewise contemplated herein.

Adenovirus is easy to grow and manipulate and exhibits broad host range in vitro and in vivo. This group of viruses can be obtained in high titers, e.g., $10^9$–$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al, 1991; Gomez-Foix et al., 1992) and vaccine development (Grunhaus and Horwitz, 1992; Graham and Prevec, 1991). Animal studies initially suggested that recombinant adenovirus could be useful for gene therapy (see, e.g., Stratford-Perricaudet and Perricaudet, 1991; Stratford-Perricaudet et al., 1990; Rich et al., 1993). Studies in administering recombinant adenovirus to different tissues include administration via intracoronary catheter into one or more coronary arteries of the heart (Hammond, et al.), U.S. Pat. Nos. 5,792,453 and 6,100,242), trachea instillation (Rosenfeld et al, 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is generally employed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al, 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al, 1989).

There are certain limitations to the use of retrovirus. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct is delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Non-viral methods for the transfer of expression constructs into mammalian cells can also be used in the context of the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention, a naked DNA expression construct may be transferred into cells using particle bombardment. This method depends on the ability to accelerate DNA-coated microprojectiles to a high velocity allowing them to pierce cell membranes and enter cells without killing them (Klein et al, 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al, 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be complexed with one or more lipid components and/or entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al, (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al, 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in most eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

II. Myocardin Peptides and Polypeptides

The present invention also provides exemplary myocardin protein/polypeptide sequences. For example, SEQ ID NOS:2, 26, 28 and 30 provide amino acid sequences for myocardins of SEQ ID NOS:1, 25, 27 and 29, respectively. In addition to entire myocardin molecules, the present invention also relates to fragments of the polypeptides that may or may not retain the various functions described below. By way of illustration, N-terminally truncated myocardin 1 polypeptides from mouse and human (SEQ ID NOS: 2 and 26, respectively) are provided, which polypeptides retain the various functions described below. Fragments, including the N-terminus of the molecule may be generated by genetic engineering of translation stop sites within the coding region (discussed below). Alternatively, treatment of the polypeptides with proteolytic enzymes, known as proteases, can produces a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural and Functional Aspects

Myocardin 1 from human and mouse, shown in SEQ ID NO:28 and SEQ ID NO:30 are 935 and 938 residues, respectively. In human myocardin 1, the nuclear localization sequence (NLS) is located between residues 245 and 254, within a basic region at residues 243–260. A glutamine-rich (Q) domain is located between residues 287–320. The SAP domain is found at residues 380–414. The transcription activation domain is located at the carboxyl-terminus at 670 to 935.

In general, myocardins are cell regulatory proteins/peptides that function to modulate cell phenotype. In particular, myocardin can be used to reduce the deleterious effects of non-cardiomyocytes on injured myocardium and/or to stimulate non-cardiomyocytes to perform one or more functions typical of cardiomyocytes, thereby enhancing cardiac function. By way of illustration, myocardin 1 is a novel cardiac-specific regulatory protein capable of modulating the phenotype of target cells within the heart, such as fibroblasts. Overexpression of myocardin 1 in fibroblasts is sufficient to activate expression of a variety of cardiac promoters, including α-myosin heavy chain, atrial natriuretic factor, Nkx2.5 and SM22. In combination with GATA4, myocardin 1 transactivates regulatory sequences in the cardiac specific homeobox Nkx2.5 gene. In addition myocardin 1 is a potent inhibitor of cell proliferation, demonstrated by a reduced number of transfected cells expressing myocardin 1 compared to those expressing a control marker gene. Further, though inhibitory of cell proliferation, myocardin appears to stimulate cardiomyocyte hypertrophy. These results may provide an explanation for the post-mitotic features of the cardiomyocytes.

B. Variants of Myocardin

Amino acid sequence variants of a myocardin polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson et al, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of myocardin, but with altered and even improved characteristics.

C. Domain Switching

Domain switching involves the generation of chimeric molecules using different but, in this case, related polypeptides. By comparing various myocardin proteins, one can make predictions as to the functionally significant regions of these molecules. It is possible, then, to switch related domains of these molecules in an effort to determine the criticality of these regions to myocardin function. These molecules may have additional value in that these "chimeras" can be distinguished from natural molecules, while possibly providing the same function. In particular, it is contemplated that one will create chimeras between myocardins, for example, between myocardin 1 & myocardin 2, myocardin1 & myocardin 3, myocardin 2 & myocardin 3, and/or myocardin 1, myocardin 2 & myocardin 3.

D. Fusion Proteins

A specialized kind of insertional variant is the fusion protein. This molecule generally has all or a substantial portion of the native molecule linked, at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

E. Purification of Proteins

It may be desirable to purify myocardin or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also includes smaller myocardin-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention also provides for the use of myocardin proteins or peptides as antigens for the immunization of animals relating to the production of antibodies. It is envisioned that myocardin or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

III. Generating Antibodies Reactive With Myocardin

In another aspect, the present invention contemplates an antibody that is immunoreactive with a myocardin molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g. Harlow and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to myocardin-related antigen epitopes. Additionally, it is proposed that monoclonal antibodies specific to the particular myocardin of different species may be utilized in other useful applications In general, both polyclonal and monoclonal antibodies against myocardin may be used in a variety of embodiments. For example, they may be employed in antibody cloning protocols to obtain cDNAs or genes encoding other myocardin. They may also be used in inhibition studies to analyze the effects of myocardin-related peptides in cells or animals. Myocardin antibodies will also be useful in immunolocalization studies to analyze the distribution of myocardins during various cellular events, for example, to determine the cellular or tissue-specific distribution of myocardin polypeptides at different points in the cell cycle. A particularly useful application of such antibodies is in purifying native or recombinant myocardin, for example, using an antibody affinity column. The operation of such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MCIP protein, polypeptide or peptide or cell expressing high levels of MCIP. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

IV. Immunologic Analysis

The use of antibodies of the present invention, in an ELISA assay is contemplated. For example, anti-myocardin antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for myocardin or a fragment thereof that differs from the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

V. Cardiomyocyte Regeneration

The present invention also involves, in another embodiment, the treatment of the loss of cardiomycoytes, for example due to myocardial infarction. In particular, myocardin plays a role in cardiac myocyte development. Thus, increasing levels of myocardin in non-cardiomyocyte target cells can be used to modulate the phenotype of such target cells such that it includes one or more functions of cardiomyocytes, whereas decreasing the levels of myocardin activity in cardiomyocytes can be used to reduce or inhibit one or more cardiomyocyte functionalities and promote cell growth.

One of the therapeutic embodiments contemplated by the present inventors is the intervention, at the molecular level, in the events involved in cardiomyocyte development. Specifically, the present inventors intend to provide, to a non-cardiomyocyte target cell, for example a cardiac fibroblast cell, an expression construct capable of providing myocardin to that cell. The lengthy discussions of gene delivery means, expression vectors and the genetic elements employed therein are incorporated into this section by reference. Exemplary gene delivery vectors are viral vectors such as adenovirus, adeno-associated virus, herpesvirus, vaccinia virus, lentivirus and retrovirus, as well as lipid-based vectors.

A. Gene Therapy

One skilled in the art recognizes that various methods of DNA delivery may be employed to deliver the polynucleotides of the present invention to specific cells for gene therapy. Further, in the context of gene therapy, a skilled artisan is cognizant that the vector to be utilized will generally contain the gene of interest operatively linked to a promoter. One skilled in the art also recognizes that, in certain instances, other sequences such as a 5' and/or 3'-UTR regulatory sequences are useful in expressing the gene of interest.

Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed release of the composition. Alternatively or additionally, the composition may be targeted by the delivery itself, for example by intracoronary delivery to target the heart (see e.g. U.S. Pat. Nos. 5,792,453 and 6,100,242, hereby incorporated by reference in their entirety). A pharmaceutically acceptable form should be employed which does not deactivate the compositions of the present invention. In pharmaceutical dosage forms, the compositions can be used alone or in appropriate association, as well as in combination, with other pharmaceutically active compounds. Preferably, a sufficient amount of vector containing the therapeutics nucleic acid sequence is administered to provide a pharmacologically effective dose of the gene product, for example to alleviate symptoms associated with the disease being treated.

One skilled in the art recognizes that other methods of delivery may likewise be utilized to administer an expression cassette into a cell. Examples include: (1) methods utilizing physical means, such as electroporation (electricity), a gene gun (physical force) or applying large volumes of a liquid (pressure); and (2) methods wherein said expression cassette is complexed with another entity, such as a lipid-based vector (e.g., a liposome), an aggregated protein or a transporter molecule. Certain of these embodiments are primarily suitable for ex vivo applications.

The actual dose and schedule can vary, for example, depending on whether the compositions are administered in combination with other pharmaceutical compositions, or depending on inter-individual differences in pharmacokinetics, drug disposition, and metabolism. Similarly, amounts to be administered can vary in in vitro applications, for example depending on the particular cell line utilized (e.g., based on the variable number and/or type of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as the nature of the sequence itself. Thus, vector amount is particularly a parameter which is preferably determined empirically and can be altered due to factors not inherent to the present invention (for instance, the cost associated with synthesis). One skilled in the art can easily make adjustments to dose in accordance with the exigencies of the particular situation.

Those of skill in the art are well aware of how to apply gene delivery to in vivo situations. By way of illustration, for viral vectors, one generally will prepare a viral vector stock. Depending on the type of virus utilized and the titer attainable, one will generally deliver $1\times10^4$, $1\times10^5$, $1\times10^6$, $1\times10^7$, $1\times10^8$, $1\times10^9$, $1\times10^{10}$, $1\times10^{11}$, $1\times10^{12}$ to $10^{13}$ infectious particles to the patient. Similar figures may be extrapolated for lipid-based or other non-viral formulations by comparing relative uptake efficiencies. Formulation as a pharmaceutically acceptable composition is discussed further below. Various routes are contemplated, but local provision to the heart, preferably by the method of Hammond, et al., supra and intra-arterial or intravenous administration are preferred.

In another embodiment, it is contemplated that blocking myocardin activity may result in stimulation of the cardiomycytes to divide. This may be accomplished in one of several ways. First, one may provide an analog of myocardin's target that binds and inhibits myocardin function, effectively creating a "suicide substrate" for myocardin. This approach also could be exploited using a mimetic (see above). Second, one could use a similar peptide target, with an additional domain actually capable of cleaving myocardin. Third, one could provide a non-functional myocardin analog that is capable of competing with myocardin peptide. And fourth, antisense or ribozyme techniques could also be used to inhibit the expression of myocardin.

B. Combined Therapy

In another embodiment, it is envisioned to use myocardin in combination with other therapeutic modalities. For example, it is known that myocardin interacts with other transcription factors. Thus, the present invention further contemplates the provision of myocardin in conjunction with one or more transcription factors, and in particular, one or more cardiac transcription factors. Examples of cardiac transcription factors include, but are not limited to, GATA4, serum response factor (SRF) and Nkx2.5.

In other embodiments, in addition to the therapies described above, one may also provide to the patient more "standard" pharmaceutical cardiac therapies. Examples of standard therapies include, without limitation, so-called "beta blockers", anti-hypertensives, cardiotonics, anti-thrombotics, vasodilators, hormone antagonists, endothelin antagonists, calcium channel blockers, phosphodiesterase inhibitors, angiotensin type 2 antagonists and cytokine blockers/inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, gene therapy may precede or follow administration of the other agent by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a myocardin gene, or the other agent will be desired. In this regard, various combinations may be employed. By way of illustration, where myocardin is "A" and the other agent or cardiac transcription factor is "B," the following permutations based on 3 and 4 total administrations are exemplary:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/A/B/A A/B/A/A

A/B/B/B B/A/B/B B/B/A/B

Other combinations are likewise contemplated.

VII. Drug Formulations and Routes for Administration to Patients

Where clinical applications are contemplated, pharmaceutical compositions will be prepared—e.g., expression vectors, virus stocks and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well know in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, buccal, rectal, vaginal or topical. Alternatively, administration may be by orthotopic, intradernal, subcutaneous, intramuscular, intraperitoneal or intravenous injection. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy syringability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

For oral administration the polypeptides of the present invention generally may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

VIII. Methods of Making Transgenic Mice

A particular embodiment of the present invention provides transgenic animals that contain myocardin-related constructs. Transgenic animals expressing myocardin, recombinant cell lines derived from such animals, and transgenic embryos may be useful in determining the exact role that myocardin plays in the development and differentiation of cardiomyocytes. Furthermore, this transgenic animal may provide an insight into heart development. The use of constitutively expressed myocardins provides a model for over-or unregulated expression. Also, transgenic animals which are "knocked out" for myocardin, in one or both alleles are contemplated.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in Hogan et al. (1994).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris,pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 $\mu$g/ml in 5 mM Tris, pH 7.4 and 0.1 mM EDTA. Other methods for purification of DNA for microinjection are described in Hogan et al. (1986), in Palmiter et al. (1982); and in Sambrook et al (1989).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

IX. Screening Assays

The present invention also contemplates the screening of compounds for various abilities to interact with and/or affect myocardin expression or function. Particularly preferred compounds will be those useful in inhibiting or promoting the actions of myocardin in regulating the development and differentiation of cardiomyocytes. In the screening assays of the present invention, the candidate substance may first be screened for basic biochemical activity—e.g., binding to a target molecule—and then tested for its ability to inhibit modulate activity, at the cellular, tissue or whole animal level.

A. Modulators and Assay Formats i) Assay Formats

The present invention provides methods of screening for modulators of myocardin expression and binding to other proteins or nucleic acids. In one embodiment, the present invention is directed to a method of:

(a) providing a myocardin polypeptide;
(b) contacting the myocardin polypeptide with the candidate substance; and
(c) determining the binding of the candidate substance to myocardin polypeptide.

In yet another embodiment, the assay looks not at binding, but at myocardin function. Such methods would comprise, for example:

(a) providing myocardin and GATA to a cell;
(b) admixing myocardin and GATA in the presence of a candidate modulator; and
(c) measuring the effect of the candidate substance on the expression of a cardiac cell gene product.

A related assay that examines the interaction of myocardin and GATA would comprise:

(a) providing myocardin and GATA to a cell;
(b) admixing myocardin and GATA in the presence of a candidate substance; and
(c) measuring the effect of the candidate substance on the interaction of myocardin and GATA.

Both of the preceding assays could be performed substituting SRF or Nkx2.5 for GATA.

In still yet other embodiments, one would look at the effect of a candidate substance on the expression of myocardin. This can be done by examining mRNA expression, although alterations in mRNA stability and translation would not be accounted for. A more direct way of assessing expression is by directly examining protein levels, for example, through Western blot or ELISA.

ii) Inhibitors and Activators

An inhibitor according to the present invention may be one which exerts an inhibitory effect on the expression or function of myocardin. By the same token, an activator according to the present invention may be one which exerts a stimulatory effect on the expression or function of myocardin.

iii) Candidate Substances

As used herein, the term "candidate substance" refers to any molecule that may potentially modulate myocardin expression or function. The candidate substance may be a protein or fragment thereof, a small molecule inhibitor, or even a nucleic acid molecule. It may prove to be the case that the most useful pharmacological compounds will be compounds that are structurally related to compounds which interact naturally with myocardin. Creating and examining the action of such molecules is known as "rational drug design," and include making predictions relating to the structure of target molecules.

The goal of rational drug design is to produce structural analogs of biologically active polypeptides or target compounds. By creating such analogs, it is possible to fashion drugs which are more active or stable than the natural molecules, which have different susceptibility to alteration or which may affect the function of various other molecules. In one approach, one would generate a three-dimensional structure for a molecule like myocardin, and then design a molecule for its ability to interact with myocardin. Alternatively, one could design a partially functional fragment of myocardin (binding, but no activity), thereby creating a competitive inhibitor. This could be accomplished by x-ray crystallography, computer modeling or by a combination of both approaches.

It also is possible to use antibodies to ascertain the structure of a target compound or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds or may be found as active combinations of known compounds which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of hypertrophic response.

Other suitable inhibitors include antisense molecules, ribozymes, and antibodies (including single chain antibodies).

It will, of course, be understood that the screening methods of the present invention are useful in themselves notwithstanding the fact that effective candidates may not be found. The invention provides methods for screening for such candidates, not solely methods of finding them.

B. In Vitro Assays

A quick, inexpensive and easy assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. In one embodiment of this kind, the screening of compounds that bind to a myocardin molecule or fragment thereof is provided The target may be either free in solution, fixed to a support, expressed in or on the surface of a cell. Either the target or the compound may be labeled, thereby permitting determining of binding. In another embodiment, the assay may measure the inhibition of binding of a target to a natural or artificial substrate or binding partner (such as myocardin). Competitive binding assays can be performed in which one of the agents (myocardin for example) is labeled. Usually, the target will be the labeled species, decreasing the chance that the labeling will interfere with the binding moiety's function. One may measure the amount of free label versus bound label to determine binding or inhibition of binding.

A technique for high throughput screening of compounds is described in WO 84/03564. Large numbers of small peptide test compounds are synthesized on a solid substrate, such as plastic pins or some other surface. The peptide test compounds are reacted with, for example, myocardin and washed. Bound polypeptide is detected by various methods.

Purified target, such as myocardin, can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link an active region (e.g., the C-terminus of myocardin) to a solid phase.

C. In Cyto Assays

Various cell lines that express myocardin can be utilized for screening of candidate substances. For example, cells containing myocardin with an engineered indicators can be used to study various functional attributes of candidate compounds. In such assays, the compound would be formulated appropriately, given its biochemical nature, and contacted with a target cell.

Depending on the assay, culture may be required. As discussed above, the cell may then be examined by virtue of a number of different physiologic assays (growth, size, $Ca^{++}$ effects). Alternatively, molecular analysis may be performed in which the function of myocardin and related pathways may be explored. This involves assays such as those for protein expression, enzyme function, substrate utilization, mRNA expression (including differential display of whole cell or polyA RNA) and others.

D. In Vivo Assays

The present invention particularly contemplates the use of various animal models. Transgenic animals may be created with constructs that permit myocardin expression and activity to be controlled and monitored. The generation of these animals has been described elsewhere in this document.

Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply.

E. Production of Inhibitors

In an extension of any of the previously described screening assays, the present invention also provide for methods of producing inhibitors. The methods comprising any of the preceding screening steps followed by an additional step of "producing the candidate substance identified as a modulator of the screened activity.

X. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Expression Pattern of Myocardin 1 During Early Heart Development

The heart is the first organ to form during mammalian development. Cardiac muscle cells originate from a region of the embryo known as the cardiac crescent and develop into a primitive heart tube along the midline of the embryo (FIG. 1). Because this is the only region of the embryo that can give rise to cardiac muscle cells, it would be expected to express a unique set of genes responsible for cardiogenesis. By identifying the genes that are uniquely expressed in this region, master control genes for heart formation can be identified. Subsequent embryonic events of looping, chamber maturation and alignment with the vascular system give rise to the mature four-chambered heart (Olson et al., 1996 and Fishman et al., 1997).

Expression of myocardin 1 was determined by wholemount (FIG. 3A) or section (FIG. 3B and FIG. 3C) in situ hybridizations to mouse embryos at E7.75 (FIG. 3A), E8.0 (FIG. 3B), and E12.5 (FIG. 3C).

In situ hybridization to cellular RNA was performed using standard techniques well known in the art, e.g., fluorescence in situ hybridization (FISH). Briefly, the samples were fixed for the appropriate time and dehydrated through a graded ethanol series. The samples were then impregnated in paraffin wax and cast into blocks. The samples were sectioned on a microtome. A specific labeled probe was prepared. The probe can be labeled with biotin or digoxigenin or with a fluorochrome-tagged deoxynucleotide. Next, the probe was hybrized to the sample. Hybridization conditions may vary with the different labeled probes. After the hybridization, samples were washed for 15 min in 37° C. 50% formamide/ 2×SSC, 15 min in 37° C. 2×SSC and 15 min in room temperature 1×SSC. The slides were equilibrated for 5 min in 4×SSC at room temperature. The slides were drained and allowed to air dray. Next, a detection solution was added. After a 45 min incubation in the detection solution, the slides were washed. A counterstain of DAPI or propidium iodide staining solution was added to the slide. The slide was viewed using a fluorescence microscope.

The results in FIG. 3 illustrate the expression pattern of myocardin 1 during early heart development. In FIG. 3A, myocardin 1 transcripts can be seen localized to the cardiac crescent. In FIG. 3B, transcripts are present throughout the heart tube in a transverse section. In FIG. 3C, transcripts are seen throughout the developing heart in a sagittal section.

As might be expected given its role in embryonic development, myocardin has also been shown to be expressed in a subset of embryonic vascular and visceral smooth muscle cells. At E13.5, myocardin expression was evident within smooth muscle cells lining the walls of the esophagus and aortic arch arteries, as well as the pulmonary outflow tract. Expression in these smooth muscle cell types was still apparent, but was diminished, by E15.5. Myocardin expression was also detected in smooth muscle cells within the lung and gut, as well as in head mesenchyme, which may serve as a source of smooth muscle precursors. Myocardin was not expressed at detectable levels in skeletal muscle.

Example 2

Expression Pattern of Myocardin 1 in Adult Mouse Tissues

The expression of myocardin 1 transcripts in adult mouse tissues was analyzed by Northern blot, utilizing techniques well known in the art. RNA was isolated from adult mouse heart, brain, spleen, lung, liver, skeletal muscle, kidney and testis according to standard RNA isolation procedures, e.g., phenol/chloroform/isoamyl alcohol (RNAzol, Life Technologies, Inc.) or guanidine thiocyanate.

Briefly, fractionated RNA was transferred from an agarose gel to a membrane by upward capillary action. The transferred RNA is cross-linked to the membrane. Next, a radiolabeled probe (DNA or RNA) was hybridized to the membrane in a formamide solution. After hybridization, autoradiography was performed to detect the transcripts.

Figure 4:
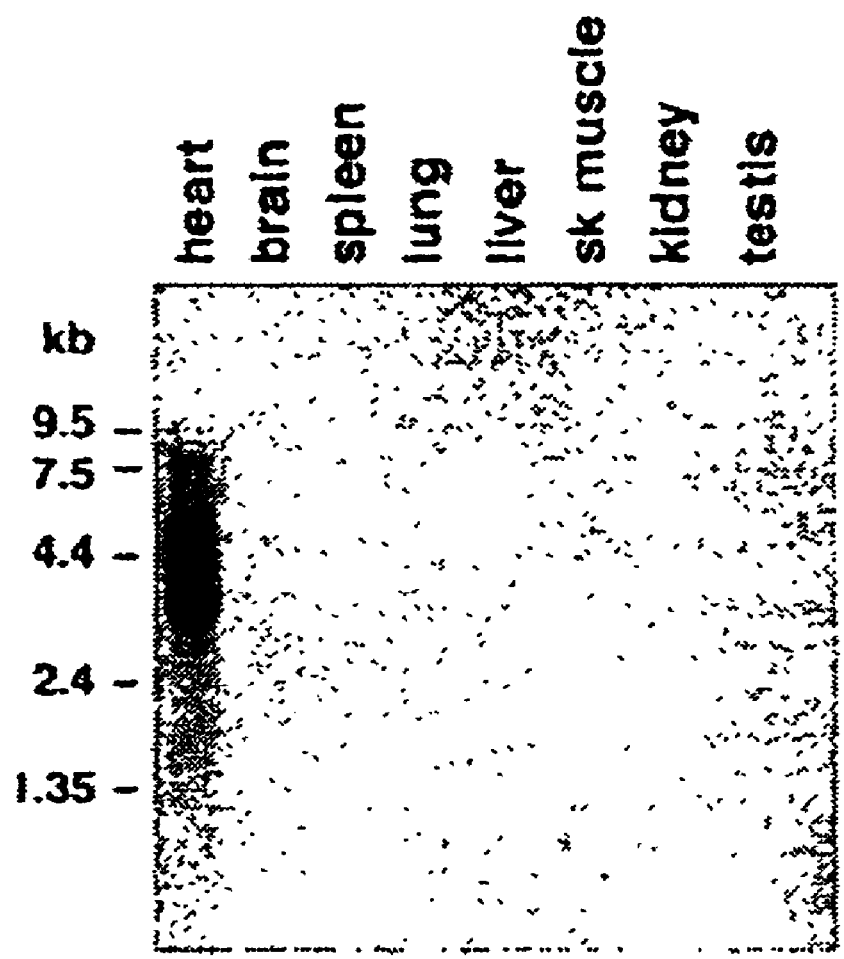
FIG. 4 Expression pattern of myocardin 1 in adult mouse tissues. The expression of myocardin 1 transcripts in adult mouse tissues was analyzed by Northern blot. Transcripts are detected only in the heart. Size markers are shown to the left.

The results in FIG. 4 show that the transcripts were detected only in the heart. A RNA molecular marker illustrates the size of the transcripts.

Example 3

Nuclear Localization of Myocardin 1 Protein

Cos cells were transiently transfected with an expression vector encoding myocardin 1 with a Flag-epitope tag. Transient transfection assays were performed using standard methods, such as LifofectAMINE plus (Life Technologies, Inc.), calcium phosphate or electroporation. Briefly, the cells were plated 12 hr before transfection in tissue culture dishes. They were transfected with a total of about 0.5–1.0 μg of plasmid DNA. The subcellular location of myocardin 1 protein was determined by immunostaining with anti-Flag antibody.

Figure 5:
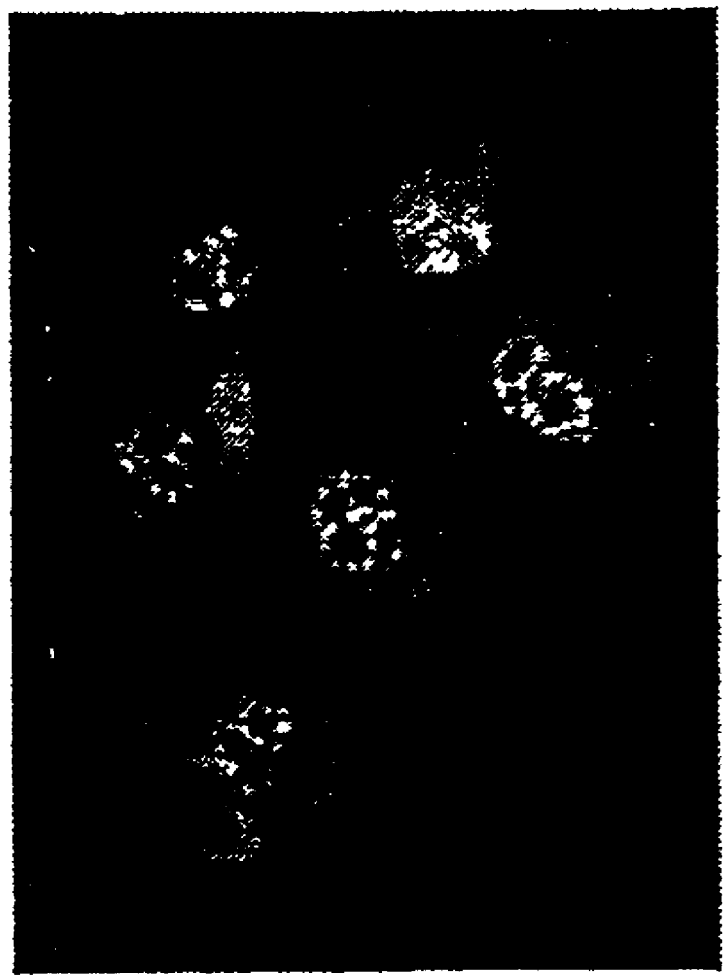
FIG. 5 Nuclear localization of myocardin 1 protein. Cos cells were transiently transfected with an expression vector encoding myocardin 1 with a Flag-epitope tag. The subcellular location of myocardin 1 protein was determined by immunostaining with anti-Flag antibody. The myocardin 1 protein is substantially localized to the nucleus. The inset in the lower right corner shows an enlargement of a single cell, with strong myocardin 1 staining in the nucleus, but excluded from the nucleoli.

All myocardin 1 protein is localized to the nucleus as illustrated in FIG. 5. The inset in the lower right corner shows an enlargement of a single cell, with strong myocardin 1 staining in the nucleus, but excluded from the nucleoli.

Example 4

Structure of Myocardin 1 and Mapping of Transcription Activation Domains

Portions of myocardin 1 were fused to the DNA binding domain of yeast GAL4 and tested in transfected Cos cells for transcriptional activity against a GAL4-dependent luciferase reporter. The relative transcriptional activities of different myocardin 1 fragments are show in FIG. 6.

The nuclear localization sequence (NLS) is located between residues 245 and 254, within a basic region at residues 243–260. A glutamine-rich (Q) domain is located between residues 287–320. The SA-P domain is found at residues 380–414. The transcription activation domain is located at the carboxyl-terminus at 670 to 935. The carboxyl-terminus is an extremely potent transcription activation domain, able to activate the reporter over 1000-fold, to a level comparable to that of the powerful viral coactivator VP16 (not shown).

As might be expected, given its apparent influence on transcription, myocardin contains an SAP domain (named for nuclear scaffold attachment factors A and B), as found in a variety of proteins that affect not only transcription but also nuclear architecture. The SAP domain is a 35 amino acid motif containing two predicted amphipathic helices separated by an intervening region with an invariant glycine residue. Functional aspects of the SAP domain were examined by introducing proline mutations into helix-1 or -2. These mutations had only a modest effect on the ability of myocardin to transactivate the SM22 promoter (which transactivation is discussed further below). Similarly, the deletion of the linker region between the two helices of the SAP domain, shown previously to be required for DNA binding by SAF-A, had little effect on SM22 activation, but eliminated ANF activation (discussed below).

Example 5

Trans-Activation of the SM22 Promoter by Myocardin

Cos cells were transiently transfected with a luciferase reporter gene containing the 1.4 kb SM22 promoter and expression vectors encoding myocardin 1 and SRF. Briefly, the cells were plated 12 hr before transfection in tissue culture dishes. They were transfected with plasmid DNA. Forty eight hr after transfection, the cells were harvested. Luciferase assays of whole cell extracts were conducted by standard methods well known in the art.

Figure 7:
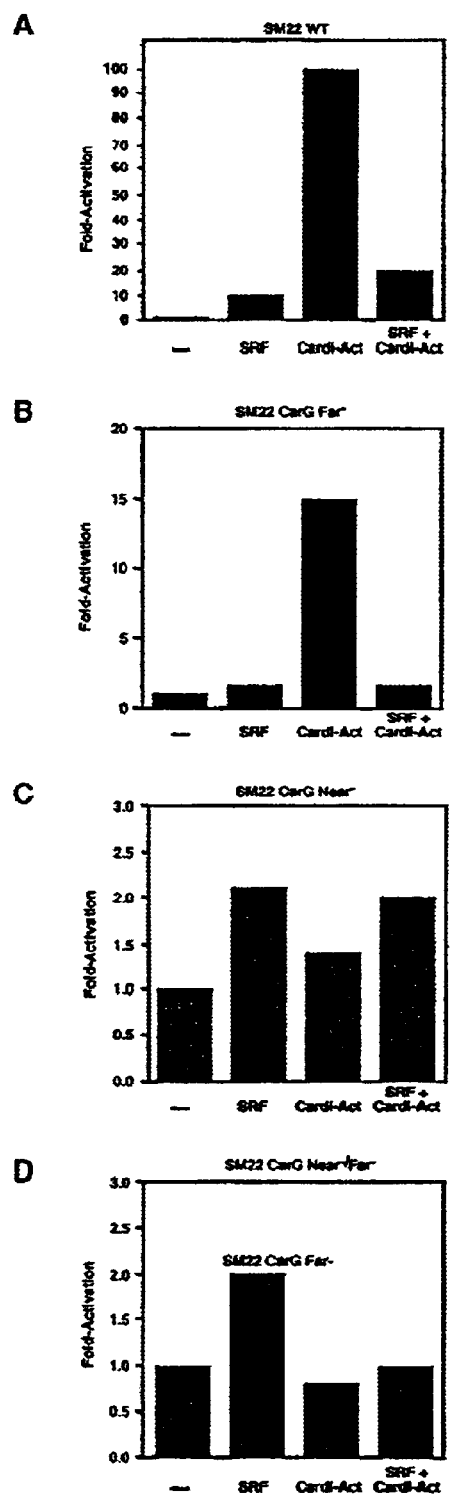
FIG. 7A–D Trans-activation of the SM22 promoter by myocardin 1. Cos cells were transiently transfected with a luciferase reporter gene containing the 1.4 kb SM22 promoter and expression vectors encoding myocardin 1 and SRF, as indicated. Forty eight hr later, cells were harvested and luciferase activity was assayed.

FIG. 7A shows activity of the wild-type SM22 promoter, which was transactivated about 100-fold by myocardin. FIG. 7B shows activity of the SM22 promoter with a mutation in the distal CArG box (CArG-far). This promoter was also activated by myocardin, but not to the same extent as the wild-type promoter. FIG. 7C shows activity of the SM22 promoter with a mutation in the proximal CArG box (CArG-near). This promoter has lost almost all responsiveness to myocardin, as has the promoter with both the CArG boxes mutated (FIG. 7D). Both myocardin 1 and N-terminally truncated myocardin 1 have demonstrated similar activities in these assays.

Additional studies have further demonstrated myocardin's potency as a transactivator and its preferential action via CArG boxes. By way of example, myocardin's ability to transactivate reporter genes containing four tandem copies of SM22 CArG-near or the c-fos SRE linked to the E1b promoter was tested and compared to SRF. These reporters were transactivated several hundred-fold by myocardin, whereas SRF was only able to activate expression by 8-fold.

Example 6

Myocardin 1 and MEF2C Cooperatively Activate the MLC2V Promoter

Figure 8:
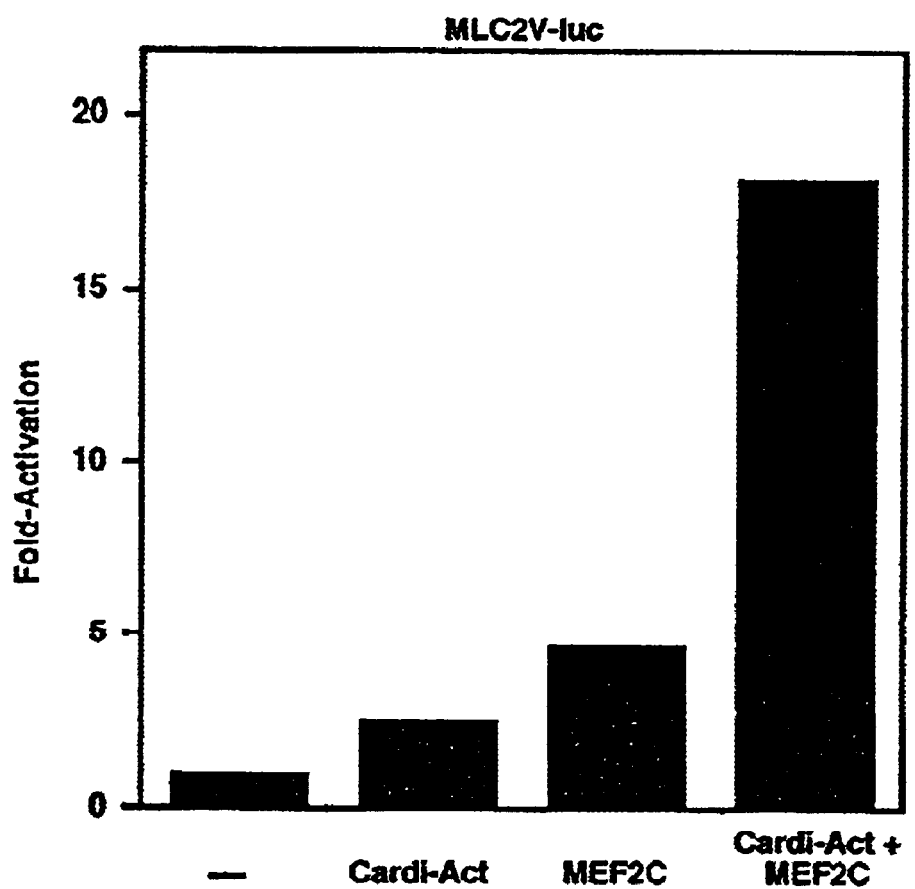
FIG. 8 Myocardin 1 and MEF2C cooperatively activate the MLC2V promoter. Cos cells were transiently transfected with a luciferase reporter gene containing the MLC2V promoter and expression vectors encoding myocardin 1 and MEF2C, as indicated. Forty eight hours later, cells were harvested and luciferase activity was assayed. The results show that myocardin 1 and MEF2C synergistically activate MLC2V transcription.

Cos cells were transiently transfected with a luciferase reporter gene containing the MLC2V promoter and expression vectors encoding myocardin 1 and MEF2C, as indicated. Forty eight hr later, cells were harvested and luciferase activity was assayed. The results in FIG. 8 show that myocardin 1 and MEF2C synergistically activate MLC2V transcription. Both myocardin 1 and N-terminally truncated myocardin 1 have demonstrated similar activities in these assays.

Example 7

Interactions of Myocardin 1 and GATA4

A. GATA4 Represses Myocardin Activation of the ANF Promoter

Figure 9:
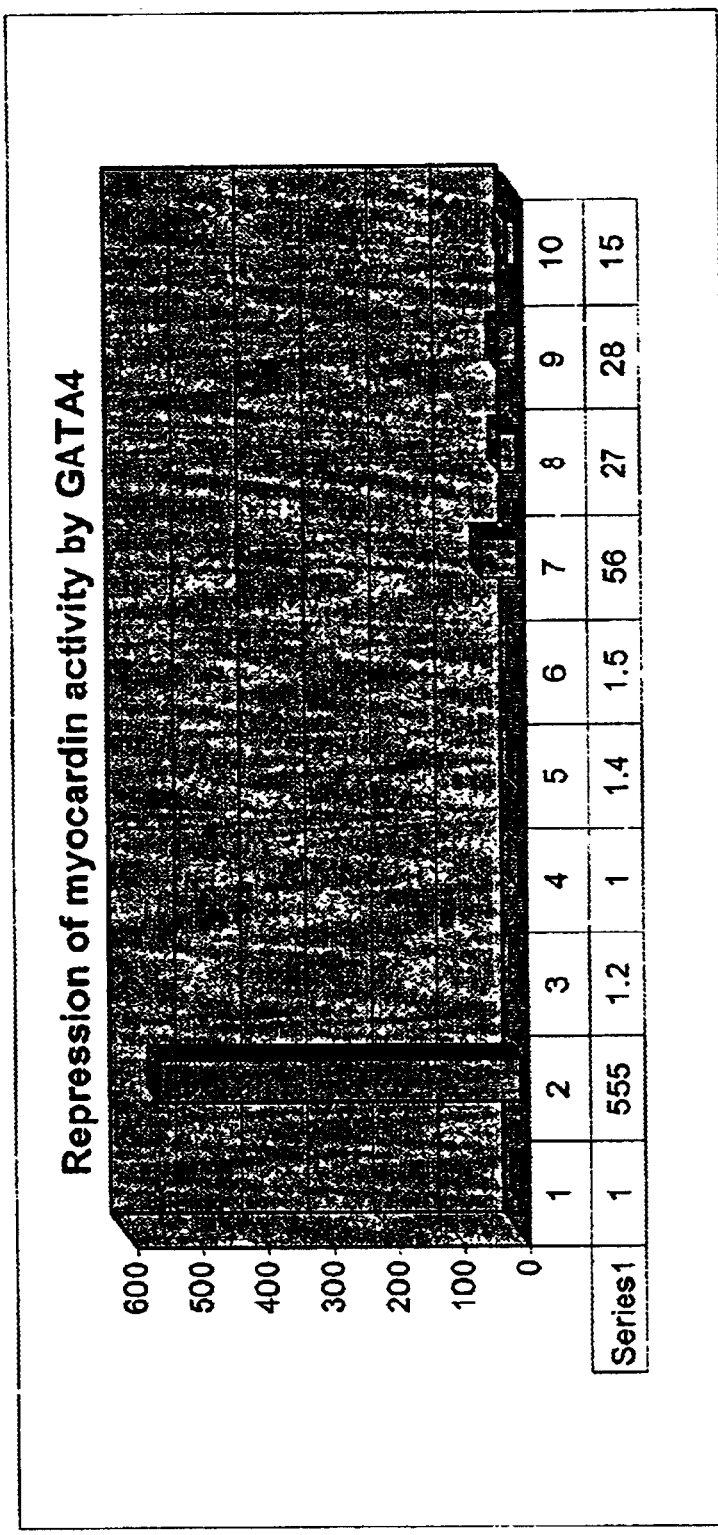
FIG. 9 GATA4 represses myocardin 1 activation of the ANF promoter. HeLa cells and Cos cells were transiently transfected with a luciferase reporter gene containing the ANF promoter and expression vectors encoding myocardin 1 and GATA4 (1=100 ng anf-luc; 2=100 μg anf-luc, 100 ng myocardin; 3=100 ng anf-luc, 10 ng GATA4; 4=100 ng anf-luc, 20 ng GATA4; 5=100 ng anf-luc, 50 ng GATA4; 6=100 ng anf-luc, 100 ng GATA4; 7=100 ng anf-luc, 100 ng myocardin, 10 ng GATA4; 8=100 ng anf-luc, 100 ng myocardin, 20 ng GATA4; 9=100 ng anf-luc, 100 ng myocardin, 50 ng GATA4; 10=100 ng anf-luc, 100 ng myocardin, 100 ng GATA4). Forty eight hours later, cells were harvested and luciferase activity was assayed. The results show that activation of ANF transcription by myocardin 1 is repressed in the presence of GATA4.

HeLa cells and Cos cells were transiently transfected with a luciferase reporter gene containing the ANF promoter and expression vectors encoding myocardin 1 and GATA4, as indicated. Forty eight hr later, cells were harvested and luciferase activity was assayed. The results in FIG. 9 show that GATA4 represses myocardin 1 activation of ANF transcription.

B. Myocardin 1 and GATA4 Cooperatively Activate the Nkx2.5 Promoter

Figure 13:
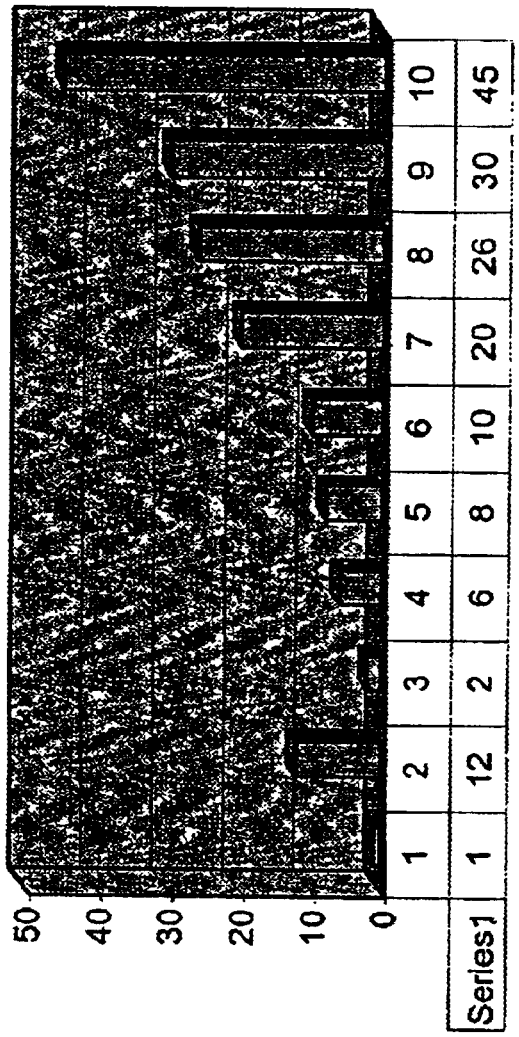
FIG. 13 GATA4 and myocardin 1 activate of the NKX2.5 promoter. HeLa cells and Cos cells were transiently transfected with a luciferase reporter gene containing the NKX2.5 promoter and expression vectors encoding myocardin 1 and GATA4 (1=100 ng nkx-luc; 2=100 ng nkxf-luc, 500 ng myocardin; 3=100 ng nkx-luc, 10 ng GATA4; 4=100 ng nkx-luc, 20 ng GATA4; 5=100 ng nkx-luc, 50 ng GATA4; 6=100 ng nkx-luc, 100 ng GATA4; 7=100 ng nkx-luc, 500 ng myocardin, 10 ng GATA4; 8=100 ng nkx-luc, 500 ng myocardin, 20 ng GATA4; 9=100 ng nkx-luc, 500 ng myocardin, 50 ng GATA4; 10=100 ng nkx-luc, 500 ng myocardin, 100 ng GATA4). Forty eight hours later, cells were harvested and luciferase activity was assayed. The results show activation of NKX2.5 transcription by myocardin 1 and GATA4.

HeLa cells (and/or Cos cells) were transiently transfected with a luciferase reporter gene containing the Nkx2.5 promoter and expression vectors encoding myocardin 1 and GATA4. Approximately forty eight hr later, cells were harvested and luciferase activity was assayed. The results demonstrated that myocardin 1 and GATA4 cooperatively activated Nkx2.5 transcription. Both myocardin 1 and N-terminally truncated myocardin 1 have demonstrated similar activities in these GATA4 interaction assays. FIG. 13.

Example 8

Myocardin 1 and Nkx2.5 Cooperatively Activate the α-MHC Promoter

Figure 10:
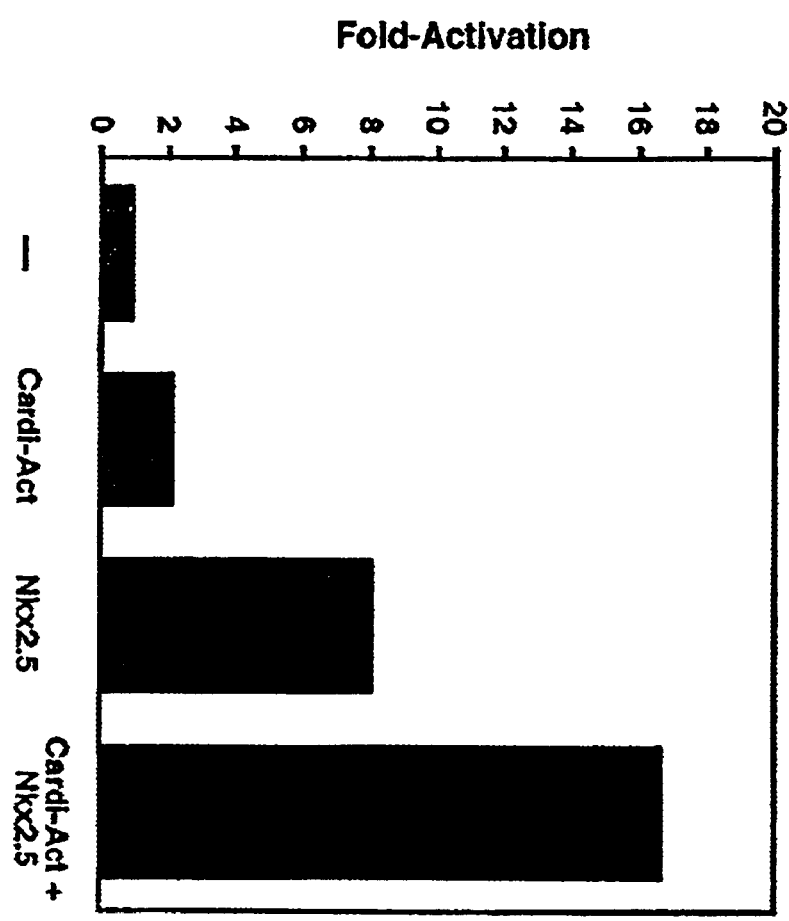
FIG. 10 Myocardin 1 and Nkx2.5 cooperatively activate the α-MHC promoter. HeLa cells were transiently transfected with a luciferase reporter gene containing the α-MHC promoter and expression vectors encoding myocardin 1 and Nkx2.5, as indicated. Forty eight hr later, cells were harvested and luciferase activity was assayed. The results show that myocardin 1 and Nkx2.5 synergistically activate α-MHC transcription.

HeLa cells were transiently transfected with a luciferase reporter gene containing the α-MHC promoter and expression vectors encoding myocardin 1 and Nkx2.5. Forty eight hr later, cells were harvested and luciferase activity was assayed. The results in FIG. 10 show that myocardin 1 and Nkx2.5 synergistically activate α-MHC transcription.

Example 9

Myocardin Forms a Complex with SRF

To further examine the mechanism for CArG box-dependent transcriptional activation, the inventors tested whether myocardin translated in vitro could bind to the CArG boxes from the SM22 promoter. SRF bound to both CArG boxes, but no binding of myocardin to either CArG box was detectable in gel mobility shift assays. However, myocardin in the presence of SRF gave rise to a prominent ternary complex with the CArG box sequence. This ternary complex was supershifted by antibodies against SRF or FLAG-tagged myocardin. The total amount of SRF DNA binding was comparable in the presence and absence of myocardin, suggesting that association of SRF with myocardin does not alter the affinity of SRF fro the CArG box. Myocardin and SRF also formed a ternary complex with the c-fos and ANF CArG boxes, the intensity of which correlated directly with the relative binding of SRF to the site. The lack of obvious homology in the flanking sequences of these different CArG boxes suggests that myocardin associates directly with SRF and does not depend on specific DNA sequences for ternary complex formation.

The region of myocardin required for ternary complex formation with SRF was determined using myocardin deletion mutants. Deletion of the amino-terminal 276 amino acid abolished association with SRF, as did larger amino-terminal deletions. In contrast, deletions from near the middle of the protein to the carboxyl terminus did not affect SRF interaction. Deletion of the Q-rich domain or the basic regions also abolished ternary complex formation, whereas mutation of the SAP domain did not. These findings are consistent with the interpretation that the amino terminus of myocardin confers transcriptional specificity by mediating association with SRF, whereas the carboxyl terminus activates transcription.

To determine whether myocardin interacts with the DNA binding or transcription activation domain of SRF, the inventors performed gel mobility shift assays with an SRF deletion mutant encompassing the MADS domain, but lacking the amino and carboxyl termini. This SRF mutation (SRF 100–300) bound the CArG box sequence and formed a ternary complex with myocardin.

Association of myocardin and SRF was also readily detectable in coimmunoprecipitation assays of epitope-tagged proteins. Interaction was dependent on the amino-terminal regions of myocardin. The core MADS domain of SRF (residues 133–266) was also necessary and sufficient to mediate association with myocardin in coimmunoprecipitation assays.

Without wishing to be bound by any particular theory, these results suggest that myocardin interacts with SRF to form a stable ternary complex which may be an aspect of the mechanism of action of myocardin as a transcription activator. Both myocardin 1 and N-terminally truncated myocardin 1 have demonstrated similar activities in this regard.

Myocardin has also been shown to be sensitive to the level of SRF, such that at low concentrations of SRF expression plasmid, myocardin and SRF synergistically activated SM22 transcription, whereas at higher concentrations of SRF, transcriptional activation by myocardin was reduced. Inhibition of myocardin-dependent transcription by excess SRF could be relieved by increasing the amount of myocardin. Thus, the ratio of SRF to myocardin appears relevant for transcriptional activation by myocardin, such that exceeding an optimal ratio with an excess of SRF can result in attenuation of myocardin activity.

Example 10

Inhibition of Cardiomyocyte Differentiation in Xenopus Embryos by Dominant Negative Myocardin Further confirming the role of myocardin in cardiomyocyte differentiation, mRNA from a dominant negative myocardin mutant was injected into Xenopus embryos. A dramatic reduction in the expression of transcripts for cardiac α-actin and α-tropomyosin was observed. The effects on cardiac differentiation were highly specific as demonstrated by the normal overall appearance of the embryo. Also observed was a dose-dependent reduction in expression of cardiac markers, such that approximately 90% of injected embryos exhibited a reduction or complete elimination of cardiac gene expression.

Example 11

Overexpression of Myocardin Induces Hypertrophy in Cardiomyocytes

The inventors have investigated how myocardin affects the growth and/or All differentiation of cardiomyocytes by overexpressing myocardin in cardiomyocytes using adenoviral delivering system. Cardiomyocyte cultures were prepared by dissociation of 1-day-old neonatal rat hearts and were plated differentially to remove fibroblasts. Cells were plated on glass coverslips coated with 4 µg/cm² laminin in 4:1 Dulbecco's modified Eagle's medium (DMEM):199 medium with 10% horse serum and 5% fetal calf serum at a density of 5×10⁴ cells/cm². Eighteen hours after plating, cells were changed into serum-free media and infected with adenoviruses expressing either myocardin or β-galactosidase (as a control) at a multiplicity of infection (m.o.i.) of 100.

For immunofluorescence, cells were fixed in 3.7% formaldehyde on ice for 30 min, permeabilized with 0.1% Triton X-100 in phosphate-buffered saline (PBS) and blocked with 5% serum in PBS for 1 hour at room temperature. Cells were incubated with monoclonal anti-α-actinin (sarcomeric) or anti-ANF (atrial natriuretic factor) antibodies at a dilution of 1:200 in blocking buffer for 1 hour at 37° C., washed and incubated with fluorescein-conjugated horse anti-mouse IgG antibody at a dilution of 1:200 in blocking buffer for 1 hour at 37° C. Following secondary antibody incubation, cells were washed with PBS.

Figure 11:
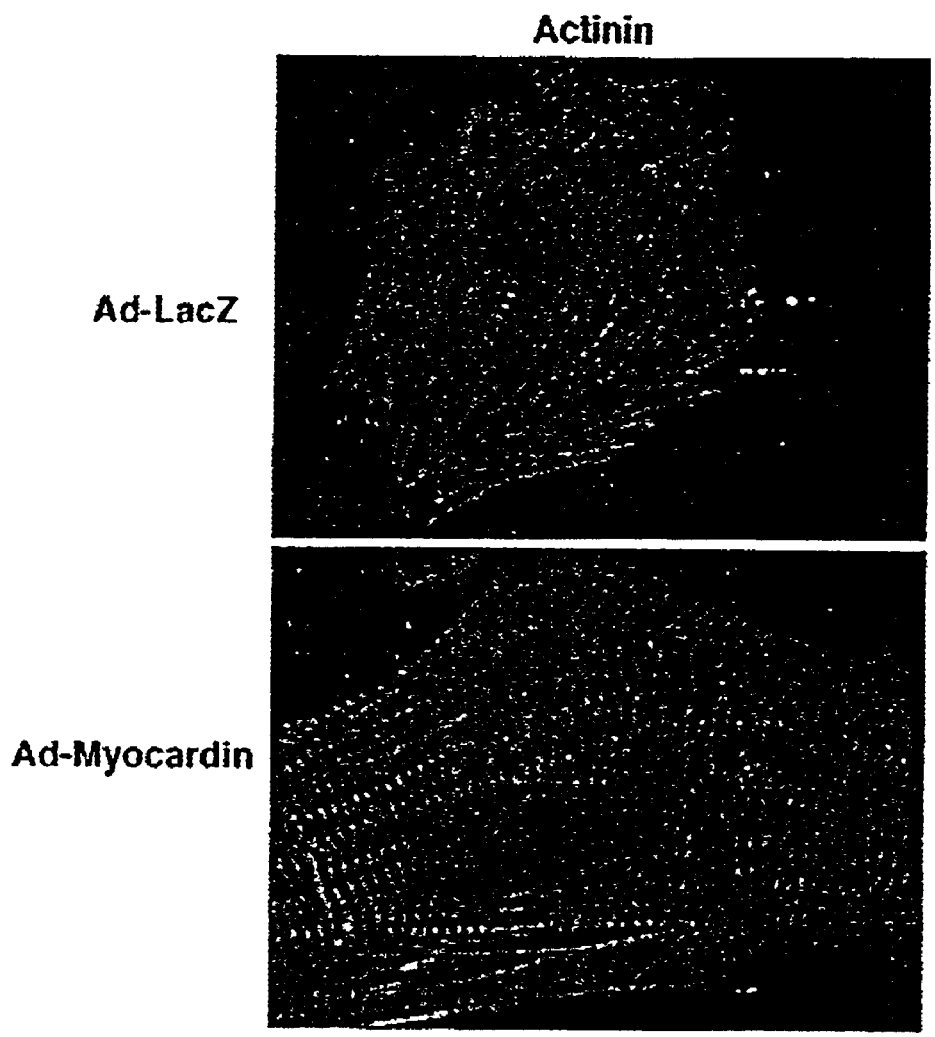
FIG. 11 Overexpression of myocardin induces serial assembly of sarcomeres in cardiomyocytes. Cardiomyocytes were infected with adenoviruses expressing either myocardin (Ad-myocardin) or β-galactosidase(Ad-LacZ), serum deprived, and immunostained with anti-sarcomeric-α-actininat antibody 24 hour post-infection.
Figure 12:
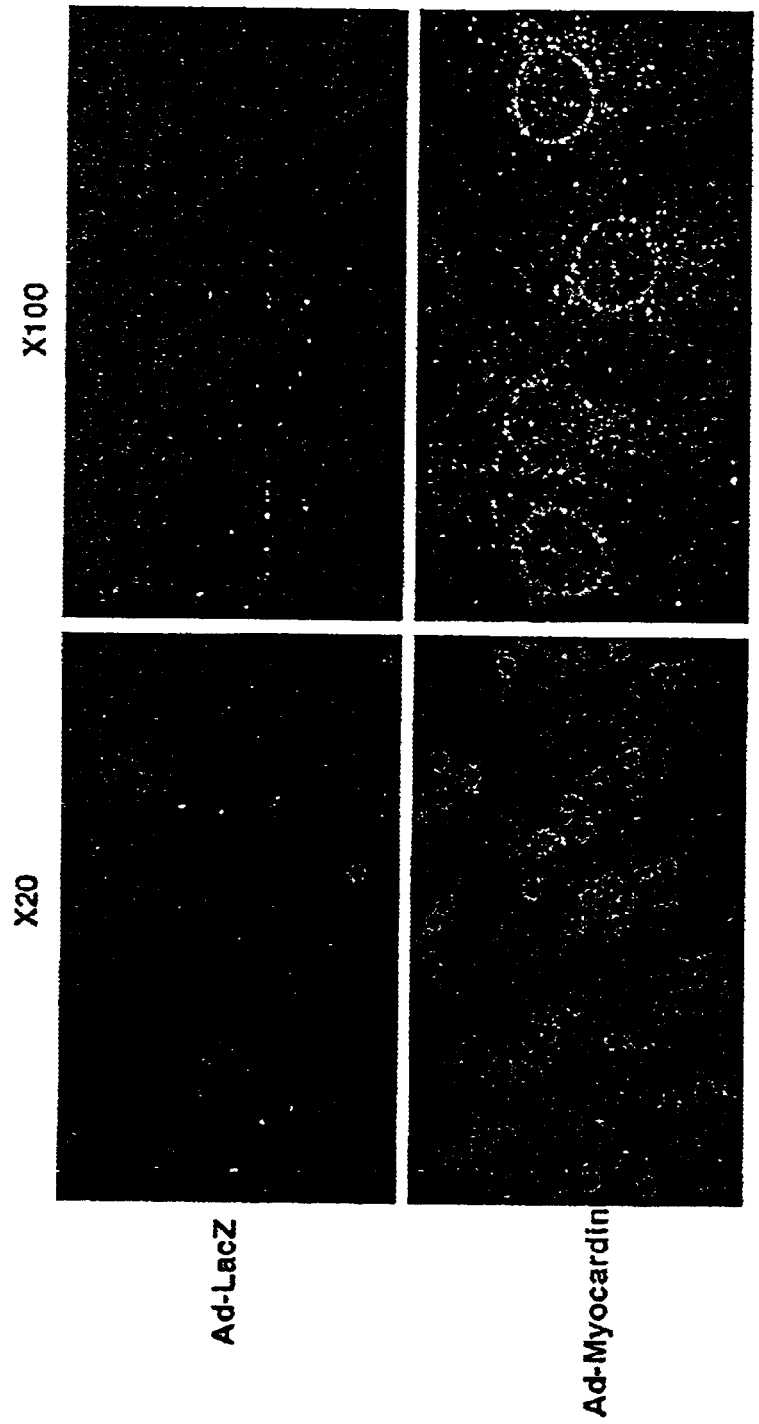
FIG. 12 Overexpression of myocardin induces ANF expression in cardiomyocytes. Cardiomyocytes were infected with adenoviruses expressing either myocardin (Ad-myocardin) or β-galactosidase (Ad-LacZ), serum deprived, and immunostained with anti-ANF antibody 24 hour post-infection. Images were captured at two different magnifications (×20,×100).

The results are shown in FIGS. 11 and 12. Overexpression of myocardin in neonatal cardiomyocytes induces assembly of sacomeres and expression of atrium natriuretic factor (ANF), markers of cardiac hypertrophy.

References

The following references, to the extent that they provide exemplary procedural or other details supplementary to those set forth herein, are specifically incorporated herein by reference.

EPO Patent 0 273 085
EPO Patent 0 320 308
U.S. Pat. No. 5,354,855
U.S. Pat. No. 4,196,265
U.S. Pat. No. 4,554,101
U.S. Pat. No. 4,683,195
U.S. Pat. No. 4,683,202
U.S. Pat. No. 4,800,159
U.S. Pat. No. 4,873,191
U.S. Pat. No. 4,883,750
U.S. Pat. No. 5,279,721
U.S. Pat. No. 4,879,236
U.S. Pat. No. 5,871,986
U.S. Pat. No. 5,792,453
U.S. Pat. No. 6,100,242
WO 84/03564
WO 90/07641
Aramburu et al., *Mol. Cell*, 1:627–637, 1998.
Aramburu et al., *Science*, 285:2129–2133, 1999.
Ausubel et al., In: Current Protocols in Molecular Biology, John, Wiley & Sons, Inc., 1994.
Baichwal and Sugden, In: *Gene Transfer*, Kucherlapati R, ed., New York, Plenum Press, pp. 117–148,1986.
Barany and Merrifield, The Peptides, Gross and Meienhofer, eds., Academic Press, New York, pp. 1–284, 1979.
Barnes et al., *J. Biol. Chem.*, 272(17):11510-7, 1997.
Beals et al., *Genes Dev.*, 11:824–834, 1997.
Benvenisty and Neshif, *Proc. Nat'l Acad. Sci. USA* 83(24):9551–9555, 1986.
Bhavsar et al., *Genomics*, 35(1):11–23, 1996.
Brinster et al., *Proc. Nat'l Acad. Sci. USA*, 82: 4438–4442, 1985.
Capaldi et al., *Biochem. Biophys. Res. Comm.*, 76:425, 1977
Chang et al., 14:124A, 1991.

Chen and Okayama, 7:2745–2752, 1987.
Chin et al., *Genes Dev.*, 12:2499–2509, 1998.
Clipstone and Crabtree, *Nature*, 357:695–697, 1992.
Coffin, Retroviridae and Their Replication. In: *Virology*, Fields et al., eds., Raven Press, New York, pp. 1437–1500, 1990.
Cook et al., *Cell*, 27:487–496, 1981.
Couch et al., *Am. Rev. Resp. Dis.*, 88:394–403, 1963.
Coupar et al., *Gene*, 68:1–10, 1988.
Crabtree, *Cell*, 96:611–614, 1990.
Ding et al., *Circ. Res.*, 84:729–734, 1999.
Dubensky et al., *Proc. Nat'l Acad. Sci. USA*, 81:7529–7533, 1984.
Dunn et al., *J Biol. Chem.*, 274:21908–21912, 1999.
Edmondson et al., *Development*, 120:1251–1263, 1994.
Epstein, In *The Metabolic and Molecular Bases of Inherited Disease: in Down Syndrome (Trisomy 21)*, Scriver, Beaudet, Valle, (eds), 7th Ed., Vol. 1, pp. 749–794, McGraw-Hill, Inc., New York, 1995.
Fechheimer et al., *Proc. Nat'l Acad. Sci. USA*, 84:8463–8467, 1987.
Ferkol et al., *FASEB J.*, 7:1081–1091, 1993.
Fishman and Olson, *Cell* 91, 153–156, 1997.
Forster & Symons, *Cell*, 49:211–220, 1987.
Fraley et al., *Proc. Nat'l Acad. Sci. USA*, 76:3348–3352, 1979.
Franz et al., *Cardioscience*, 5(4):235–43, 1994.
Freifelder, *Physical Biochemistry Applications to Biochemistry and Molecular Biology*, 2nd ed. Wm. Freeman and Co., New York, N.Y., 1982.
Friedmann, "Progress toward human gene therapy", *Science*, 244:1275–1281, 1989.
Fuentes et al., *Genomics*, 44:358–361, 1997.
Fuentes et al., *Hum. Mol Genet.*, 4:1935–1944, 1995.
Gerlach et al., *Nature (London)*, 328:802–805, 1987.
Ghosh and Bachhawat, Targeting of Liposomes to Hepatocytes. In: *Liver Diseases, Targeted Diagnosis and Therapy Using Specific Receptors and Ligands.* Wu et al., eds., Marcel Dekker, New York, pp. 87–104, 1991.
Ghosh-Choudhury et al., *EMBO J*, 6:1733–1739, 1987.
Goding, 1986, In: *Monoclonal Antibodies: Principles and Practice*, 2d ed., Academic Press, Orlando, Fla., pp. 60–61, and 71–74, 1986.
Gomez-Foix et al., *J. Biol. Chem.*, 267:25129–25134, 1992.
Gopal, *Mol. Cell Biol.*, 5:1188–1190, 1985.
Gopal-Srivastava et al., *Mol. Cell Biol.*, 15(12):7081–90, 1995.
Gorman et al., *Proc Nat'l Acad. Sci. (USA)*, 1982; 79(22):6777–81, 1982.
Graef et al., *Nature*, 401:703–8, 1999.
Graham and Prevec, In: *Methods in Molecular Biology: Gene Transfer and Expression Protocol*, E. J. Murray, ed., Humana Press, Clifton, N.J., 7:109–128, 1991.
Graham and van der Eb, *Virology*, 52:456–467, 1973.
Graham et. al., *J. Gen. Virol.*, 36(1):59–74, 1977.
Grayson et al., *J. Cell. Biochem.*, 70:366–375, 1998.
Grayson et al., *Mol. Cell. Biol.*, 15:1870–1878, 1995.
Grunhaus and Horwitz, *Seminar in Virology*, 3:237–252, 1992.
Guzman et al., *Circulation*, 88(6):2838–48, 1993.
Hammond et al., *Clin. Res.*, 42:123A, 1994.
Harland and Weintraub, *J. Cell Biol.*, 101:1094–1099, 1985.
Harlow and Lane, Antibodies: A Laboratory manual., Cold Spring Harbor Laboratory, 1988.
Harvey, *Dev. Biol.* 178:203–216, 1996.
Hermonat and Muzycska, *Proc. Nat'l Acad. Sci. USA*, 81:6466–6470, 1984.

Hersdorffer et al., *DNA Cell Biol.*, 9:713–723, 1990.
Herz and Gerard, *Proc. Nat'l Acad. Sci. USA*, 90:2812–2816, 1993.
Hidaka et. al., *J Clin. Invest.* 103(4):549–587, 1999.
Ho et al., *J. Exp. Med.*, 184:101–112, 1996.
Ho et al., *Cell*, 85:973–983, 1996.
Ho et al., *J. Biol. Chem.*, 270:19898–19907, 1995.
Hoey et al., *Immunity*, 2:461–472, 1995.
Hogan et al., In: Manipulating the Mouse Embryo: A Laboratory Manual., 2nd ed., Cold Spring Harbor Laboratory Press, 1994.
Horwich et al., *J. Virol.*, 64:642–650, 1990.
Innis et al., *PCR Protocols*, Academic Press, Inc., San Diego Calif., 1990.
Johnson et al., Peptide Turn Mimetics" IN: *Biotechnology And Pharmacy*, Pezzuto et al., eds., Chapman and Hall, New York, 1993.
Jones and Shenk, *Cell*, 13:181–188, 1978.
Joyce, *Nature*, 338:217–244, 1989.
Kaneda et al., *Science*, 243:375–378, 1989.
Karlsson et al., *EMBO J.*, 5:2377–2385, 1986.
Kashishian et al., *J. Biol. Chem.*, 273:27412–27419, 1998.
Kato et al., *J. Biol. Chem.*, 266:3361–3364, 1991.
Kelly et al., *J. Cell Biol.*, 129(2):383–96, 1995.
Kim & Cook, *Proc. Nat'l Acad. Sci. USA*, 84:8788–8792, 1987.
Kimura et al., *Dev. Growth Differ.* 39(3):257–65, 1997.
Kingsbury and Cunningham, Yeast Genetics and Molecular Meeting, Abstract, p. 98, Genetics Society of America, Bethesda, Md., 1998.
Klauck et al., *Science*, 271:1589–1592, 1996.
Klee et al., *J. Biol. Chem.*, 273:13367–13370, 1998.
Klein et al., *Nature*, 327:70–73, 1987.
Kodama, et al., *Cir. Res.* 81:656–663, 1997.
Kyte and Doolittle, *J. Mol. Biol.*, 157(1):105–132, 1982.
Lai et al., *J. Biol. Chem.*, 273:18325–18331, 1998.
LaPointe et al., *Hypertension* 27(3 Pt 2):715–22, 1996.
Le Gal La Salle et al., *Science*, 259:988–990, 1993.
Leor et al., *Circulation* 94(Suppl. II):332–336, 1996.
Levrero et al., *Gene*, 101:195–202, 1991.
Lin et. al., *Science*, 276:1404–1407, 1997.
Liu et al., *EMBO J.*, 16:143–153, 1997.
Loh et al., *J. Biol. Chem.*, 271:10884–10891, 1996.
Luo et al., *Proc. Nat'l Acad. Sci. USA*, 93:8907–8912, 1996.
Macejak and Sarnow, *Nature*, 353:90–94, 1991.
Makino et. al., *J. Clin. Invest.*, 103:697–705, 1999.
Mann et al., *Cell*, 33:153–159, 1983.
Mao and Wiedmann, *J. Biol. Chem.*, 274:31102–31107, 1999.
Mao et al., *Science*, 286:785–790, 1999.
Marban et al., *Proc. Nat'l Acad. Sci. USA*, 84:6005–6009, 1987.
Markowitz et al., *J. Virol.*, 62:1120–1124, 1988.
Masuda et al., *Mol. Cell. Biol.*, 17:2066–2075, 1997.
Masuda et al., *Mol. Cell. Biol.*, 15:2697–2706, 1995.
Merrifield, *Science*, 232: 341–347, 1986.
Mesaeli et al., *J. Cell Biol.*, 144:857–868, 1999.
Michel & Westhof, *J. Mol. Biol.*, 216:585–610, 1990.
Miyazaki et al., *J. Biol. Chem.*, 271:14567–14571, 1996.
Molkentin et al., *Cell*, 93:215–228, 1998.
Moss et al., *J. Biol. Chem.*, 271(49):31688–94, 1996.
Mulligan, *Science*, 260:926–932, 1993.
Musaro et al., *Nature*, 400:581–585, 1999.
Naya et al., *Development*, 126:2045–2052, 1999.
Nicolas and Rubinstein, In: *Vectors: A survey of molecular cloning vectors and their uses*, Rodriguez and Denhardt, eds., Stoneham: Butterworth, pp. 494–513, 1988.
Nicolau and Sene, *Biochim. Biophys. Acta*, 721:185–190, 1982.
Nicolau et al., *Methods Enzymol.*, 149:157–176, 1987.
O'Keefe et al., *Nature*, 357:692–694, 1992.
Olson, E. N. 1990. *Genes & Dev.* 4, 1454–1461.
Olson and Srivastava, D. 1996. *Science* 272, 671–676.
Palmiter et al., *Nature*, 300:611, 1982.
Pan, et al., *Circ. Res.* 81:611–617, 1997.
Parks et al., *Anal. Biochem.*, 216:413–417, 1994.
Paskind et al., *Virology*, 67:242–248, 1975.
Pelletier and Sonenberg, *Nature*, 334:320–325, 1988.
Perales et al., *Proc. Nat'l Acad. Sci.* 91:4086–4090, 1994.
Pignon et al., *Hum. Mutat.*, 3: 126–132, 1994.
Potter et. al., *Proc. Nat'l Acad. Sci. USA*, 81:7161–7165, 1984.
Racher et al., *Biotechnology Techniques*, 9:169–174, 1995.
Ragot et al., *Nature*, 361:647–650, 1993.
Rao et al., *Annu. Rev. Immunol.*, 15:707–747, 1997.
Reinhold-Hurek & Shub, *Nature*, 357:173–176, 1992.
Remington's Pharmaceutical Science",$15^{th}$ Ed., pg. 1035–1038 and 1570–1580.
Renan, *Radiother. Oncol.*, 19:197–218, 1990.
Rich et al., *Hum. Gene Ther.*, 4:461–476, 1993.
Ridgeway, Mammalian Expression Vectors, In: *Vectors: A Survey of Molecular Cloning Vectors and Their Uses*, Rodriguez et al., eds., Stoneham: Butterworth, pp. 467–492, 1988.
Rippe et. al., 10:689–695, 1990.
Ritchie, M. E., *J. Biol. Chem.* 271(41):25485–25491, 1996.
Rosenfeld et al., *Cell*, 68:143–155, 1992.
Rosenfeld et al., *Science*, 252:431–434, 1991.
Roux et al., *Proc. Nat'l Acad. Sci. USA*, 86:9079–9083, 1989.
Sambrook et. al., In: *Molecular Cloning: A Laboratory Manual.*, 2d Ed., Cold Spring Harbor Laboratory Press, Cold Spring Harbor, N.Y., 1989.
Sarver et al., *Science*, 247:1222–1225, 1990.
Scanlon et. al., *Proc. Nat'l Acad. Sci. USA*, 88:10591–10595, 1991.
Schiaffino and Reggiani, *Physiol. Rev.*, 76:371–423, 1996.
Seidman and Seidman, *Basic Res. Cardiol.*, 93:13–16, 1998.
Semsarian et al., *Nature*, 400:576–581, 1999.
Shibasaki et al., *Nature*, 382:370–373, 1996.
Shub, *Cell*, 71(2):183–186, 1992.
Sigal et al., *J. Exp. Med.*, 173:619–628, 1991.
Srivastava et. al., *Cell*, 56:607–617, 1995.
Stewart and Young, Solid Phase Peptide Synthesis, 2d. ed., Pierce Chemical Co., 1984.
Stratford-Perricaudet and Perricaudet, In: *Human Gene Transfer*, O. Cohen-Haguenauer et al., eds., John Libbey Eurotext, France, pp. 51–61, 1991.
Stratford-Pernicaudet et al., *Hum. Gene. Ther.*, 1:241–256, 1990.
Sun et al., *Immunity*, 8:703–711, 1998.
Sussman et al., *Science*, 281:1690–1693, 1998.
Tam et al., *J. Am. Chem. Soc.*, 105:6442, 1983.
Temin, In: *Gene Transfer*, Kucherlapati R, ed., New York, Plenum Press, pp. 149–188, 1986.
Timmerman et al., *Nature*, 383:837–840, 1996.
Top et. al., *J. Infect. Dis.*, 124:155–160, 1971.
Tur-Kaspa et al., *Mol. Cell Biol.*, 6:716–718, 1986.
Uetsuki et al., *J. Biol. Chem.*, 264(10):5791–5798, 1989.
Varmus et al., *Cell*, 25:23–36, 1981.
Wagner et al., *Proc. Nat'l Acad. Sci. USA* 87(9):3410–3414, 1990.

Wakabayashi-Ito, et al.,*J. Biol. Chem.*, 269(47):29831–29837, 1994.
Wang et al., *Science*, 284:339–343, 1999.
Wong et al., *Gene*, 10:87–94, 1980.
Wu and Wu, *Adv. Drug Delivery Rev.*, 12:159–167, 1993.
Wu and Wu, *Biochemistry*, 27:887–892, 1988.
Wu and Wu, *J. Biol. Chem.*, 262:4429–4432, 1987.
Wu et al., *Genomics*, 4:560, 1989.
Yamauchi-Takihara, et. al., *Proc. Nat'l Acad. Sci. USA* 86(10):3504–3508, 1989.
Yang et al., *Proc. Nat'l Acad. Sci. USA*, 87:9568–9572, 1990.
Yang et al., *Mol. Cell. Biol.*, 17:5236–5243, 1997.
Youn et al., *Science*, 286:790–793, 1999.
Zelenin et al., *FEBS Lett.*, 280:94–96, 1991.
Zhang et al., *Circ. Res.*, 84:722–728, 1999.
Zhuo et al., *Proc. Nat'l Acad. Sci. USA*, 96:4650–4655, 1999.
Ziober and Kramer, *J. Biol. Chem.*, 271(37):22915–22, 1996.

What is claimed is:

1. An isolated polynucleotide encoding a myocardin polypeptide.
2. The isolated polynucleotide of claim 1, wherein the myocardin polypeptide comprises an amino acid sequence of SEQ ID NO:28.
3. The isolated polynucleotide of claim 2, wherein the polynucleotide sequence comprises SEQ ID NO:27.
4. The polynucleotide of claim 1, wherein said polynucleotide further comprises a promoter operable in eukaryotic cells.
5. An isolated nucleic acid segment comprising at least 1000 contiguous nucleotides of SEQ ID NO:27.
6. The isolated nucleic acid segment of claim 5, wherein said segment comprises 2000 contiguous nucleotides.
7. An expression cassette comprising a polynucleotide encoding a myocardin polypeptide operably linked to a regulatory sequence.
8. The expression cassette of claim 7, wherein the polynucleotide encodes a polypeptide having an amino acid sequence of SEQ ID NO:28.
9. The expression cassette of claim 8, wherein the polynucleotide sequence comprises SEQ ID NO:27.
10. The expression cassette of claim 7, wherein said regulatory sequence comprises a promoter heterologous to the coding sequence.
11. The expression cassette of claim 10, wherein said promoter is a tissue specific promoter.
12. The expression cassette of claim 11, wherein said promoter is a muscle specific promoter.
13. The expression cassette of claim 12, wherein said muscle specific promoter is myosin light chain-2 promoter, alpha actin promoter, troponin 1 promoter, $Na^+/Ca^{2+}$ exchanger promoter, dystrophin promoter, creatine kinase promoter, alpha7 integrin promoter, brain natriuretic peptide promoter, alpha B-crystallin/small heat shock protein promoter, alpha myosin heavy chain promoter or atrial natriuretic factor promoter.
14. The expression cassette of claim 12, wherein said muscle specific promoter is a cardiac muscle specific promoter.
15. The expression cassette of claim 14, wherein said cardiac muscle specific promoter is α-myosin heavy chain or ANF.
16. The expression cassette of claim 7, wherein said promoter is an inducible promoter.
17. The expression cassette of ciaim 7, wherein said promoter is a constitutive promoter.
18. The expression cassette of claim 7, wherein said expression cassette is contained in a gene delivery vector.
19. The expression cassette of claim 18, wherein said gene delivery vector is a viral vector.
20. The expression cassette of claim 19, wherein said viral vector is a retroviral vector, an adenoviral vector, an adeno-associated viral vector, a vaccina viral vector, a herpesviral vector, a polyoma viral construct or a Sindbis viral vector.
21. The expression cassette of claim 7, wherein said expression cassette further comprises a polyadenylation signal.
22. The expression cassette of claim 7, wherein said expression cassette further comprises a second polynucleotide encoding a second polypeptide.
23. The expression cassette of claim 22, wherein said second polypeptide is a cardiac transcription factor.
24. A transformed host cell comprising a polynucleotide encoding a myocardin polypeptide and a promoter heterologous to the polypeptide coding region, wherein said promoter directs expression of said myocardin polypeptide.
25. The transformed host cell of claim 24, further defined as prokaryotic host cell.
26. The transformed host cell of claim 24, further defined as eukaryotic host cell.
27. A method of using a host cell comprising an expression cassette comprising a polynucleotide encoding a myocardin polypeptide and a promoter active in said host cell comprising culturing the host cell under conditions suitable for the expression of the myocardin polypeptide.
28. A method of expressing a myocardin polypeptide in a host cell comprising introducing into said host cell an expression vector comprising a polynucleotide encoding a myocardin polypeptide, said polynucleotide being positioned under control of a promoter operable in said host cell.

* * * * *

UNITED STATES PATENT AND TRADEMARK OFFICE
CERTIFICATE OF CORRECTION

PATENT NO. : 6,962,798 B2 Page 1 of 1
DATED : November 8, 2005
INVENTOR(S) : Olson et al.

It is certified that error appears in the above-identified patent and that said Letters Patent is hereby corrected as shown below:

Column 156,
Line 6, delete "ciaim" and insert -- claim --.
Line 28, after "as" insert -- a --.
Line 30, after "as" insert -- an --.

Signed and Sealed this

Thirteenth Day of June, 2006

JON W. DUDAS
*Director of the United States Patent and Trademark Office*

SEQUENCE LISTING

<160> NUMBER OF SEQ ID NOS: 32

<210> SEQ ID NO 1
<211> LENGTH: 4959
<212> TYPE: DNA
<213> ORGANISM: Mus musculus
<220> FEATURE:
<221> NAME/KEY: CDS
<222> LOCATION: (641)..(3061)

<400> SEQUENCE: 1

```
ggaattcggc acgaggccac cctcagagga ggagggtcct gcctgctggg agttaattag      60
cctcgcgagc ggcgagggg gaggcgccag ttttctgggg acactggcgg ccactgtgcg      120
tcctcctacc caagggagct ccccaagagt tggatgaatt ctgggttgtt agctgctgtc     180
ctctgggctc ccgggagcca gtttctggtg gaaagcgggg cgcctggcca acgaccagcg     240
gcttgctgag actcaccatg acactcctgg ggtctgaaca ctctttgctg attagaagga     300
agttccgatc agtcttacag ttacggcttc aacagagaag gacccaggag cagctggcta     360
accaaggctt aataccgcca ctgaaaggtc caactgaatt ccatgacccg agaaaacaat     420
tggatagtgc caagactgaa gattccctga ggcgcaaggg cagaaacagg tccgaccgtg     480
ccagcctggt tactatgcac attctccaag cctccacggc agaaaggtcc attccaactg     540
ctcagatgaa gctcaaaaga gcccgccttg cagatgacct caatgagaag atcgctctcc     600
gccaaggccc ttggaactgg tggagaagaa cattctgccg atg gat tct tcc gtg      655
                                              Met Asp Ser Ser Val
                                                1               5 aaa gag gct ata aaa ggt act gag gtg agc ctc tcc aag gca gca gat      703
Lys Glu Ala Ile Lys Gly Thr Glu Val Ser Leu Ser Lys Ala Ala Asp
           10                  15                  20 gca ttc gcc ttt gag gat gac agc agt aga gat ggg ctc tct cca gat      751
Ala Phe Ala Phe Glu Asp Asp Ser Ser Arg Asp Gly Leu Ser Pro Asp
       25                  30                  35 cag gct agg agc gag gac ccc cag ggc tct aca gga tcc acc cca gac      799
Gln Ala Arg Ser Glu Asp Pro Gln Gly Ser Thr Gly Ser Thr Pro Asp
   40                  45                  50 atc aaa tcc act gag gct cct ctg gac aca atc cag gat ctc act cct      847
Ile Lys Ser Thr Glu Ala Pro Leu Asp Thr Ile Gln Asp Leu Thr Pro
55                  60                  65 ggc tca gaa agt gac aag aat gat gca gcc tcc cag cca ggc aac cag      895
Gly Ser Glu Ser Asp Lys Asn Asp Ala Ala Ser Gln Pro Gly Asn Gln
       70                  75                  80                  85 tca gac cct ggg aag cag gtt ctc ggc ccc ctc agc acc ccg att cct      943
Ser Asp Pro Gly Lys Gln Val Leu Gly Pro Leu Ser Thr Pro Ile Pro
               90                  95                  100 gtg cac act gct gta aag tcc aag tct ttg ggt gac agt aag aac cgc     991
Val His Thr Ala Val Lys Ser Lys Ser Leu Gly Asp Ser Lys Asn Arg
```

```
                105                   110                   115
cac aaa aag ccc aaa gac ccc aaa cca aag gtg aag aag ctc aaa tac      1039
His Lys Lys Pro Lys Asp Pro Lys Pro Lys Val Lys Lys Leu Lys Tyr
            120                   125                   130 cat cag tac atc ccc cca gac cag aag gca gag aag tct ccc cca ccc      1087
His Gln Tyr Ile Pro Pro Asp Gln Lys Ala Glu Lys Ser Pro Pro Pro
        135                   140                   145 atg gac tct gcc tat gcc cgg ctg ctc cag caa cag cag cta ttc ctg      1135
Met Asp Ser Ala Tyr Ala Arg Leu Leu Gln Gln Gln Gln Leu Phe Leu
150                   155                   160                   165 cag cta cag atc ctc agc cag cag cag caa cag cag caa cag cag          1183
Gln Leu Gln Ile Leu Ser Gln Gln Gln Gln Gln Gln Gln Gln Gln
                170                   175                   180 cag cag caa cag cag cag cag cag cag cag cgg ttc agc tac cct          1231
Gln Gln Gln Gln Gln Gln Gln Gln Gln Gln Arg Phe Ser Tyr Pro
            185                   190                   195 ggg atg cac caa aca cac ctc aaa gaa cca aat gaa cag atg gcc aga      1279
Gly Met His Gln Thr His Leu Lys Glu Pro Asn Glu Gln Met Ala Arg
            200                   205                   210 aat ccg aat cct tct tca aca cca ctg agc aat acc cct cta tcc cct      1327
Asn Pro Asn Pro Ser Ser Thr Pro Leu Ser Asn Thr Pro Leu Ser Pro
    215                   220                   225 gtc aaa aat agc att tct gga caa act ggt gtt tct tct ctc aaa cca      1375
Val Lys Asn Ser Ile Ser Gly Gln Thr Gly Val Ser Ser Leu Lys Pro
230                   235                   240                   245 ggc ccc ctc cca ccc aac ctg gat gat ctc aag gtg tca gag tta aga      1423
Gly Pro Leu Pro Pro Asn Leu Asp Asp Leu Lys Val Ser Glu Leu Arg
                250                   255                   260 caa cag ctt cga atc cgg ggc ttg cca gtg tca ggc acc aag aca gcg      1471
Gln Gln Leu Arg Ile Arg Gly Leu Pro Val Ser Gly Thr Lys Thr Ala
            265                   270                   275 ctg gtg gac cgg ctt cgt ccc ttc cag gat tgt gct ggc aac cct gtg      1519
Leu Val Asp Arg Leu Arg Pro Phe Gln Asp Cys Ala Gly Asn Pro Val
        280                   285                   290 ccc aac ttt ggg gac atc aca act gtc acc ttt cct gtc acg ccc aac      1567
Pro Asn Phe Gly Asp Ile Thr Thr Val Thr Phe Pro Val Thr Pro Asn
    295                   300                   305 acc ttg ccc agt tat cag tcc tcc ccg aca ggc ttc tac cac ttt ggc      1615
Thr Leu Pro Ser Tyr Gln Ser Ser Pro Thr Gly Phe Tyr His Phe Gly
310                   315                   320                   325 agc aca agc tcc agc cca ccc atc tcc ccc gcc tca tct gac ttg tcc      1663
Ser Thr Ser Ser Ser Pro Pro Ile Ser Pro Ala Ser Ser Asp Leu Ser
                330                   335                   340 gct gca ggg tcc ctg cca gac acc ttc acc gat gcg tca cct ggc ttc      1711
Ala Ala Gly Ser Leu Pro Asp Thr Phe Thr Asp Ala Ser Pro Gly Phe
            345                   350                   355 ggc ctg cac gca tct ccg gtg ccc gcc tgc acg gac gag agt ctg ctg      1759
Gly Leu His Ala Ser Pro Val Pro Ala Cys Thr Asp Glu Ser Leu Leu
        360                   365                   370 agc agc ctg aat ggg ggc tcg ggc ccc tcc gag cct gat ggg cta gac      1807
Ser Ser Leu Asn Gly Gly Ser Gly Pro Ser Glu Pro Asp Gly Leu Asp
    375                   380                   385 tct gag aag gac aag atg ctg gtg gag aag cag aaa gtg atc aac cag      1855
Ser Glu Lys Asp Lys Met Leu Val Glu Lys Gln Lys Val Ile Asn Gln
390                   395                   400                   405 ctc acc tgg aag ctg cgg caa gag cag cgg cag gtg gaa gag ctg aga      1903
Leu Thr Trp Lys Leu Arg Gln Glu Gln Arg Gln Val Glu Glu Leu Arg
                410                   415                   420 atg caa ctg cag aag cag aag agc agc tgc agc gac cag aag cca ctg      1951
```

```
Met Gln Leu Gln Lys Gln Lys Ser Ser Cys Ser Asp Gln Lys Pro Leu
        425                 430                 435 ccc ttc ttg gcc acc acc atc aaa cag gaa gat gtc tcc agc tgc ccc      1999
Pro Phe Leu Ala Thr Thr Ile Lys Gln Glu Asp Val Ser Ser Cys Pro
            440                 445                 450 ttc gca ccc cag cag gcg tct ggg aag gga cag ggc cac agc tct gac      2047
Phe Ala Pro Gln Gln Ala Ser Gly Lys Gly Gln Gly His Ser Ser Asp
        455                 460                 465 agt ccc cct ccg gct tgt gag acg gct cag ctg ctg cct cac tgt gtg      2095
Ser Pro Pro Pro Ala Cys Glu Thr Ala Gln Leu Leu Pro His Cys Val
470                 475                 480                 485 gag tcc tca ggt caa acc cat gta ctc tcg tcc acg ttt ctc agc ccc      2143
Glu Ser Ser Gly Gln Thr His Val Leu Ser Ser Thr Phe Leu Ser Pro
                490                 495                 500 cag tgc tcc cct cag cac tcg ccc ctg ggg ggc ctg aag agc ccg cag      2191
Gln Cys Ser Pro Gln His Ser Pro Leu Gly Gly Leu Lys Ser Pro Gln
            505                 510                 515 cac atc agc ctg cct cca tca ccc aac aac cat tac ttc ctg gct tcc      2239
His Ile Ser Leu Pro Pro Ser Pro Asn Asn His Tyr Phe Leu Ala Ser
        520                 525                 530 tct tcg gga gct cag aga gag aac cat ggg gtc tct tca ccc agc agc      2287
Ser Ser Gly Ala Gln Arg Glu Asn His Gly Val Ser Ser Pro Ser Ser
    535                 540                 545 agc caa ggg tgc gca cag atg act ggt tta caa tct tct gac aag gtg      2335
Ser Gln Gly Cys Ala Gln Met Thr Gly Leu Gln Ser Ser Asp Lys Val
550                 555                 560                 565 ggg cca acg ttt tca att cca tcc cca act ttt tct aag tca agt tca      2383
Gly Pro Thr Phe Ser Ile Pro Ser Pro Thr Phe Ser Lys Ser Ser Ser
                570                 575                 580 gca gtt tca gat atc acc cag ccc cca tcc tat gaa gat gca gtg aag      2431
Ala Val Ser Asp Ile Thr Gln Pro Pro Ser Tyr Glu Asp Ala Val Lys
            585                 590                 595 cag caa atg act cgg agt cag cag atg gac gaa ctc ctg gat gtc ctc      2479
Gln Gln Met Thr Arg Ser Gln Gln Met Asp Glu Leu Leu Asp Val Leu
        600                 605                 610 att gaa agt gga gaa atg cca gcc gat gcc agg gaa gat cat tca tgt      2527
Ile Glu Ser Gly Glu Met Pro Ala Asp Ala Arg Glu Asp His Ser Cys
    615                 620                 625 ctt cag aaa att cca aag atc cct ggg tcc tcc tgc agc cca act gcc      2575
Leu Gln Lys Ile Pro Lys Ile Pro Gly Ser Ser Cys Ser Pro Thr Ala
630                 635                 640                 645 atc ccc ccg aag ccc tcg gct tcc ttt gag cag gca tct tcg gga ggc      2623
Ile Pro Pro Lys Pro Ser Ala Ser Phe Glu Gln Ala Ser Ser Gly Gly
                650                 655                 660 cag atg gcc ttc gat cac tac gcc aac gac agt gac gaa cac ctg gaa      2671
Gln Met Ala Phe Asp His Tyr Ala Asn Asp Ser Asp Glu His Leu Glu
            665                 670                 675 gtc tta ttg aat tct cac agc ccc atc gga aag gtg agc gat gtt acc      2719
Val Leu Leu Asn Ser His Ser Pro Ile Gly Lys Val Ser Asp Val Thr
        680                 685                 690 ctc ctc aaa atc gga agc gag gag cct cct ttt gac agc atc atg gat      2767
Leu Leu Lys Ile Gly Ser Glu Glu Pro Pro Phe Asp Ser Ile Met Asp
    695                 700                 705 ggc ttc cca ggg aag gct gcg gaa gat ctc ttc agt gct cac gag ctc      2815
Gly Phe Pro Gly Lys Ala Ala Glu Asp Leu Phe Ser Ala His Glu Leu
710                 715                 720                 725 ttg cct ggg ccc ctc tcc ccg atg cat gca cag ttg tca cct cct tct      2863
Leu Pro Gly Pro Leu Ser Pro Met His Ala Gln Leu Ser Pro Pro Ser
                730                 735                 740
```

| | |
|---|---|
| gtg gac agc agt ggt ctg cag ctg agc ttc acg gaa tct cct tgg gaa<br>Val Asp Ser Ser Gly Leu Gln Leu Ser Phe Thr Glu Ser Pro Trp Glu<br>                745                      750                    755 | 2911 |
| aca atg gaa tgg ctg gac ctc act cca cct agt tcc acg cca ggc ttc<br>Thr Met Glu Trp Leu Asp Leu Thr Pro Pro Ser Ser Thr Pro Gly Phe<br>                760                      765                    770 | 2959 |
| agc aac ctt acc tcc agt ggg ccc agc att ttc aac atc gat ttt ctg<br>Ser Asn Leu Thr Ser Ser Gly Pro Ser Ile Phe Asn Ile Asp Phe Leu<br>                775                      780                    785 | 3007 |
| gat gtt aca gat ctt aat ctg aat tcc cct atg gat ctc cac tta cag<br>Asp Val Thr Asp Leu Asn Leu Asn Ser Pro Met Asp Leu His Leu Gln<br>790                      795                      800                    805 | 3055 |
| cag tgg taaacacccg aggtacaaga gctacgagag ctcagtggga attcaatgga<br>Gln Trp | 3111 |
| ggaaagcacg ataccggaaa tgtgtgttcc aaaagatgaa gggggaaaa tggggaggga | 3171 |
| aaaaaaaaaa cagcaacgga ggttttttgtg acaactaacc agaacaaaca gaagtcagct | 3231 |
| attaaaatat gtctaaatgt aatatctacc agcattcagt aactgttaat aacttcagtg | 3291 |
| atgcattcaa aaatgtgctt tgtcagaata agaatgccaa aaatgttttt tcgctgcctt | 3351 |
| atctcatacc agttttttttg ggtttttttt tgtttgtttg ttttttggtt tttttttttt | 3411 |
| tgtgtgtgtt gttatttggt tttcttttttg cccacagttt gtctcaggca atactgggac | 3471 |
| ataggctgac cccattagct tttgttatga atttactaaa ctttctgtgg aaggagaaca | 3531 |
| gagcctctgc cgcgggtgtg gggaagccat cctgtgcttg aggcagcaca cgtgtgtcca | 3591 |
| tcatcatcag tcagaagagc agggcctgtc tcacccaatc gagtccttaa dacagaataa | 3651 |
| tcagaatggt cagagggaca gaccaatcaa ttcccaggaa agcaaaagtg actcaatgtc | 3711 |
| ccttgactcc caaatggtcc cactggactg gtgatcactg gtgacaacta actagctttg | 3771 |
| tccagagaat ccacccagaa cacggtgctt tttagccagt agtccacctc tatgtgcatc | 3831 |
| agcaatgcat agcaggtgag aacttgaatc acagaaactt catgccatgg atggagactc | 3891 |
| ctgaggcgct caaatactac tacctctagt tccaaagact agagctagat gatcagaaag | 3951 |
| gcaactggag gcccagggag ccgtactggg acaagttaga attagagaac gatgtcattt | 4011 |
| aacattccga gaaagaaata accatgaatt gctattacag gagtaacaca cagggccagc | 4071 |
| ttctttttc ttctttttta ttttttctttt cttattgtga gcagagggaa ttcacctcag | 4131 |
| ttcatcttttc tctcagtact tttctttcaa gatatcaatc ctttatgact cttttgctttt | 4191 |
| taattctctc tctctctctc tctctctctc tctctcttttc tctcaaagga gaggtttcag | 4251 |
| ttctaacaag ctaccatagt cctattaaag ccatttttttt ttttagaata ttaaaagtcc | 4311 |
| aaactctctt gccaaactct ttcttcacat gcgcattggc tgaaaacaga atttacaaga | 4371 |
| atttctttag gaagaaactg gggatgtggc ccattggtca caagtttttt ttgtttgttt | 4431 |
| ttgttttttgt ttcaattctt gtttgattta tggacaatct ttggtttgta ttgctctgga | 4491 |
| gaaattggaa atcattgcag agtgaagata aatcagggca ccatgtatag tagagaatgt | 4551 |
| ttcagtagtt ttccaaacga gaacacaatt gcacactgta acaacagga gtgtgaagga | 4611 |
| ccacagtctt gaggagttct tgttgccctg tgtttggtga aggcgttggg gaccgaggaa | 4671 |
| gacaacatac agtttggcca aggctctcag aggcttgctg tggcgccaat tcaagtatta | 4731 |
| caatgttgca tgctgtagaa agtagctgtt gctgttgttt tgttttgttt taatttaagt | 4791 |
| caccaaggca ctgtttttatt cttttgtaaa aaaaaaaaa gttcactgtg cacttataga | 4851 |
| gaaaataatc aacaatgttg tgaatttttg agaagacttt ttttttttttg ataaaccaaa | 4911 |

-continued gatttagaaa tcattccatt gtcaactttgt aaaaaaaaaa aaaaaaa                                    4959

<210> SEQ ID NO 2
<211> LENGTH: 807
<212> TYPE: PRT
<213> ORGANISM: Mus musculus

<400> SEQUENCE: 2

Met Asp Ser Ser Val Lys Glu Ala Ile Lys Gly Thr Glu Val Ser Leu
  1               5                  10                  15

Ser Lys Ala Ala Asp Ala Phe Ala Phe Glu Asp Asp Ser Ser Arg Asp
             20                  25                  30

Gly Leu Ser Pro Asp Gln Ala Arg Ser Glu Asp Pro Gln Gly Ser Thr
         35                  40                  45

Gly Ser Thr Pro Asp Ile Lys Ser Thr Glu Ala Pro Leu Asp Thr Ile
     50                  55                  60

Gln Asp Leu Thr Pro Gly Ser Glu Ser Asp Lys Asn Asp Ala Ala Ser
 65                  70                  75                  80

Gln Pro Gly Asn Gln Ser Asp Pro Gly Lys Gln Val Leu Gly Pro Leu
                 85                  90                  95

Ser Thr Pro Ile Pro Val His Thr Ala Val Lys Ser Lys Ser Leu Gly
            100                 105                 110

Asp Ser Lys Asn Arg His Lys Lys Pro Lys Asp Pro Lys Pro Lys Val
        115                 120                 125

Lys Lys Leu Lys Tyr His Gln Tyr Ile Pro Pro Asp Gln Lys Ala Glu
130                 135                 140

Lys Ser Pro Pro Met Asp Ser Ala Tyr Ala Arg Leu Leu Gln Gln
145                 150                 155                 160

Gln Gln Leu Phe Leu Gln Leu Gln Ile Leu Ser Gln Gln Gln Gln
                165                 170                 175

Gln Gln Gln Gln Gln Gln Gln Gln Gln Gln Gln Gln Gln Gln
            180                 185                 190

Arg Phe Ser Tyr Pro Gly Met His Gln Thr His Leu Lys Glu Pro Asn
        195                 200                 205

Glu Gln Met Ala Arg Asn Pro Asn Pro Ser Ser Thr Pro Leu Ser Asn
    210                 215                 220

Thr Pro Leu Ser Pro Val Lys Asn Ser Ile Ser Gly Gln Thr Gly Val
225                 230                 235                 240

Ser Ser Leu Lys Pro Gly Pro Leu Pro Pro Asn Leu Asp Asp Leu Lys
                245                 250                 255

Val Ser Glu Leu Arg Gln Gln Leu Arg Ile Arg Gly Leu Pro Val Ser
            260                 265                 270

Gly Thr Lys Thr Ala Leu Val Asp Arg Leu Arg Pro Phe Gln Asp Cys
        275                 280                 285

Ala Gly Asn Pro Val Pro Asn Phe Gly Asp Ile Thr Thr Val Thr Phe
    290                 295                 300

Pro Val Thr Pro Asn Thr Leu Pro Ser Tyr Gln Ser Ser Pro Thr Gly
305                 310                 315                 320

Phe Tyr His Phe Gly Ser Thr Ser Ser Pro Pro Ile Ser Pro Ala
                325                 330                 335

Ser Ser Asp Leu Ser Ala Ala Gly Ser Leu Pro Asp Thr Phe Thr Asp
            340                 345                 350

Ala Ser Pro Gly Phe Gly Leu His Ala Ser Pro Val Pro Ala Cys Thr
        355                 360                 365

```
Asp Glu Ser Leu Leu Ser Ser Leu Asn Gly Gly Ser Gly Pro Ser Glu
    370                 375                 380

Pro Asp Gly Leu Asp Ser Glu Lys Asp Lys Met Leu Val Glu Lys Gln
385                 390                 395                 400

Lys Val Ile Asn Gln Leu Thr Trp Lys Leu Arg Gln Glu Gln Arg Gln
            405                 410                 415

Val Glu Glu Leu Arg Met Gln Leu Gln Lys Gln Lys Ser Ser Cys Ser
        420                 425                 430

Asp Gln Lys Pro Leu Pro Phe Leu Ala Thr Thr Ile Lys Gln Glu Asp
        435                 440                 445

Val Ser Ser Cys Pro Phe Ala Pro Gln Gln Ala Ser Gly Lys Gly Gln
    450                 455                 460

Gly His Ser Ser Asp Ser Pro Pro Ala Cys Glu Thr Ala Gln Leu
465                 470                 475                 480

Leu Pro His Cys Val Glu Ser Ser Gly Gln Thr His Val Leu Ser Ser
                485                 490                 495

Thr Phe Leu Ser Pro Gln Cys Ser Pro Gln His Ser Pro Leu Gly Gly
            500                 505                 510

Leu Lys Ser Pro Gln His Ile Ser Leu Pro Pro Ser Pro Asn Asn His
        515                 520                 525

Tyr Phe Leu Ala Ser Ser Gly Ala Gln Arg Glu Asn His Gly Val
    530                 535                 540

Ser Ser Pro Ser Ser Ser Gln Gly Cys Ala Gln Met Thr Gly Leu Gln
545                 550                 555                 560

Ser Ser Asp Lys Val Gly Pro Thr Phe Ser Ile Pro Ser Pro Thr Phe
            565                 570                 575

Ser Lys Ser Ser Ser Ala Val Ser Asp Ile Thr Gln Pro Pro Ser Tyr
        580                 585                 590

Glu Asp Ala Val Lys Gln Gln Met Thr Arg Ser Gln Gln Met Asp Glu
        595                 600                 605

Leu Leu Asp Val Leu Ile Glu Ser Gly Glu Met Pro Ala Asp Ala Arg
    610                 615                 620

Glu Asp His Ser Cys Leu Gln Lys Ile Pro Lys Ile Pro Gly Ser Ser
625                 630                 635                 640

Cys Ser Pro Thr Ala Ile Pro Pro Lys Pro Ser Ala Ser Phe Glu Gln
            645                 650                 655

Ala Ser Ser Gly Gly Gln Met Ala Phe Asp His Tyr Ala Asn Asp Ser
        660                 665                 670

Asp Glu His Leu Glu Val Leu Leu Asn Ser His Ser Pro Ile Gly Lys
    675                 680                 685

Val Ser Asp Val Thr Leu Leu Lys Ile Gly Ser Glu Pro Pro Phe
    690                 695                 700

Asp Ser Ile Met Asp Gly Phe Pro Gly Lys Ala Ala Glu Asp Leu Phe
705                 710                 715                 720

Ser Ala His Glu Leu Leu Pro Gly Pro Leu Ser Pro Met His Ala Gln
            725                 730                 735

Leu Ser Pro Pro Ser Val Asp Ser Ser Gly Leu Gln Leu Ser Phe Thr
        740                 745                 750

Glu Ser Pro Trp Glu Thr Met Glu Trp Leu Asp Leu Thr Pro Pro Ser
        755                 760                 765

Ser Thr Pro Gly Phe Ser Asn Leu Thr Ser Ser Gly Pro Ser Ile Phe
    770                 775                 780

Asn Ile Asp Phe Leu Asp Val Thr Asp Leu Asn Leu Asn Ser Pro Met
```

-continued

```
            785                 790                 795                 800
Asp Leu His Leu Gln Gln Trp
                805

<210> SEQ ID NO 3
<211> LENGTH: 3907
<212> TYPE: DNA
<213> ORGANISM: Mus musculus
<220> FEATURE:
<221> NAME/KEY: CDS
<222> LOCATION: (5)..(2083)

<400> SEQUENCE: 3 ccaa ggg atc atg ccg cct ttg aaa agt cca gcc gca ttt cat gag cag        49
     Gly Ile Met Pro Pro Leu Lys Ser Pro Ala Ala Phe His Glu Gln
      1               5                  10                  15 aga agg agc ttg gag cgg gcc agg aca gag gac tat ctc aaa cgg aag         97
Arg Arg Ser Leu Glu Arg Ala Arg Thr Glu Asp Tyr Leu Lys Arg Lys
         20                  25                  30 att cgt tcc cgg ccg gag aga tcg gag ctg gtc agg atg cac att ttg        145
Ile Arg Ser Arg Pro Glu Arg Ser Glu Leu Val Arg Met His Ile Leu
 35                  40                  45 gaa gag acc tcg gct gag cca tcc ctc cag gcc aag cag ctg aag ctg        193
Glu Glu Thr Ser Ala Glu Pro Ser Leu Gln Ala Lys Gln Leu Lys Leu
         50                  55                  60 aag aga gcc aga cta gcc gat gac ctc aat gag aag att gca cag agg        241
Lys Arg Ala Arg Leu Ala Asp Asp Leu Asn Glu Lys Ile Ala Gln Arg
 65                  70                  75 cct ggc ccc atg gag ctg gtg gag aag aac atc ctt cct gtt gag tcc        289
Pro Gly Pro Met Glu Leu Val Glu Lys Asn Ile Leu Pro Val Glu Ser
         80                  85                  90                  95 agc ctg aag gaa gcc atc att gtg ggc cag gtg aac tat ccc aaa gta        337
Ser Leu Lys Glu Ala Ile Ile Val Gly Gln Val Asn Tyr Pro Lys Val
                100                 105                 110 gca gac agc tct tcc ttc gat gag gac agc agc gat gcc tta tcc ccc        385
Ala Asp Ser Ser Ser Phe Asp Glu Asp Ser Ser Asp Ala Leu Ser Pro
            115                 120                 125 gag cag cct gcc agc cat gag tcc cag ggt tct gtg ccg tca ccc ctg        433
Glu Gln Pro Ala Ser His Glu Ser Gln Gly Ser Val Pro Ser Pro Leu
        130                 135                 140 gag gcc cga gtc agc gaa cca ctg ctc agt gcc acc tct gca tcc ccc        481
Glu Ala Arg Val Ser Glu Pro Leu Leu Ser Ala Thr Ser Ala Ser Pro
    145                 150                 155 acc cag gtt gtg tct caa ctt ccg atg ggc cgg gat tcc aga gaa atg        529
Thr Gln Val Val Ser Gln Leu Pro Met Gly Arg Asp Ser Arg Glu Met
160                 165                 170                 175 ctt ttc ctg gca gag cag cct cct ctg cct ccc cca cct ctg ctg cct        577
Leu Phe Leu Ala Glu Gln Pro Pro Leu Pro Pro Pro Pro Leu Leu Pro
                180                 185                 190 ccc agc ctc acc aat gga acc act atc ccc act gcc aag tcc acc ccc        625
Pro Ser Leu Thr Asn Gly Thr Thr Ile Pro Thr Ala Lys Ser Thr Pro
            195                 200                 205 aca ctc att aag caa agc caa ccc aag tct gcc agt gag aag tca cag        673
Thr Leu Ile Lys Gln Ser Gln Pro Lys Ser Ala Ser Glu Lys Ser Gln
        210                 215                 220 cgc agc aag aag gcc aag gag ctg aag cca aag gtg aag aag ctc aag        721
Arg Ser Lys Lys Ala Lys Glu Leu Lys Pro Lys Val Lys Lys Leu Lys
    225                 230                 235 tac cac cag tac atc ccc ccg gac cag aag cag gac agg ggg gca ccc        769
Tyr His Gln Tyr Ile Pro Pro Asp Gln Lys Gln Asp Arg Gly Ala Pro
240                 245                 250                 255
```

```
ccc atg gac tca tcc tac gcc aag atc ctg cag cag cag cag ctc ttc      817
Pro Met Asp Ser Ser Tyr Ala Lys Ile Leu Gln Gln Gln Gln Leu Phe
            260                 265                 270 ctc cag ctg cag atc ctc aac cag cag cag cag cac cac aac tac          865
Leu Gln Leu Gln Ile Leu Asn Gln Gln Gln Gln His His Asn Tyr
    275                 280                 285 cag gcc atc ctg cct gcc ccg cca aag tca gca ggc gag gcc ctg gga      913
Gln Ala Ile Leu Pro Ala Pro Pro Lys Ser Ala Gly Glu Ala Leu Gly
            290                 295                 300 agc agc ggg acc ccc cca gta cgc agc ctc tcc act acc aat agc agc      961
Ser Ser Gly Thr Pro Pro Val Arg Ser Leu Ser Thr Thr Asn Ser Ser
305                 310                 315 tcc agc tcg ggc gcc cct ggg ccc tgt ggg ctg gca cgt cag aac agc     1009
Ser Ser Ser Gly Ala Pro Gly Pro Cys Gly Leu Ala Arg Gln Asn Ser
320                 325                 330                 335 acc tca ctg act ggc aag ccg gga gcc ctg ccg gcc aac ctg gac gac     1057
Thr Ser Leu Thr Gly Lys Pro Gly Ala Leu Pro Ala Asn Leu Asp Asp
                340                 345                 350 atg aag gtg gca gag ctg aag cag gag ctg aag ttg cga tca ctg cct     1105
Met Lys Val Ala Glu Leu Lys Gln Glu Leu Lys Leu Arg Ser Leu Pro
            355                 360                 365 gtc tcg ggc acc aaa act gag ctg att gag cgc ctt cga gcc tat caa     1153
Val Ser Gly Thr Lys Thr Glu Leu Ile Glu Arg Leu Arg Ala Tyr Gln
        370                 375                 380 gac caa atc agc cct gtg cca gga gcc ccc aag gcc cct gcc gcc acc     1201
Asp Gln Ile Ser Pro Val Pro Gly Ala Pro Lys Ala Pro Ala Ala Thr
385                 390                 395 tct atc ctg cac aag gct ggc gag gtg gtg gta gcc ttc cca gcg gcc     1249
Ser Ile Leu His Lys Ala Gly Glu Val Val Val Ala Phe Pro Ala Ala
400                 405                 410                 415 cgg ctg agc acg ggg cca gcc ctg gtg gca gca ggc ctg gct cca gct     1297
Arg Leu Ser Thr Gly Pro Ala Leu Val Ala Ala Gly Leu Ala Pro Ala
                420                 425                 430 gag gtg gtg gtg gcc acg gtg gcc agc agt ggg gtg gtg aag ttt ggc     1345
Glu Val Val Val Ala Thr Val Ala Ser Ser Gly Val Val Lys Phe Gly
            435                 440                 445 agc acg ggc tcc acg ccc ccc gtg tct ccc acc ccc tcg gag cgc tca     1393
Ser Thr Gly Ser Thr Pro Pro Val Ser Pro Thr Pro Ser Glu Arg Ser
        450                 455                 460 ctg ctc agc acg ggc gat gaa aac tcc acc ccc ggg gac acc ttt ggt     1441
Leu Leu Ser Thr Gly Asp Glu Asn Ser Thr Pro Gly Asp Thr Phe Gly
    465                 470                 475 gag atg gtg aca tca cct ctg acg cag ctg acc ctg cag gcc tcg cca     1489
Glu Met Val Thr Ser Pro Leu Thr Gln Leu Thr Leu Gln Ala Ser Pro
480                 485                 490                 495 ctg cag atc ctc gtg aag gag gag ggc ccc cgg gcc ggg tcc tgt tgc     1537
Leu Gln Ile Leu Val Lys Glu Glu Gly Pro Arg Ala Gly Ser Cys Cys
                500                 505                 510 ctg agc cct ggg ggg cgg gcg gag cta gag ggg cgc gac aag gac cag     1585
Leu Ser Pro Gly Gly Arg Ala Glu Leu Glu Gly Arg Asp Lys Asp Gln
            515                 520                 525 atg ctg cag gag aaa gac aag cag atc gag gcg ctg acg cgc atg ctc     1633
Met Leu Gln Glu Lys Asp Lys Gln Ile Glu Ala Leu Thr Arg Met Leu
        530                 535                 540 cgg cag aag cag cag ctg gtg gag cgg ctc aag ctg cag ctg gag cag     1681
Arg Gln Lys Gln Gln Leu Val Glu Arg Leu Lys Leu Gln Leu Glu Gln
545                 550                 555 gag aag cga gcc cag cag ccc gcc ccc gcc ccc gcc ccc ctc ggc acc     1729
Glu Lys Arg Ala Gln Gln Pro Ala Pro Ala Pro Ala Pro Leu Gly Thr
```

-continued

| | | | | | | | | | | | | | | | | |
|---|---|---|---|---|---|---|---|---|---|---|---|---|---|---|---|---|
| | 560 | | | | 565 | | | | 570 | | | | 575 | | | |
| ccc | gtg | aag | cag | gag | aac | agc | ttc | tcc | agc | tgc | cag | ctg | agc | cag | cag | 1777 |
| Pro | Val | Lys | Gln | Glu | Asn | Ser | Phe | Ser | Ser | Cys | Gln | Leu | Ser | Gln | Gln | |
| | | | | 580 | | | | | 585 | | | | | 590 | | |
| ccc | ctg | ggc | ccc | gct | cac | cca | ttc | aac | ccc | agc | ctg | gcg | gcc | cca | gcc | 1825 |
| Pro | Leu | Gly | Pro | Ala | His | Pro | Phe | Asn | Pro | Ser | Leu | Ala | Ala | Pro | Ala | |
| | | | 595 | | | | | 600 | | | | | 605 | | | |
| acc | aac | cac | ata | gac | cct | tgt | gct | gtg | gcc | ccg | ggg | ccc | ccg | tcc | gtg | 1873 |
| Thr | Asn | His | Ile | Asp | Pro | Cys | Ala | Val | Ala | Pro | Gly | Pro | Pro | Ser | Val | |
| | | 610 | | | | | 615 | | | | | 620 | | | | |
| gtg | gtg | aag | cag | gaa | gcc | ttg | cag | cct | gag | ccc | gag | ccg | gtc | ccc | gcc | 1921 |
| Val | Val | Lys | Gln | Glu | Ala | Leu | Gln | Pro | Glu | Pro | Glu | Pro | Val | Pro | Ala | |
| | 625 | | | | | 630 | | | | | 635 | | | | | |
| ccc | cag | ttg | ctt | ctg | ggg | cct | cag | ggc | ccc | agc | ctc | atc | aag | ggg | gtt | 1969 |
| Pro | Gln | Leu | Leu | Leu | Gly | Pro | Gln | Gly | Pro | Ser | Leu | Ile | Lys | Gly | Val | |
| 640 | | | | | 645 | | | | | 650 | | | | | 655 | |
| gca | cct | ccc | acc | ctc | atc | acc | gac | tcc | aca | ggg | acc | cac | ctt | gtc | ctc | 2017 |
| Ala | Pro | Pro | Thr | Leu | Ile | Thr | Asp | Ser | Thr | Gly | Thr | His | Leu | Val | Leu | |
| | | | | 660 | | | | | 665 | | | | | 670 | | |
| acc | gtg | acc | aat | aag | aat | gca | gac | agc | cct | ggc | ctg | tcc | agt | ggg | agc | 2065 |
| Thr | Val | Thr | Asn | Lys | Asn | Ala | Asp | Ser | Pro | Gly | Leu | Ser | Ser | Gly | Ser | |
| | | | 675 | | | | | 680 | | | | | 685 | | | |
| ccc | cag | cag | ccc | tcg | tcc | cagcctggct | | ctccagcgcc | | tgccccctct | | | | | | 2113 |
| Pro | Gln | Gln | Pro | Ser | Ser | | | | | | | | | | | |
| | | 690 | | | | | | | | | | | | | | |

| | | |
|---|---|---|
| gcccagatgg acctggagca cccactgcag cccctctttg gaccccccac ttctctgctg | | 2173 |
| aagaaggaac cacctggcta tgaggaagcc atgagccagc agcccaaaca gcaggaaaat | | 2233 |
| ggttcctcaa gccagcagat ggacgacctg tttgacattc tcattcagag cggagaaatt | | 2293 |
| tcagcagatt tcaaggagcc gccatccctg ccagggaagg agaagccatc cccgaagaca | | 2353 |
| gtctgtgggt ccccctggc agcacagcca tcaccttctg ctgagctccc ccaggctgcc | | 2413 |
| ccacctcctc caggctcacc ctccctccct ggacgcctgg aggacttcct ggagagcagc | | 2473 |
| acggggctgc ccctgctgac cagtgggcat gacgggccag agccccttc cctcattgac | | 2533 |
| gacctccata gccagatgct gagcagcact gccatcctgg accacccccc gtcacccatg | | 2593 |
| gacacctcgg aattgcactt tgttcctgag cccagcagca ccatgggcct ggacctggct | | 2653 |
| gatggccacc tggacagcat ggactggctg agctgtcgt caggtggtcc cgtgctgagc | | 2713 |
| ctagcccccc tcagcaccac agcccccagc ctcttctcca cagacttcct cgatggccat | | 2773 |
| gatttgcagc tgcactggga ttcctgcttg tagctctctg gctcaagacg gggtggggaa | | 2833 |
| ggggctggga gccagggtac tccaatgcgt ggctctcctg cgtgattcgg cctctccaca | | 2893 |
| tggttgtgag tcttgacaat cacagcccct gcttttcccc ttccctggga ggctagaaca | | 2953 |
| gagaagccct tactcctggt tcagtgccac gcagggcaga ggagagcagc tgtcaagaag | | 3013 |
| cagccctggc tctcacgctg gggttttgga cacacggtca gggtcagggc catttcagct | | 3073 |
| tgacctcctt ttttgaggtc agggggcact gtctgtctgg ctacaatttg gctaaggtag | | 3133 |
| gtgaagcctg gccaggcggg aggcttctct tctgacccag gctgagaca ggttaagggg | | 3193 |
| tgaatctcct tccttctct ccctgctttg ctgtgaaggg agaaattagc ctgggcctct | | 3253 |
| accccctatt ccctgtgtct gccaacccca ggatcccagg gctccctgcc attttagtgt | | 3313 |
| cttggtgtag tgtaaccatt tagtggttgg tggcaacaat tttatgtaca ggtgtatata | | 3373 |
| cctctatatt atatatcgac atacatatat attttgggg ggggcggac aggagatggg | | 3433 |
| tgcaactccc tcccatccta ctctcacaga agggcctgga tgcaaggtta cccttgagct | | 3493 |

-continued

```
gtgtgccaca gtctggtgcc cagtctggca tgcagctacc caggcccacc catcacgtgt      3553
gattgacatg taggtaccct gccacggcct atgccccacc tgccctgctt cctggctcct      3613
tatcagtgcc atgagggcag aggtgctacc tggccttcct gccaggagct ctccacccac      3673
tcacattccg tccccgccgc ctcactgcag ccagcgtggt cctaggacag gaggagcttc      3733
gggcccagct tcaccctgcg gtggggctga ggggtggcca tctcctgccc tgggccact       3793 ggcttcacat tctgggctga ctcataggg agtagggtg gagtcaccaa aaccagtgct        3853
gggacaaaga tggggaaggt gtgtgaactt tttaaaataa acacaaaaac acag            3907
```

<210> SEQ ID NO 4
<211> LENGTH: 693
<212> TYPE: PRT
<213> ORGANISM: Mus musculus

<400> SEQUENCE: 4

```
Gly Ile Met Pro Pro Leu Lys Ser Pro Ala Ala Phe His Glu Gln Arg
 1               5                  10                  15

Arg Ser Leu Glu Arg Ala Arg Thr Glu Asp Tyr Leu Lys Arg Lys Ile
            20                  25                  30

Arg Ser Arg Pro Glu Arg Ser Glu Leu Val Arg Met His Ile Leu Glu
        35                  40                  45

Glu Thr Ser Ala Glu Pro Ser Leu Gln Ala Lys Gln Leu Lys Leu Lys
    50                  55                  60

Arg Ala Arg Leu Ala Asp Asp Leu Asn Glu Lys Ile Ala Gln Arg Pro
65                  70                  75                  80

Gly Pro Met Glu Leu Val Glu Lys Asn Ile Leu Pro Val Glu Ser Ser
                85                  90                  95

Leu Lys Glu Ala Ile Ile Val Gly Gln Val Asn Tyr Pro Lys Val Ala
            100                 105                 110

Asp Ser Ser Ser Phe Asp Glu Asp Ser Ser Asp Ala Leu Ser Pro Glu
        115                 120                 125

Gln Pro Ala Ser His Glu Ser Gln Gly Ser Val Pro Ser Pro Leu Glu
    130                 135                 140

Ala Arg Val Ser Glu Pro Leu Leu Ser Ala Thr Ser Ala Ser Pro Thr
145                 150                 155                 160

Gln Val Val Ser Gln Leu Pro Met Gly Arg Asp Ser Arg Glu Met Leu
                165                 170                 175

Phe Leu Ala Glu Gln Pro Pro Leu Pro Pro Pro Leu Leu Pro Pro
            180                 185                 190

Ser Leu Thr Asn Gly Thr Thr Ile Pro Thr Ala Lys Ser Thr Pro Thr
        195                 200                 205

Leu Ile Lys Gln Ser Gln Pro Lys Ser Ala Ser Glu Lys Ser Gln Arg
    210                 215                 220

Ser Lys Lys Ala Lys Glu Leu Lys Pro Lys Val Lys Lys Leu Lys Tyr
225                 230                 235                 240

His Gln Tyr Ile Pro Pro Asp Gln Lys Gln Asp Arg Gly Ala Pro Pro
                245                 250                 255

Met Asp Ser Ser Tyr Ala Lys Ile Leu Gln Gln Gln Gln Leu Phe Leu
            260                 265                 270

Gln Leu Gln Ile Leu Asn Gln Gln Gln Gln His His Asn Tyr Gln
        275                 280                 285

Ala Ile Leu Pro Ala Pro Pro Lys Ser Ala Gly Glu Ala Leu Gly Ser
    290                 295                 300
```

-continued

```
Ser Gly Thr Pro Pro Val Arg Ser Leu Ser Thr Thr Asn Ser Ser Ser
305                 310                 315                 320

Ser Ser Gly Ala Pro Gly Pro Cys Gly Leu Ala Arg Gln Asn Ser Thr
            325                 330                 335

Ser Leu Thr Gly Lys Pro Gly Ala Leu Pro Ala Asn Leu Asp Asp Met
            340                 345                 350

Lys Val Ala Glu Leu Lys Gln Glu Leu Lys Leu Arg Ser Leu Pro Val
            355                 360                 365

Ser Gly Thr Lys Thr Glu Leu Ile Glu Arg Leu Arg Ala Tyr Gln Asp
370                 375                 380

Gln Ile Ser Pro Val Pro Gly Ala Pro Lys Ala Pro Ala Ala Thr Ser
385                 390                 395                 400

Ile Leu His Lys Ala Gly Glu Val Val Val Ala Phe Pro Ala Ala Arg
            405                 410                 415

Leu Ser Thr Gly Pro Ala Leu Val Ala Ala Gly Leu Ala Pro Ala Glu
            420                 425                 430

Val Val Val Ala Thr Val Ala Ser Ser Gly Val Val Lys Phe Gly Ser
            435                 440                 445

Thr Gly Ser Thr Pro Pro Val Ser Pro Thr Pro Ser Glu Arg Ser Leu
450                 455                 460

Leu Ser Thr Gly Asp Glu Asn Ser Thr Pro Gly Asp Thr Phe Gly Glu
465                 470                 475                 480

Met Val Thr Ser Pro Leu Thr Gln Leu Thr Leu Gln Ala Ser Pro Leu
            485                 490                 495

Gln Ile Leu Val Lys Glu Gly Pro Arg Ala Gly Ser Cys Cys Leu
            500                 505                 510

Ser Pro Gly Gly Arg Ala Glu Leu Glu Gly Arg Asp Lys Asp Gln Met
            515                 520                 525

Leu Gln Glu Lys Asp Lys Gln Ile Glu Ala Leu Thr Arg Met Leu Arg
530                 535                 540

Gln Lys Gln Gln Leu Val Glu Arg Leu Lys Leu Gln Leu Glu Gln Glu
545                 550                 555                 560

Lys Arg Ala Gln Gln Pro Ala Pro Ala Pro Leu Gly Thr Pro
            565                 570                 575

Val Lys Gln Glu Asn Ser Phe Ser Ser Cys Gln Leu Ser Gln Gln Pro
            580                 585                 590

Leu Gly Pro Ala His Pro Phe Asn Pro Ser Leu Ala Ala Pro Ala Thr
            595                 600                 605

Asn His Ile Asp Pro Cys Ala Val Ala Pro Gly Pro Pro Ser Val Val
610                 615                 620

Val Lys Gln Glu Ala Leu Gln Pro Glu Pro Glu Pro Val Pro Ala Pro
625                 630                 635                 640

Gln Leu Leu Leu Gly Pro Gln Gly Pro Ser Leu Ile Lys Gly Val Ala
            645                 650                 655

Pro Pro Thr Leu Ile Thr Asp Ser Thr Gly Thr His Leu Val Leu Thr
            660                 665                 670

Val Thr Asn Lys Asn Ala Asp Ser Pro Gly Leu Ser Ser Gly Ser Pro
            675                 680                 685

Gln Gln Pro Ser Ser
    690
```

<210> SEQ ID NO 5
<211> LENGTH: 35

```
<212> TYPE: PRT
<213> ORGANISM: Mus musculus

<400> SEQUENCE: 5

Leu Glu Lys Met Lys Val Ser Asp Leu Lys Gln His Leu Lys Arg Arg
 1               5                  10                  15

Asn Leu Pro Val Ser Gly Pro Lys Pro His Leu Ile Glu Arg Leu Lys
            20                  25                  30

Pro Tyr Leu
        35

<210> SEQ ID NO 6
<211> LENGTH: 6459
<212> TYPE: DNA
<213> ORGANISM: Mus musculus
<220> FEATURE:
<221> NAME/KEY: CDS
<222> LOCATION: (1)..(1053)

<400> SEQUENCE: 6 cag act tca cca caa gca gga atg cag act cag cct cag ata gca act      48
Gln Thr Ser Pro Gln Ala Gly Met Gln Thr Gln Pro Gln Ile Ala Thr
 1               5                  10                  15 gct gca caa ata cca act gct gcc ttg gcc tca ggc ttg gcc cca act      96
Ala Ala Gln Ile Pro Thr Ala Ala Leu Ala Ser Gly Leu Ala Pro Thr
            20                  25                  30 gta cct cag aca caa gac acg ttc ccg cag cat gtg ctc agt cag cct     144
Val Pro Gln Thr Gln Asp Thr Phe Pro Gln His Val Leu Ser Gln Pro
        35                  40                  45 caa caa gtc aga aag gtt ttc aca aac tca gca tca tca aat aca gtt     192
Gln Gln Val Arg Lys Val Phe Thr Asn Ser Ala Ser Ser Asn Thr Val
    50                  55                  60 ctt cca tat cag aga cat cct gcc cca gct gtc cag cag ccc ttt atc     240
Leu Pro Tyr Gln Arg His Pro Ala Pro Ala Val Gln Gln Pro Phe Ile
65                  70                  75                  80 aat aag gcc tcc aac agt gtt ctt caa tcc aga aat gct ccg ctt cca     288
Asn Lys Ala Ser Asn Ser Val Leu Gln Ser Arg Asn Ala Pro Leu Pro
                85                  90                  95 tcc ctg caa aat gga cct aac aca ccc aac aag cct agt tca ccc ccg     336
Ser Leu Gln Asn Gly Pro Asn Thr Pro Asn Lys Pro Ser Ser Pro Pro
            100                 105                 110 cca ccc cag caa ttt gtc gtc cag cac tct cta ttt ggg agt cca gtc     384
Pro Pro Gln Gln Phe Val Val Gln His Ser Leu Phe Gly Ser Pro Val
        115                 120                 125 gcc aag aca aaa gat ccc ccc cgc tat gag gag gcc atc aag cag aca     432
Ala Lys Thr Lys Asp Pro Pro Arg Tyr Glu Glu Ala Ile Lys Gln Thr
    130                 135                 140 cgc agc aca cag gcc cct ctg cca gag att tcc aac gct cac agt cag     480
Arg Ser Thr Gln Ala Pro Leu Pro Glu Ile Ser Asn Ala His Ser Gln
145                 150                 155                 160 cag atg gat gac ctc ttt gat atc ctc att aag agt gga gag atc tcc     528
Gln Met Asp Asp Leu Phe Asp Ile Leu Ile Lys Ser Gly Glu Ile Ser
                165                 170                 175 ctc ccc ata aaa gaa gaa cct tct cct att tcc aaa atg aga cca gtg     576
Leu Pro Ile Lys Glu Glu Pro Ser Pro Ile Ser Lys Met Arg Pro Val
            180                 185                 190 aca gcc agc atc acc aca atg cca gtg aat aca gtg gtg tcc cgg cca     624
Thr Ala Ser Ile Thr Thr Met Pro Val Asn Thr Val Val Ser Arg Pro
        195                 200                 205 cca ccc caa gtc caa atg gca cca cct gta tct tta gaa cct atg ggc     672
Pro Pro Gln Val Gln Met Ala Pro Pro Val Ser Leu Glu Pro Met Gly
```

|  |  |  |
|---|---|---|
| agt tta tct gcc agc tta gag aac caa cta gaa gct ttc ttg gat gga<br>Ser Leu Ser Ala Ser Leu Glu Asn Gln Leu Glu Ala Phe Leu Asp Gly<br>225                        230                        235                        240 | 720 |
| act tta ccc tca gcc aat gaa att cct cca cta caa agc agc agt gaa<br>Thr Leu Pro Ser Ala Asn Glu Ile Pro Pro Leu Gln Ser Ser Ser Glu<br>                    245                        250                        255 | 768 |
| gac aga gag ccc ttc tct ctg atc gag gac ctc cag aat gat ctg ctg<br>Asp Arg Glu Pro Phe Ser Leu Ile Glu Asp Leu Gln Asn Asp Leu Leu<br>                260                        265                        270 | 816 |
| agt cac tca ggt atg ctg gac cat tca cac tca ccc atg gag act tcc<br>Ser His Ser Gly Met Leu Asp His Ser His Ser Pro Met Glu Thr Ser<br>       275                        280                        285 | 864 |
| gag acc cag ttt gct gca ggt act ccc tgt ctg tct ctc gac ctg tca<br>Glu Thr Gln Phe Ala Ala Gly Thr Pro Cys Leu Ser Leu Asp Leu Ser<br>          290                        295                        300 | 912 |
| gac tca aac ttg gac aac atg gag tgg ttg gac att acc atg ccc aac<br>Asp Ser Asn Leu Asp Asn Met Glu Trp Leu Asp Ile Thr Met Pro Asn<br>305                        310                        315                        320 | 960 |
| tcc tct tca gga ctc act cct ctc agc acc acc gcg ccg agc atg ttc<br>Ser Ser Ser Gly Leu Thr Pro Leu Ser Thr Thr Ala Pro Ser Met Phe<br>                    325                        330                        335 | 1008 |
| tct gct gac ttt cta gac cca cag gac cta ccg ctg cca tgg gac<br>Ser Ala Asp Phe Leu Asp Pro Gln Asp Leu Pro Leu Pro Trp Asp<br>          340                        345                        350 | 1053 |
| taacgtcaca gatttctttt ctgagagttg atgaggttta agaacatgaa gattctaaaa | 1113 |
| ggtcagtttt tagagataga tctatagttg cattgttgca atcaaaatat gttgtcacag | 1173 |
| aaagaatagg tggaaggtca tagcctggaa cccaagtttg aaaacatttc attgtgttca | 1233 |
| gtagtgaatt tctacagttt aacatagcac agggccttct gaaaatcgca cttgtcaaag | 1293 |
| acgactcatc tatttctcca gacttcagta aagaatgaaa agtaccttta gataaaaaca | 1353 |
| aagaagagta atatatgcag cacagtgacg ttaggattct ggtaattaac tacatttaaa | 1413 |
| tctctggtca cttttaagacc ctaaataaaa ggcagacagc tccactcaaa aactaaggct | 1473 |
| gatgtgaggg aggtgagagg tcactgcact tggtacttcc tagagacggc cggagccagg | 1533 |
| cccaagacac agcagaggtc aaaggcagtg gagagccttg gccagttcag tgacagcttc | 1593 |
| tggctgaaga cttttggttc tattcagaaa cctgtgtcgt ttttttggtg ttgtagttta | 1653 |
| ttttgtgatt ttttggaatc gtactttata tttccaaatt taaatttaaa tgcaagatct | 1713 |
| ttcaacataa acagaagata cctacaaaat actgtcagaa gtccaggtat actgataaca | 1773 |
| ctgaaaattc tattagcaac cttctgggtt ggttagattg attttaatgt atatattaga | 1833 |
| catttgtatg tatgctctga cattgtgatt tgtacagcct accaaccaat ctaactaaaa | 1893 |
| ttacatatat aatctgtaaa catacatacg agactgtaac actaaacatg tcggatggct | 1953 |
| ggggtaagga aatgggtatc caaggtccta ctttttttaat agctcgaata tttctagagt | 2013 |
| acttgagcca catgtatttc tgtatttaaa gaattgctga ctaactttca ggtaaccaga | 2073 |
| cccatctcaa agaaccaaga aaaggcttta gcatgaaata tctttctgag ctggcgagtt | 2133 |
| agaagaatgg aaggtaaggg gaaggtctgt catctaccca ggacattccc atgatgagta | 2193 |
| caggtcagat tgtgccacaa ggtgggcctc cacgtccctg ccctggccct ctttcttctg | 2253 |
| tcactaaccc tggttatcat tttacaggct tgtaactgga tattctacca gagctctcac | 2313 |
| tatattgtca agcctaagat tgaaaaactg gaggctttat tagtgttttt atatagaaaa | 2373 |
| cagttattac atatgtgtta agtcatttct taagaatttt ctaaaatgcc aactatcaca | 2433 |

-continued

```
ggattatttc aagctagtca ttgaggtata tgacaaaatg taaataacaa aaaactgaaa    2493
tctaccaaaa gagcatggag attttctta aataataata ttgtgctctc cacctcaccc    2553
ttgtgtaaac cctcaggtca ggttggttcc cctgggtcac aaaatggtaa atgttccata    2613
ctgacatgcc ggaggcagcc tgacccgtta tttggaaaga atttgtgaat tatttctggg    2673
tttgtgtttt gcctaagagc tgatcttatt tctgatttgt gtgtgtgtgg tttataaatt    2733
ttactacgtg taacaaaagt ctgcttttcc agcatgagca cactggagcc ctctgctcac    2793
tggcacttcc tgactcaaag gcactaacag tgctcatgtg ccttccagac ggttcaaggc    2853
agaggccact gtgctcagtg tagtctgtga tgaatagttt aagtgttcag aaattggtaa    2913
accaacacac gggatacaat aactctctgt taaccagaac accgtcattt gaccaagccc    2973
tacaagagtt taccacacta tgatgttctgt gaatcctcga gtcagttcca ttgagagggg   3033
cctgtctcca gggccaggct atttacttgg gaaagtattt tcttacagt tcttggccac    3093 agttttttttg ctgagggttt ctgtctgggc ctatcaggtc catacttaga ccctgagcat    3153
cttcttcatt cagatttgaa tggcttatta aattagcacc aaatatcagt gggactgtag    3213
aaggtaaccg aacactagta ccattgactc tcgttgaata actttatatt tccataatcc    3273
tgaattgtgt agatagttt ctagctctcg ggtccctta ttgcttttta aaataggggtt     3333 tgaaacatgc cacaggaagg ttgctctcca aaaatacaca gtgcagtgca agaaaatgct    3393
atctcattgg cctactctcc tatgaattgc taaagtgccc acttcacata tgtgtttaaa    3453
cctttataaa ccagtatttc acttttaaaa agacaaggca tctctaccca ttaactctgc    3513
aagccactcc acttgcacca ttccgcttga ccctcctctc tcctggcttg ggtcaccagc    3573
caggcacctg tgacacgagt gctgctctcc aggatctcca ctacatgttc caggttggag    3633
tgaggacgcg ctatgtgctc acactcatgt gacatgacca aagatgatac tctgtaaaca    3693
aggcccttct gaccggactc agtgcgtgtg atggtgagtg caatgaggaa gggtggatat    3753
tgactaaaga ctggttgttg ttgttgttta ggttagtgtc acagccatta cagcacaagt    3813
caaagtcgcc agttgaattt tcattatgca cgtgtgtggt ttaagcagtg gtactgttgt    3873
atatcatatt gtaaagtatc atactgccaa gaaaataact cctagaaagg cattatctca    3933
catccccatc ttactttcct acatgttctc aaaacacagt agtaccagcc ttacctttct    3993
gctgtatgta gatagtcaga tcatcctact ggggtggga tgaatttaaa agttataccaa   4053 aaatttctgt aaagtctttg aaagtctagg agtaggtggt catcttgtac atttcagcaa    4113
agcatccact aggaaacctc ataggacagt gttagtggtt cacgttctag tgttttcct     4173 gaaatgtgca atctactgta tagtattgcc acataattgt acatagatgt attctgaatt    4233
tgtggaattt cttgcttaga tactattgtg tttgtttcat atgaatattt ttgtaattct    4293
aaaagagatc ttatttaaat ttcctttta aaagccgcat ggttctgtga tccatgtaac    4353
tgacactttt tggctttcag tgctgtttag aaacagtggc aaaggcaggg tggtgctgcc    4413
tgcaagctgc tgcctatgga aggcaaagtc atagtaatga gatagcacct ctgaactgtg    4473
cagtcagcat accctgagtg atggctcagg ggcgcactac ctattttgtc accagagctg    4533
actcaggctt cctggaccct caaccccaga tcattccagg cagcatagct ttcttcacag    4593 tccttttcaga attcccaggc tgaaatcagc catagcagtt gacaaaacag ctatccccac    4653
aagtgatgag atagtccctt tactgtcctc aaatggactt ggcctagag acgtggtaaa     4713 gcactttggc agggtttaaa atatttgtga gaagcccaca tttcagtata catcctcact    4773
```

```
ggcttccatg cacccacctg acggtagcct cacagaagtc ctggctgtca ctcaggtggg      4833
gagctcatgg tgccgctggg gactttttag agaaatgtaa agagaatagc tattcagtgt      4893
ctactagcag agcaacatgt gtcaatttaa ccaaattcac aaataaccct ccattttca       4953 atatctgcta ctgtaaacat gaatattgaa tactgacaag agaataccca tacaaatcgt      5013
cccaccgccc tagaggccac agaattagcc caaaattatc aaagaacatt aactggaagg      5073
tcaggttttt caaggaacat agcttacaaa tgcatcagtg tgtatctgga gagcatccta      5133
actgcatttc aactcatctt ttaagtgatt tcagtcaaaa ctggaaaaca actaagatgt      5193 agtaatttt ttttcctggt tcaaaccttc ataacttgc tcattcagca gtctctctga       5253
gctacatttt tatttgtaaa gtgactctgt ctgcatggca atgagcaggt gcgtgttttt      5313
tccacattcg cccttcttg cagtatccag ggaaacacat cattacaaag gtttctacc       5373 tgaaatcttt catggaaggc ctacaattcg aaagctgca catgtttaca gaagagctct       5433
taccctccat gcaaacactt tgctctgtgg tgtcacagct ttgtgacaat aagatggcaa      5493
tctcggatct acaaggtgct gtcgggaatc aaataaaata tgttatcaga gatatcatca      5553
catctatagt gtttaacaga gctttatgcc aactactaag acaaagcttt aacaaagttt      5613
atagaatact gaaactcgta acaattacct ctctacgtga tgctgtaagg aatcttgcta      5673
atttggtagg aagaggaagc atttaggaaa gggtttagta tctaccaaaa gtacttgacc      5733
tcaagtaacc aatagtaatg caaacttgct ttaaaggaac caaaggcatt gccaagtatt      5793
tgccaaaagg aggcactttt tatttaaaat ttgagactaa tgagatctca aaaatcagcc      5853 ccaaaaggt attatccatt taaggttata attttcacta agatgtagat atttctctta      5913 ttgtttcat gtaaaatagt atagagttgt tttgttggtt taagagtaac attcagtagt       5973
aatacaaagt tttttttcta tgtagaaatt agttttcttt tcttgcttgc aatagaaatg      6033
caatgtgata ggtgtttctc ttcttatttt cattgtcaca ttatgtctta gcatctcact      6093
ttatgaaaaa aaggagaaag ataccaatct acagagccct gcttgttgaa gcactagttt      6153
aatcaacaaa aaattatggc aatcgggggt ccattcatct attgccttta tgttgttttt      6213
taaaagaaaa accatgatgc ctttgtattt gctgtttgca ccctgaaat caattccata      6273 tcatgtttga atgccataca ttttgcacat gtactgtaca taagtaatgc atactgtatt      6333
tttatatgtg tgcacattta tcatcagatc ttttgtacat agtggcagta ttgtagctga      6393
tcgggaaatg tttgatatct cagcaatttt gcatttttgt gtctcaaata aaagacattt      6453
tgatgt                                                                6459
```

<210> SEQ ID NO 7
<211> LENGTH: 351
<212> TYPE: PRT
<213> ORGANISM: Mus musculus

<400> SEQUENCE: 7

```
Gln Thr Ser Pro Gln Ala Gly Met Gln Thr Gln Pro Gln Ile Ala Thr
  1               5                  10                  15

Ala Ala Gln Ile Pro Thr Ala Ala Leu Ala Ser Gly Leu Ala Pro Thr
             20                  25                  30

Val Pro Gln Thr Gln Asp Thr Phe Pro Gln His Val Leu Ser Gln Pro
         35                  40                  45

Gln Gln Val Arg Lys Val Phe Thr Asn Ser Ala Ser Ser Asn Thr Val
     50                  55                  60

Leu Pro Tyr Gln Arg His Pro Ala Pro Ala Val Gln Gln Pro Phe Ile
```

```
                65                  70                  75                  80
Asn Lys Ala Ser Asn Ser Val Leu Gln Ser Arg Asn Ala Pro Leu Pro
                85                  90                  95

Ser Leu Gln Asn Gly Pro Asn Thr Pro Asn Lys Pro Ser Ser Pro Pro
            100                 105                 110

Pro Pro Gln Gln Phe Val Val Gln His Ser Leu Phe Gly Ser Pro Val
            115                 120                 125

Ala Lys Thr Lys Asp Pro Pro Arg Tyr Glu Ala Ile Lys Gln Thr
        130                 135                 140

Arg Ser Thr Gln Ala Pro Leu Pro Glu Ile Ser Asn Ala His Ser Gln
145                 150                 155                 160

Gln Met Asp Asp Leu Phe Asp Ile Leu Ile Lys Ser Gly Glu Ile Ser
                165                 170                 175

Leu Pro Ile Lys Glu Pro Ser Pro Ile Ser Lys Met Arg Pro Val
            180                 185                 190

Thr Ala Ser Ile Thr Thr Met Pro Val Asn Thr Val Val Ser Arg Pro
                195                 200                 205

Pro Pro Gln Val Gln Met Ala Pro Pro Val Ser Leu Glu Pro Met Gly
            210                 215                 220

Ser Leu Ser Ala Ser Leu Glu Asn Gln Leu Glu Ala Phe Leu Asp Gly
225                 230                 235                 240

Thr Leu Pro Ser Ala Asn Glu Ile Pro Pro Leu Gln Ser Ser Glu
                245                 250                 255

Asp Arg Glu Pro Phe Ser Leu Ile Glu Asp Leu Gln Asn Asp Leu Leu
            260                 265                 270

Ser His Ser Gly Met Leu Asp His Ser His Ser Pro Met Glu Thr Ser
            275                 280                 285

Glu Thr Gln Phe Ala Ala Gly Thr Pro Cys Leu Ser Leu Asp Leu Ser
        290                 295                 300

Asp Ser Asn Leu Asp Asn Met Glu Trp Leu Asp Ile Thr Met Pro Asn
305                 310                 315                 320

Ser Ser Ser Gly Leu Thr Pro Leu Ser Thr Thr Ala Pro Ser Met Phe
                325                 330                 335

Ser Ala Asp Phe Leu Asp Pro Gln Asp Leu Pro Leu Pro Trp Asp
            340                 345                 350

<210> SEQ ID NO 8
<211> LENGTH: 35
<212> TYPE: PRT
<213> ORGANISM: Mus musculus

<400> SEQUENCE: 8

Val Thr Lys Met Lys Val Ala Asp Leu Lys Arg Glu Leu Lys Leu Arg
  1               5                  10                  15

Gly Leu Ala Val Asn Gly Asn Lys Thr Glu Leu Gln Asp Arg Leu Gln
                20                  25                  30

Thr Ala Leu
        35

<210> SEQ ID NO 9
<211> LENGTH: 35
<212> TYPE: PRT
<213> ORGANISM: Mus musculus

<400> SEQUENCE: 9

Leu Asp Asp Met Lys Val Ala Glu Leu Lys Gln Glu Leu Lys Leu Arg
```

```
                1               5                  10                 15
Ser Leu Pro Val Ser Gly Thr Lys Thr Glu Leu Ile Glu Arg Leu Arg
                        20                 25                 30

Ala Tyr Gln
        35

<210> SEQ ID NO 10
<211> LENGTH: 35
<212> TYPE: PRT
<213> ORGANISM: Mus musculus

<400> SEQUENCE: 10

Val Lys Lys Leu Lys Val Ser Glu Leu Lys Glu Glu Leu Lys Lys Arg
  1               5                  10                 15

Arg Leu Ser Asp Lys Gly Leu Lys Ala Asp Leu Met Glu Arg Leu Gln
                20                 25                 30

Ala Ala Leu
        35

<210> SEQ ID NO 11
<211> LENGTH: 35
<212> TYPE: PRT
<213> ORGANISM: Mus musculus

<400> SEQUENCE: 11

Val Lys Lys Leu Lys Val Ser Glu Leu Lys Glu Glu Leu Lys Lys Arg
  1               5                  10                 15

Arg Leu Ser Asp Lys Gly Leu Lys Ala Glu Leu Met Glu Arg Leu Gln
                20                 25                 30

Ala Ala Leu
        35

<210> SEQ ID NO 12
<211> LENGTH: 35
<212> TYPE: PRT
<213> ORGANISM: Mus musculus

<400> SEQUENCE: 12

Val Lys Lys Leu Lys Val Ser Glu Leu Lys Glu Glu Leu Lys Lys Arg
  1               5                  10                 15

Arg Leu Ser Asp Lys Gly Leu Lys Ala Asp Leu Met Asp Arg Leu Gln
                20                 25                 30

Ala Ala Leu
        35

<210> SEQ ID NO 13
<211> LENGTH: 35
<212> TYPE: PRT
<213> ORGANISM: Mus musculus

<400> SEQUENCE: 13

Val Lys Lys Leu Lys Val Ser Glu Leu Lys Glu Glu Leu Lys Lys Arg
  1               5                  10                 15

Arg Leu Ser Asp Lys Gly Leu Lys Ala Asp Leu Met Asp Arg Leu Gln
                20                 25                 30

Ala Ala Leu
        35

<210> SEQ ID NO 14
<211> LENGTH: 35
```

```
<212> TYPE: PRT
<213> ORGANISM: Mus musculus

<400> SEQUENCE: 14

Met Glu Gln Leu Lys Val Leu Glu Leu Lys Gln Ile Cys Lys Ser Leu
 1               5                  10                  15

Asp Leu Ser Ile Thr Gly Lys Lys Ala Val Leu Gln Asp Arg Ile Lys
            20                  25                  30

Gln Phe Leu
        35

<210> SEQ ID NO 15
<211> LENGTH: 35
<212> TYPE: PRT
<213> ORGANISM: Mus musculus

<400> SEQUENCE: 15

Val Lys Lys Leu Lys Val Ser Glu Leu Lys Glu Glu Leu Lys Lys Arg
 1               5                  10                  15

Arg Leu Ser Asp Lys Gly Leu Lys Ala Asp Leu Met Asp Arg Leu Gln
            20                  25                  30

Ala Ala Leu
        35

<210> SEQ ID NO 16
<211> LENGTH: 35
<212> TYPE: PRT
<213> ORGANISM: Mus musculus

<400> SEQUENCE: 16

Val Lys Lys Leu Lys Val Ser Glu Leu Lys Glu Glu Leu Lys Lys Arg
 1               5                  10                  15

Arg Leu Ser Asp Lys Gly Leu Lys Ala Asp Leu Met Asp Arg Leu Gln
            20                  25                  30

Ala Ala Leu
        35

<210> SEQ ID NO 17
<211> LENGTH: 35
<212> TYPE: PRT
<213> ORGANISM: Mus musculus

<400> SEQUENCE: 17

Leu Gln Ala Leu Arg Val Thr Asp Leu Lys Ala Ala Leu Glu Gln Arg
 1               5                  10                  15

Gly Leu Ala Lys Ser Gly Gln Lys Ser Ala Leu Val Lys Arg Leu Lys
            20                  25                  30

Gly Ala Leu
        35

<210> SEQ ID NO 18
<211> LENGTH: 35
<212> TYPE: PRT
<213> ORGANISM: Mus musculus

<400> SEQUENCE: 18

Leu Gln Ala Leu Arg Val Thr Asp Leu Lys Ala Ala Leu Glu Gln Arg
 1               5                  10                  15

Gly Leu Ala Lys Ser Gly Gln Lys Ser Ala Leu Val Lys Arg Leu Lys
            20                  25                  30
```

```
Gly Ala Leu
        35

<210> SEQ ID NO 19
<211> LENGTH: 35
<212> TYPE: PRT
<213> ORGANISM: Mus musculus

<400> SEQUENCE: 19

Leu Ser Glu Leu Arg Val Ile Asp Leu Arg Ala Glu Leu Lys Lys Arg
 1               5                  10                  15

Asn Leu Asp Thr Gly Gly Asn Lys Ser Val Leu Met Glu Arg Leu Lys
            20                  25                  30

Lys Ala Val
        35

<210> SEQ ID NO 20
<211> LENGTH: 35
<212> TYPE: PRT
<213> ORGANISM: Mus musculus

<400> SEQUENCE: 20

Leu Ser Asp Leu Arg Val Ile Asp Leu Arg Ala Glu Leu Arg Lys Arg
 1               5                  10                  15

Asn Val Asp Ser Ser Gly Asn Lys Ser Val Leu Met Glu Arg Leu Lys
            20                  25                  30

Lys Ala Ile
        35

<210> SEQ ID NO 21
<211> LENGTH: 35
<212> TYPE: PRT
<213> ORGANISM: Mus musculus

<400> SEQUENCE: 21

Val Arg Arg Leu Lys Val Asn Glu Leu Arg Glu Glu Leu Gln Arg Arg
 1               5                  10                  15

Gly Leu Asp Thr Arg Gly Leu Lys Thr Glu Leu Ala Glu Arg Leu Gln
            20                  25                  30

Ala Ala Leu
        35

<210> SEQ ID NO 22
<211> LENGTH: 35
<212> TYPE: PRT
<213> ORGANISM: Mus musculus

<400> SEQUENCE: 22

Ile Lys Ala Leu Lys Val Ser Gln Leu Lys Asp Ile Leu Arg Asp Arg
 1               5                  10                  15

Gly Leu Arg Val Ser Gly Lys Lys Ala Asp Leu Leu Asp Asn Leu Thr
            20                  25                  30

Asn Tyr Val
        35

<210> SEQ ID NO 23
<211> LENGTH: 35
<212> TYPE: PRT
<213> ORGANISM: Mus musculus

<400> SEQUENCE: 23
```

Ala Asn Lys Leu Lys Val Asp Glu Leu Arg Leu Lys Leu Ala Glu Arg
1               5                   10                  15

Gly Leu Ser Thr Thr Gly Val Lys Ala Val Leu Val Glu Arg Leu Glu
            20                  25                  30

Glu Ala Ile
        35

<210> SEQ ID NO 24
<211> LENGTH: 3907
<212> TYPE: PRT
<213> ORGANISM: Mus musculus

<400> SEQUENCE: 24

Cys Cys Ala Ala Gly Gly Gly Ala Thr Cys Ala Thr Gly Cys Cys Gly
1               5                   10                  15

Cys Cys Thr Thr Thr Gly Ala Ala Ala Gly Thr Cys Cys Ala Cys Gly
            20                  25                  30

Cys Cys Gly Cys Ala Thr Thr Cys Ala Thr Gly Ala Gly Cys Cys Ala
            35                  40                  45

Gly Ala Gly Ala Ala Gly Gly Ala Gly Cys Thr Thr Gly Gly Ala Gly
        50                  55                  60

Cys Gly Gly Cys Cys Ala Gly Gly Ala Cys Ala Gly Ala Gly Gly Gly
65              70                  75                  80

Ala Cys Thr Ala Thr Cys Thr Cys Ala Ala Ala Cys Gly Gly Ala Ala
            85                  90                  95

Gly Ala Thr Thr Cys Gly Thr Thr Cys Cys Cys Gly Gly Cys Cys Gly
            100                 105                 110

Gly Ala Gly Ala Gly Ala Thr Cys Gly Gly Ala Gly Cys Thr Gly Gly
        115                 120                 125

Thr Cys Ala Gly Gly Ala Thr Gly Cys Ala Cys Ala Thr Thr Thr Thr
    130                 135                 140

Gly Gly Ala Ala Gly Ala Gly Ala Cys Cys Thr Cys Gly Gly Cys Thr
145                 150                 155                 160

Gly Ala Gly Cys Cys Ala Thr Cys Cys Cys Thr Cys Cys Ala Gly Gly
                165                 170                 175

Cys Cys Ala Ala Gly Cys Ala Gly Cys Thr Gly Ala Ala Gly Cys Thr
            180                 185                 190

Gly Ala Ala Gly Ala Gly Ala Cys Cys Ala Gly Ala Cys Thr Ala Ala
        195                 200                 205

Gly Cys Cys Gly Ala Thr Gly Ala Cys Cys Thr Cys Ala Ala Thr Gly
    210                 215                 220

Ala Gly Ala Ala Gly Ala Thr Thr Gly Cys Ala Cys Ala Gly Ala Gly
225                 230                 235                 240

Gly Cys Cys Thr Gly Gly Cys Cys Cys Ala Thr Gly Gly Ala Gly
                245                 250                 255

Cys Thr Gly Gly Thr Gly Gly Ala Gly Ala Ala Gly Ala Ala Cys Ala
    260                 265                 270

Thr Cys Cys Thr Thr Cys Cys Thr Gly Thr Thr Gly Ala Gly Thr Cys
            275                 280                 285

Cys Ala Gly Cys Thr Gly Ala Ala Gly Ala Ala Gly Cys Cys
            290                 295                 300

Ala Thr Cys Ala Thr Gly Thr Gly Gly Cys Cys Ala Gly Gly
305                 310                 315                 320

Thr Gly Ala Ala Cys Thr Ala Cys Cys Cys Ala Ala Ala Gly Thr
                325                 330                 335

-continued

Ala Gly Cys Ala Gly Ala Cys Ala Gly Cys Thr Cys Thr Thr Cys Cys
340 345 350

Thr Thr Cys Gly Ala Thr Gly Ala Gly Gly Ala Cys Ala Gly Cys Ala
355 360 365

Gly Cys Gly Ala Thr Gly Cys Cys Thr Thr Ala Thr Cys Cys Cys Cys
370 375 380

Cys Gly Ala Gly Cys Ala Gly Cys Cys Thr Gly Cys Cys Ala Gly Cys
385 390 395 400

Cys Ala Thr Gly Ala Gly Thr Cys Cys Cys Ala Gly Gly Gly Thr Thr
405 410 415

Cys Thr Gly Thr Gly Cys Cys Gly Thr Cys Ala Cys Cys Cys Cys Thr
420 425 430

Gly Gly Ala Gly Gly Cys Cys Cys Gly Ala Gly Thr Cys Ala Gly Cys
435 440 445

Gly Ala Ala Cys Cys Ala Cys Thr Gly Cys Thr Cys Ala Gly Thr Gly
450 455 460

Cys Cys Ala Cys Cys Thr Cys Thr Gly Cys Ala Thr Cys Cys Cys Cys
465 470 475 480

Cys Ala Cys Cys Cys Ala Gly Gly Thr Thr Gly Thr Gly Thr Cys Thr
485 490 495

Cys Ala Ala Cys Thr Thr Cys Cys Gly Ala Thr Gly Gly Gly Cys Cys
500 505 510

Gly Gly Gly Ala Thr Thr Cys Cys Ala Gly Ala Gly Ala Ala Ala Thr
515 520 525

Gly Cys Thr Thr Thr Thr Cys Cys Thr Gly Gly Cys Ala Gly Ala Gly
530 535 540

Cys Ala Gly Cys Cys Thr Cys Cys Thr Cys Thr Gly Cys Cys Thr Cys
545 550 555 560

Cys Cys Cys Cys Ala Cys Cys Thr Cys Thr Gly Cys Thr Gly Cys Cys
565 570 575

Thr Cys Cys Cys Ala Gly Cys Cys Thr Cys Ala Cys Cys Ala Ala Thr
580 585 590

Gly Gly Ala Ala Cys Cys Ala Cys Thr Ala Thr Cys Cys Cys Cys Ala
595 600 605

Cys Thr Gly Cys Cys Ala Ala Gly Thr Cys Cys Ala Cys Cys Cys Cys
610 615 620

Cys Ala Cys Ala Cys Thr Cys Ala Thr Thr Ala Ala Gly Cys Ala Ala
625 630 635 640

Ala Gly Cys Cys Ala Ala Cys Cys Cys Ala Ala Gly Thr Cys Thr Gly
645 650 655

Cys Cys Ala Gly Thr Gly Ala Gly Ala Ala Gly Thr Cys Ala Cys Ala
660 665 670

Gly Cys Gly Cys Ala Gly Cys Ala Ala Gly Ala Ala Gly Gly Cys Cys
675 680 685

Ala Ala Gly Gly Ala Gly Cys Thr Gly Ala Ala Gly Cys Cys Ala Ala
690 695 700

Ala Gly Gly Thr Gly Ala Ala Gly Ala Ala Gly Cys Thr Cys Ala Ala
705 710 715 720

Gly Thr Ala Cys Cys Ala Cys Cys Ala Gly Thr Ala Cys Ala Thr Cys
725 730 735

Cys Cys Cys Cys Cys Gly Gly Ala Cys Cys Ala Gly Ala Ala Gly Cys
740 745 750

-continued

```
Ala Gly Gly Ala Cys Ala Gly Gly Gly Gly Cys Ala Cys Cys
            755                 760                 765
Cys Cys Cys Cys Ala Thr Gly Ala Cys Thr Cys Ala Thr Cys Cys
770                 775                 780
Thr Ala Cys Gly Cys Cys Ala Gly Ala Thr Cys Cys Thr Gly Cys
785                 790                 795                 800
Ala Gly Cys Ala Gly Cys Ala Gly Cys Ala Gly Thr Cys Thr Thr
                805                 810                 815
Cys Cys Thr Cys Cys Ala Gly Cys Thr Gly Cys Ala Gly Ala Thr Cys
            820                 825                 830
Cys Thr Cys Ala Ala Cys Ala Gly Cys Ala Gly Cys Ala Gly Cys
            835                 840                 845
Ala Gly Cys Ala Gly Cys Ala Cys Cys Ala Cys Ala Ala Cys Thr Ala
    850                 855                 860
Cys Cys Ala Gly Gly Cys Cys Ala Thr Cys Cys Thr Gly Cys Cys Thr
865                 870                 875                 880
Gly Cys Cys Cys Cys Gly Cys Cys Ala Ala Ala Gly Thr Cys Ala Gly
                885                 890                 895
Cys Ala Gly Gly Cys Gly Ala Gly Gly Cys Cys Cys Thr Gly Gly Gly
            900                 905                 910
Ala Ala Gly Cys Ala Gly Cys Gly Gly Ala Cys Cys Cys Cys
            915                 920                 925
Cys Cys Ala Gly Thr Ala Cys Gly Cys Ala Gly Cys Cys Thr Cys Thr
    930                 935                 940
Cys Cys Ala Cys Thr Ala Cys Cys Ala Ala Thr Ala Gly Cys Ala Gly
945                 950                 955                 960
Cys Thr Cys Cys Ala Gly Cys Thr Cys Gly Gly Gly Cys Gly Cys Cys
                965                 970                 975
Cys Cys Thr Gly Gly Ala Cys Cys Cys Thr Gly Thr Gly Gly Gly Cys
            980                 985                 990
Thr Gly Gly Cys Ala Cys Gly Thr Cys Ala Gly Ala Ala Cys Ala Gly
    995                 1000                1005
Cys Ala Cys Cys Thr Cys Ala Cys Thr Gly Ala Cys Thr Gly Gly Cys
    1010                1015                1020
Ala Ala Gly Cys Cys Gly Gly Gly Ala Gly Cys Cys Cys Thr Gly Cys
1025                1030                1035                1040
Cys Gly Gly Cys Cys Ala Ala Cys Cys Thr Gly Gly Ala Cys Gly Ala
                1045                1050                1055
Cys Ala Thr Gly Ala Ala Gly Gly Thr Gly Gly Cys Ala Gly Ala Gly
            1060                1065                1070
Cys Thr Gly Ala Ala Gly Cys Ala Gly Ala Gly Cys Thr Gly Ala
            1075                1080                1085
Ala Gly Thr Thr Gly Cys Gly Ala Thr Cys Ala Cys Thr Gly Cys Cys
    1090                1095                1100
Thr Gly Thr Cys Thr Cys Gly Gly Cys Ala Cys Cys Ala Ala Ala
1105                1110                1115                1120
Ala Cys Thr Gly Ala Gly Cys Thr Gly Ala Thr Thr Gly Ala Gly Cys
        1125                1130                1135
Gly Cys Cys Thr Thr Cys Gly Ala Gly Cys Cys Thr Ala Thr Cys Ala
            1140                1145                1150
Ala Gly Ala Cys Cys Ala Ala Ala Thr Cys Ala Gly Cys Cys Cys Thr
        1155                1160                1165
Gly Thr Gly Cys Cys Ala Gly Gly Ala Gly Cys Cys Cys Cys Cys Ala
```

-continued

```
            1170                1175                1180
Ala Gly Gly Cys Cys Cys Thr Gly Cys Cys Gly Cys Cys Ala Cys
1185                1190                1195                1200

Cys Thr Cys Thr Ala Thr Cys Cys Thr Gly Cys Ala Cys Ala Ala Gly
                1205                1210                1215

Gly Cys Thr Gly Gly Cys Gly Ala Gly Gly Thr Gly Gly Thr Gly Gly
                1220                1225                1230

Thr Ala Gly Cys Cys Thr Thr Cys Cys Cys Ala Gly Cys Gly Gly Cys
            1235                1240                1245

Cys Cys Gly Gly Cys Thr Gly Ala Gly Cys Ala Cys Gly Gly Gly Gly
1250                1255                1260

Cys Cys Ala Gly Cys Cys Thr Gly Thr Gly Gly Cys Ala Gly
1265                1270                1275                1280

Cys Ala Gly Gly Cys Cys Thr Gly Gly Cys Thr Cys Ala Gly Cys
            1285                1290                1295

Thr Gly Ala Gly Gly Thr Gly Gly Thr Gly Gly Thr Gly Cys Cys
                1300                1305                1310

Ala Cys Gly Gly Thr Gly Gly Cys Cys Ala Gly Cys Ala Gly Thr Gly
            1315                1320                1325

Gly Gly Gly Thr Gly Gly Thr Gly Ala Ala Gly Thr Thr Gly Gly
                1330                1335                1340

Cys Ala Gly Cys Ala Cys Gly Gly Gly Cys Thr Cys Ala Cys Gly
1345                1350                1355                1360

Cys Cys Cys Cys Cys Cys Gly Thr Gly Thr Cys Thr Cys Cys Cys Ala
                1365                1370                1375

Cys Cys Cys Cys Cys Thr Cys Gly Gly Ala Gly Cys Gly Cys Thr Cys
                1380                1385                1390

Ala Cys Thr Gly Cys Thr Cys Ala Gly Cys Ala Cys Gly Gly Gly Cys
            1395                1400                1405

Gly Ala Thr Gly Ala Ala Ala Ala Cys Thr Cys Cys Ala Cys Cys Cys
1410                1415                1420

Cys Cys Gly Gly Gly Gly Ala Cys Ala Cys Cys Thr Thr Thr Gly Gly
1425                1430                1435                1440

Thr Gly Ala Gly Ala Thr Gly Gly Thr Gly Ala Cys Ala Thr Cys Ala
                1445                1450                1455

Cys Cys Thr Cys Thr Gly Ala Cys Gly Cys Ala Gly Cys Thr Gly Ala
                1460                1465                1470

Cys Cys Cys Thr Gly Cys Ala Gly Gly Cys Cys Thr Cys Gly Cys Cys
            1475                1480                1485

Ala Cys Thr Gly Cys Ala Gly Ala Thr Cys Thr Cys Gly Thr Gly
            1490                1495                1500

Ala Ala Gly Gly Ala Gly Gly Ala Gly Gly Cys Cys Cys Cys
1505                1510                1515                1520

Gly Gly Gly Cys Cys Gly Gly Gly Thr Cys Thr Gly Thr Thr Gly
                1525                1530                1535

Cys Cys Thr Gly Ala Gly Cys Cys Thr Gly Gly Gly Gly Gly
            1540                1545                1550

Cys Gly Gly Gly Cys Gly Gly Ala Gly Cys Thr Ala Gly Ala Gly Gly
            1555                1560                1565

Gly Gly Cys Gly Cys Gly Ala Cys Ala Ala Gly Gly Ala Cys Cys Ala
            1570                1575                1580

Gly Ala Thr Gly Cys Thr Gly Cys Ala Gly Gly Ala Gly Ala Ala Ala
1585                1590                1595                1600
```

-continued

```
Gly Ala Cys Ala Ala Gly Cys Ala Gly Ala Thr Cys Gly Ala Gly Gly
            1605                1610                1615
Cys Gly Cys Thr Gly Ala Cys Gly Cys Gly Cys Ala Thr Gly Cys Thr
        1620                1625                1630
Cys Cys Gly Gly Cys Ala Gly Ala Ala Gly Cys Ala Gly Cys Ala Gly
            1635                1640                1645
Cys Thr Gly Gly Thr Gly Gly Ala Gly Cys Gly Gly Cys Thr Cys Ala
    1650                1655                1660
Ala Gly Cys Thr Gly Cys Ala Gly Cys Thr Gly Gly Ala Gly Cys Ala
1665                1670                1675                1680
Gly Gly Ala Gly Ala Ala Gly Cys Gly Ala Gly Cys Cys Ala Gly
            1685                1690                1695
Cys Ala Gly Cys Cys Gly Cys Cys Cys Cys Cys Gly Cys Cys Cys
        1700                1705                1710
Cys Cys Gly Cys Cys Cys Cys Cys Thr Cys Gly Gly Cys Ala Cys
        1715                1720                1725
Cys Cys Cys Cys Gly Thr Gly Ala Ala Gly Cys Ala Gly Gly Ala Gly
        1730                1735                1740
Ala Ala Cys Ala Gly Cys Thr Thr Cys Thr Cys Cys Ala Gly Cys Thr
1745                1750                1755                1760
Gly Cys Cys Ala Gly Cys Thr Gly Ala Gly Cys Cys Ala Gly Cys Ala
        1765                1770                1775
Gly Cys Cys Cys Cys Thr Gly Gly Gly Cys Cys Cys Cys Gly Cys Thr
    1780                1785                1790
Cys Ala Cys Cys Cys Ala Thr Thr Cys Ala Ala Cys Cys Cys Cys Ala
        1795                1800                1805
Gly Cys Cys Thr Gly Gly Cys Gly Gly Cys Cys Cys Cys Ala Gly Cys
    1810                1815                1820
Cys Ala Cys Cys Ala Ala Cys Cys Ala Cys Ala Thr Ala Gly Ala Cys
1825                1830                1835                1840
Cys Cys Thr Thr Gly Thr Gly Cys Thr Gly Thr Gly Gly Cys Cys Cys
        1845                1850                1855
Cys Gly Gly Gly Gly Cys Cys Cys Cys Gly Thr Cys Cys Gly Thr
    1860                1865                1870
Gly Gly Thr Gly Gly Thr Gly Ala Ala Gly Cys Ala Gly Gly Ala Ala
    1875                1880                1885
Gly Cys Cys Thr Thr Gly Cys Ala Gly Cys Cys Thr Gly Ala Gly Cys
    1890                1895                1900
Cys Cys Gly Ala Gly Cys Cys Gly Gly Thr Cys Cys Cys Cys Gly Cys
1905                1910                1915                1920
Cys Cys Cys Cys Ala Gly Thr Thr Gly Cys Thr Thr Cys Thr Thr Gly
        1925                1930                1935
Gly Gly Gly Cys Cys Thr Cys Ala Gly Gly Cys Cys Cys Cys Ala
    1940                1945                1950
Gly Cys Cys Thr Cys Ala Thr Cys Ala Ala Gly Gly Gly Gly Thr
    1955                1960                1965
Thr Gly Cys Ala Cys Cys Thr Cys Cys Cys Ala Cys Cys Thr Cys
    1970                1975                1980
Ala Thr Cys Ala Cys Cys Gly Ala Cys Thr Cys Cys Ala Cys Ala Gly
1985                1990                1995                2000
Gly Gly Ala Cys Cys Cys Ala Cys Cys Thr Thr Gly Thr Cys Cys Thr
        2005                2010                2015
```

-continued

```
Cys Ala Cys Cys Gly Thr Gly Ala Cys Cys Ala Ala Thr Ala Ala Gly
            2020                2025                2030

Ala Ala Thr Gly Cys Ala Gly Ala Cys Ala Gly Cys Cys Cys Thr Gly
        2035                2040                2045

Gly Cys Cys Thr Gly Thr Cys Cys Ala Gly Thr Gly Gly Gly Ala Gly
    2050                2055                2060

Cys Cys Cys Cys Cys Ala Gly Cys Ala Gly Cys Cys Cys Thr Cys Gly
2065                2070                2075                2080

Thr Cys Cys Cys Ala Gly Cys Cys Thr Gly Gly Cys Thr Cys Thr Cys
                2085                2090                2095

Cys Ala Gly Cys Gly Cys Cys Thr Gly Cys Cys Cys Cys Cys Thr Cys
            2100                2105                2110

Thr Gly Cys Cys Cys Ala Gly Ala Thr Gly Gly Ala Cys Cys Thr Gly
        2115                2120                2125

Gly Ala Gly Cys Ala Cys Cys Cys Ala Cys Thr Gly Cys Ala Gly Cys
    2130                2135                2140

Cys Cys Cys Thr Cys Thr Thr Thr Gly Gly Gly Ala Cys Cys Cys Cys
2145                2150                2155                2160

Cys Ala Cys Thr Thr Cys Thr Cys Thr Gly Cys Thr Gly Ala Ala Gly
                2165                2170                2175

Ala Ala Gly Gly Ala Ala Cys Cys Ala Cys Cys Thr Gly Gly Cys Thr
            2180                2185                2190

Ala Thr Gly Ala Gly Gly Ala Ala Gly Cys Cys Ala Thr Gly Ala Gly
        2195                2200                2205

Cys Cys Ala Gly Cys Ala Gly Cys Cys Cys Ala Ala Ala Cys Ala Gly
    2210                2215                2220

Cys Ala Gly Gly Ala Ala Ala Ala Thr Gly Gly Thr Thr Cys Cys Thr
2225                2230                2235                2240

Cys Ala Ala Gly Cys Cys Ala Gly Cys Ala Gly Ala Thr Gly Gly Ala
                2245                2250                2255

Cys Gly Ala Cys Cys Thr Gly Thr Thr Thr Gly Ala Cys Ala Thr Thr
            2260                2265                2270

Cys Thr Cys Ala Thr Thr Cys Ala Gly Ala Gly Cys Gly Gly Ala Gly
        2275                2280                2285

Ala Ala Ala Thr Thr Thr Cys Ala Gly Cys Ala Gly Ala Thr Thr Thr
    2290                2295                2300

Cys Ala Ala Gly Gly Ala Gly Cys Cys Gly Cys Cys Ala Thr Cys Cys
2305                2310                2315                2320

Cys Thr Gly Cys Cys Ala Gly Gly Gly Ala Ala Gly Gly Ala Gly Ala
                2325                2330                2335

Ala Gly Cys Cys Ala Thr Cys Cys Cys Cys Gly Ala Ala Gly Ala Cys
            2340                2345                2350

Ala Gly Thr Cys Thr Gly Thr Gly Gly Gly Thr Cys Cys Cys Cys Cys
        2355                2360                2365

Cys Thr Gly Gly Cys Ala Gly Cys Ala Cys Ala Gly Cys Cys Ala Thr
    2370                2375                2380

Cys Ala Cys Cys Thr Thr Cys Thr Gly Cys Thr Gly Ala Gly Cys Thr
2385                2390                2395                2400

Cys Cys Cys Cys Cys Ala Gly Gly Cys Thr Gly Cys Cys Cys Cys Ala
                2405                2410                2415

Cys Cys Thr Cys Cys Thr Cys Cys Ala Gly Gly Cys Thr Cys Ala Cys
            2420                2425                2430

Cys Cys Thr Cys Cys Cys Thr Cys Cys Cys Thr Gly Gly Ala Cys Gly
```

-continued

```
            2435                2440                2445
Cys Cys Thr Gly Gly Ala Gly Gly Ala Cys Thr Thr Cys Cys Thr Gly
       2450                2455                2460
Gly Ala Gly Ala Gly Cys Ala Gly Cys Ala Cys Gly Gly Gly Gly Cys
2465                2470                2475                2480
Thr Gly Cys Cys Cys Cys Thr Gly Cys Thr Gly Ala Cys Cys Ala Gly
            2485                2490                2495
Thr Gly Gly Gly Cys Ala Thr Gly Ala Cys Gly Gly Gly Cys Cys Ala
       2500                2505                2510
Gly Ala Gly Cys Cys Cys Thr Thr Thr Cys Cys Thr Cys Ala
       2515                2520                2525
Thr Thr Gly Ala Cys Gly Ala Cys Cys Thr Cys Cys Ala Thr Ala Gly
       2530                2535                2540
Cys Cys Ala Gly Ala Thr Gly Cys Thr Gly Ala Gly Cys Ala Gly Cys
2545                2550                2555                2560
Ala Cys Thr Gly Cys Cys Ala Thr Cys Cys Thr Gly Gly Ala Cys Cys
            2565                2570                2575
Ala Cys Cys Cys Cys Cys Gly Thr Cys Ala Cys Cys Cys Ala Thr
       2580                2585                2590
Gly Gly Ala Cys Ala Cys Cys Thr Cys Gly Gly Ala Ala Thr Thr Gly
       2595                2600                2605
Cys Ala Cys Thr Thr Thr Gly Thr Thr Cys Cys Thr Gly Ala Gly Cys
       2610                2615                2620
Cys Cys Ala Gly Cys Ala Gly Cys Ala Cys Cys Ala Thr Gly Gly Gly
2625                2630                2635                2640
Cys Cys Thr Gly Gly Ala Cys Cys Thr Gly Gly Cys Thr Gly Ala Thr
            2645                2650                2655
Gly Gly Cys Cys Ala Cys Cys Thr Gly Gly Ala Cys Ala Gly Cys Ala
       2660                2665                2670
Thr Gly Gly Ala Cys Thr Gly Gly Cys Thr Gly Gly Ala Gly Cys Thr
       2675                2680                2685
Gly Thr Cys Gly Thr Cys Ala Gly Gly Thr Gly Gly Thr Cys Cys Cys
       2690                2695                2700
Gly Thr Gly Cys Thr Gly Ala Gly Cys Cys Thr Ala Gly Cys Cys Cys
2705                2710                2715                2720
Cys Cys Cys Thr Cys Ala Gly Cys Ala Cys Cys Ala Cys Ala Gly Cys
            2725                2730                2735
Cys Cys Cys Cys Ala Gly Cys Cys Thr Cys Thr Thr Cys Thr Cys Cys
            2740                2745                2750
Ala Cys Ala Gly Ala Cys Thr Thr Cys Thr Cys Gly Ala Thr Gly
       2755                2760                2765
Gly Cys Cys Ala Thr Gly Ala Thr Thr Gly Cys Ala Gly Cys Thr
       2770                2775                2780
Gly Cys Ala Cys Thr Gly Gly Gly Ala Thr Thr Cys Cys Thr Gly Cys
2785                2790                2795                2800
Thr Thr Gly Thr Ala Gly Cys Thr Cys Thr Cys Thr Gly Gly Cys Thr
            2805                2810                2815
Cys Ala Ala Gly Ala Cys Gly Gly Gly Thr Gly Gly Gly Ala
       2820                2825                2830
Ala Gly Gly Gly Gly Cys Thr Gly Gly Ala Gly Cys Cys Ala Gly
       2835                2840                2845
Gly Gly Thr Ala Cys Thr Cys Cys Ala Ala Thr Gly Cys Gly Thr Gly
       2850                2855                2860
```

-continued

```
Gly Cys Thr Cys Thr Cys Cys Thr Gly Cys Gly Thr Gly Ala Thr Thr
2865                2870                2875                2880

Cys Gly Gly Cys Cys Thr Cys Thr Cys Cys Ala Cys Ala Thr Gly Gly
                2885                2890                2895

Thr Thr Gly Thr Gly Ala Gly Thr Cys Thr Thr Gly Ala Cys Ala Ala
            2900                2905                2910

Thr Cys Ala Cys Ala Gly Cys Cys Cys Cys Thr Gly Cys Thr Thr Thr
        2915                2920                2925

Thr Thr Cys Cys Cys Thr Thr Cys Cys Cys Thr Gly Gly Gly Ala Gly
    2930                2935                2940

Gly Cys Thr Ala Gly Ala Ala Cys Ala Gly Ala Gly Ala Ala Gly Cys
2945                2950                2955                2960

Cys Cys Thr Thr Ala Cys Thr Cys Cys Thr Gly Gly Thr Thr Cys Ala
                2965                2970                2975

Gly Thr Gly Cys Cys Ala Cys Gly Cys Ala Gly Gly Gly Cys Ala Gly
            2980                2985                2990

Ala Gly Gly Ala Gly Ala Gly Cys Ala Gly Cys Thr Gly Thr Cys Ala
        2995                3000                3005

Ala Gly Ala Ala Gly Cys Ala Gly Cys Cys Cys Thr Gly Gly Cys Thr
    3010                3015                3020

Cys Thr Cys Ala Cys Gly Cys Thr Gly Gly Gly Gly Thr Thr Thr Thr
3025                3030                3035                3040

Gly Gly Ala Cys Ala Cys Ala Cys Gly Gly Thr Cys Ala Gly Gly Gly
                3045                3050                3055

Thr Cys Ala Gly Gly Gly Cys Cys Ala Thr Thr Thr Cys Ala Gly Cys
            3060                3065                3070

Thr Thr Gly Ala Cys Cys Thr Cys Cys Thr Thr Thr Thr Thr Thr Gly
        3075                3080                3085

Ala Gly Gly Thr Cys Ala Gly Gly Gly Gly Gly Cys Ala Cys Thr Gly
    3090                3095                3100

Thr Cys Thr Gly Thr Cys Thr Gly Gly Cys Thr Ala Cys Ala Ala Thr
3105                3110                3115                3120

Thr Thr Gly Gly Cys Thr Ala Ala Gly Gly Thr Ala Gly Gly Thr Gly
                3125                3130                3135

Ala Ala Gly Cys Cys Thr Gly Gly Cys Cys Ala Gly Gly Cys Gly Gly
            3140                3145                3150

Gly Ala Gly Gly Cys Thr Thr Cys Thr Cys Thr Thr Cys Thr Gly Ala
        3155                3160                3165

Cys Cys Cys Ala Gly Gly Gly Cys Thr Gly Ala Gly Ala Cys Ala Gly
    3170                3175                3180

Gly Thr Thr Ala Ala Gly Gly Gly Gly Thr Gly Ala Ala Thr Cys Thr
3185                3190                3195                3200

Cys Cys Thr Thr Cys Cys Thr Thr Thr Cys Thr Cys Thr Cys Cys Cys
                3205                3210                3215

Thr Gly Cys Thr Thr Thr Gly Cys Thr Gly Thr Gly Ala Ala Gly Gly
            3220                3225                3230

Gly Ala Gly Ala Ala Ala Thr Thr Ala Gly Cys Cys Thr Gly Gly Gly
        3235                3240                3245

Cys Cys Thr Cys Thr Ala Cys Cys Cys Cys Cys Thr Ala Thr Thr Cys
    3250                3255                3260

Cys Cys Thr Gly Thr Gly Thr Cys Thr Gly Cys Cys Ala Ala Cys Cys
3265                3270                3275                3280
```

-continued

```
Cys Cys Ala Gly Gly Ala Thr Cys Cys Ala Gly Gly Cys Thr
            3285                3290                3295

Cys Cys Cys Thr Gly Cys Cys Ala Thr Thr Thr Ala Gly Thr Gly
            3300                3305                3310

Thr Cys Thr Thr Gly Gly Thr Gly Thr Ala Gly Thr Gly Thr Ala Ala
            3315                3320                3325

Cys Cys Ala Thr Thr Thr Ala Gly Thr Gly Gly Thr Thr Gly Gly Thr
            3330                3335                3340

Gly Gly Cys Ala Ala Cys Ala Ala Thr Thr Thr Thr Ala Thr Gly Thr
3345                3350                3355                3360

Ala Cys Ala Gly Gly Thr Gly Thr Ala Thr Ala Thr Ala Cys Cys Thr
            3365                3370                3375

Cys Thr Ala Thr Ala Thr Thr Ala Thr Ala Thr Ala Thr Cys Gly Ala
            3380                3385                3390

Cys Ala Thr Ala Cys Ala Thr Ala Thr Ala Thr Ala Thr Thr Thr Thr
            3395                3400                3405

Thr Gly Gly Gly Gly Gly Gly Gly Gly Cys Gly Gly Ala Cys Ala
            3410                3415                3420

Gly Gly Ala Gly Ala Thr Gly Gly Thr Gly Cys Ala Ala Cys Thr
3425                3430                3435                3440

Cys Cys Cys Thr Cys Cys Cys Ala Thr Cys Cys Thr Ala Cys Thr Cys
            3445                3450                3455

Thr Cys Ala Cys Ala Gly Ala Ala Gly Gly Gly Cys Cys Thr Gly Gly
            3460                3465                3470

Ala Thr Gly Cys Ala Ala Gly Gly Thr Thr Ala Cys Cys Thr Thr
            3475                3480                3485

Gly Ala Gly Cys Thr Gly Thr Gly Thr Gly Cys Cys Ala Cys Ala Gly
            3490                3495                3500

Thr Cys Thr Gly Gly Thr Gly Cys Cys Cys Ala Gly Thr Cys Thr Gly
3505                3510                3515                3520

Gly Cys Ala Thr Gly Cys Ala Gly Cys Thr Ala Cys Cys Ala Gly
            3525                3530                3535

Gly Cys Cys Cys Ala Cys Cys Cys Ala Thr Cys Ala Cys Gly Thr Gly
            3540                3545                3550

Thr Gly Ala Thr Thr Gly Ala Cys Ala Thr Gly Thr Ala Gly Gly Thr
            3555                3560                3565

Ala Cys Cys Cys Thr Gly Cys Cys Ala Cys Gly Gly Cys Cys Thr Ala
            3570                3575                3580

Thr Gly Cys Cys Cys Cys Ala Cys Cys Thr Gly Cys Cys Cys Thr Gly
3585                3590                3595                3600

Cys Thr Thr Cys Cys Thr Gly Gly Cys Thr Cys Cys Thr Thr Ala Thr
            3605                3610                3615

Cys Ala Gly Thr Gly Cys Cys Ala Thr Gly Ala Gly Gly Gly Cys Ala
            3620                3625                3630

Gly Ala Gly Gly Thr Gly Cys Thr Ala Cys Cys Thr Gly Gly Cys Cys
            3635                3640                3645

Thr Thr Cys Cys Thr Gly Cys Cys Cys Ala Gly Gly Ala Gly Cys Thr Cys
            3650                3655                3660

Thr Cys Cys Ala Cys Cys Cys Ala Cys Thr Cys Ala Cys Ala Thr Thr
3665                3670                3675                3680

Cys Cys Gly Thr Cys Cys Cys Cys Gly Cys Cys Gly Cys Cys Thr Cys
            3685                3690                3695

Ala Cys Thr Gly Cys Ala Gly Cys Cys Ala Gly Cys Gly Thr Gly Gly
```

```
                  3700                3705                3710
Thr Cys Cys Thr Ala Gly Gly Ala Cys Ala Gly Ala Gly Gly Ala
        3715                3720                3725
Gly Cys Thr Thr Cys Gly Gly Cys Cys Ala Gly Cys Thr Thr
    3730                3735                3740
Cys Ala Cys Cys Cys Thr Gly Cys Gly Gly Thr Gly Gly Gly Cys
3745                3750                3755                3760
Thr Gly Ala Gly Gly Gly Thr Gly Gly Cys Cys Ala Thr Cys Thr
            3765                3770                3775
Cys Cys Thr Gly Cys Cys Cys Thr Gly Gly Gly Cys Cys Ala Cys
        3780                3785                3790
Thr Gly Gly Cys Thr Thr Cys Ala Cys Ala Thr Thr Cys Thr Gly
    3795                3800                3805
Gly Cys Thr Gly Ala Cys Thr Cys Ala Thr Ala Gly Gly Gly Ala
    3810                3815                3820
Gly Thr Ala Gly Gly Gly Gly Thr Gly Gly Ala Gly Thr Cys Ala Cys
3825                3830                3835                3840
Cys Ala Ala Ala Cys Cys Ala Gly Thr Gly Cys Thr Gly Gly Gly
            3845                3850                3855
Ala Cys Ala Ala Ala Gly Ala Thr Gly Gly Gly Gly Ala Ala Gly Gly
            3860                3865                3870
Thr Gly Thr Gly Thr Gly Ala Ala Cys Thr Thr Thr Thr Ala Ala
        3875                3880                3885
Ala Ala Thr Ala Ala Ala Cys Ala Cys Ala Ala Ala Ala Cys Ala
        3890                3895                3900
Cys Ala Gly
3905

<210> SEQ ID NO 25
<211> LENGTH: 2424
<212> TYPE: DNA
<213> ORGANISM: Homo sapiens
<220> FEATURE:
<221> NAME/KEY: CDS
<222> LOCATION: (1)..(2421)

<400> SEQUENCE: 25 atg gat tct tcc gtg aaa gag gct ata aaa ggt act gag gtg agc ctc        48
Met Asp Ser Ser Val Lys Glu Ala Ile Lys Gly Thr Glu Val Ser Leu
  1               5                  10                  15 tcc aag gca gca gat gca ttc gcc ttt gag gat gac agc agt aga gat        96
Ser Lys Ala Ala Asp Ala Phe Ala Phe Glu Asp Asp Ser Ser Arg Asp
             20                  25                  30 ggg ctc tct cca gat cag gct agg agc gag gac ccc cag ggc tct aca      144
Gly Leu Ser Pro Asp Gln Ala Arg Ser Glu Asp Pro Gln Gly Ser Thr
         35                  40                  45 gga tcc acc cca gac atc aaa tcc act gag gct cct ctg gac aca atc      192
Gly Ser Thr Pro Asp Ile Lys Ser Thr Glu Ala Pro Leu Asp Thr Ile
     50                  55                  60 cag gat ctc act cct ggc tca gaa agt gac aag aat gat gca gcc tcc      240
Gln Asp Leu Thr Pro Gly Ser Glu Ser Asp Lys Asn Asp Ala Ala Ser
 65                  70                  75                  80 cag cca ggc aac cag tca gac cct ggg aag cag gtt ctc ggc ccc ctc      288
Gln Pro Gly Asn Gln Ser Asp Pro Gly Lys Gln Val Leu Gly Pro Leu
                 85                  90                  95 agc acc ccg att cct gtg cac act gct gta aag tcc aag tct ttg ggt      336
Ser Thr Pro Ile Pro Val His Thr Ala Val Lys Ser Lys Ser Leu Gly
            100                 105                 110
```

-continued

```
gac agt aag aac cgc cac aaa aag ccc aaa gac ccc aaa cca aag gtg    384
Asp Ser Lys Asn Arg His Lys Lys Pro Lys Asp Pro Lys Pro Lys Val
        115                 120                 125 aag aag ctc aaa tac cat cag tac atc ccc cca gac cag aag gca gag    432
Lys Lys Leu Lys Tyr His Gln Tyr Ile Pro Pro Asp Gln Lys Ala Glu
    130                 135                 140 aac tct ccc cca ccc atg gac tct gcc tat gcc cgg ctc ctc cag caa    480
Asn Ser Pro Pro Pro Met Asp Ser Ala Tyr Ala Arg Leu Leu Gln Gln
145                 150                 155                 160 cag cag cta ttc ctg cag cta cag atc ctc agc cag cag cag caa cag    528
Gln Gln Leu Phe Leu Gln Leu Gln Ile Leu Ser Gln Gln Gln Gln Gln
            165                 170                 175 cag cag caa cag cag cag cag caa cag cag cag cag cag cag cag cag    576
Gln Gln Gln Gln Gln Gln Gln Gln Gln Gln Gln Gln Gln Gln Gln Gln
        180                 185                 190 cgg ttc agc tac cct ggg atg cac caa aca cac ctc aaa gaa cca aat    624
Arg Phe Ser Tyr Pro Gly Met His Gln Thr His Leu Lys Glu Pro Asn
    195                 200                 205 gaa cag atg gcc aga aat ccg aat cct tct tca aca cca ctg agc aat    672
Glu Gln Met Ala Arg Asn Pro Asn Pro Ser Ser Thr Pro Leu Ser Asn
210                 215                 220 acc cct cta tcc cct gtc aaa aat agv att tct gga caa act ggt gtt    720
Thr Pro Leu Ser Pro Val Lys Asn Xaa Ile Ser Gly Gln Thr Gly Val
225                 230                 235                 240 tct tct ctc aaa cca ggc ccc ctc cca ccc aac ctg gat gat ctc aag    768
Ser Ser Leu Lys Pro Gly Pro Leu Pro Pro Asn Leu Asp Asp Leu Lys
            245                 250                 255 gtg tca gag tta aga caa cag ctt cga atc cgg ggc ttg cca gtg tca    816
Val Ser Glu Leu Arg Gln Gln Leu Arg Ile Arg Gly Leu Pro Val Ser
        260                 265                 270 ggc acc aag aca gcg ctg gtg gac cgg ctt cgt ccc ttc cag gat tgt    864
Gly Thr Lys Thr Ala Leu Val Asp Arg Leu Arg Pro Phe Gln Asp Cys
    275                 280                 285 gct ggc aac cct gtg ccc aac ttt ggg gac atc aca act gtc acc ttt    912
Ala Gly Asn Pro Val Pro Asn Phe Gly Asp Ile Thr Thr Val Thr Phe
290                 295                 300 cct gtc acg ccc aac acc ttg ccc agt tat cag tcc tcc ccg aca ggc    960
Pro Val Thr Pro Asn Thr Leu Pro Ser Tyr Gln Ser Ser Pro Thr Gly
305                 310                 315                 320 ttc tac cac ttt ggc agc aca agc tcc agc cca ccc atc tcc ccc gcc    1008
Phe Tyr His Phe Gly Ser Thr Ser Ser Ser Pro Pro Ile Ser Pro Ala
            325                 330                 335 tca tct gac ttg tcc gct gca ggg tcc ctg cca gac acc ttc acc gat    1056
Ser Ser Asp Leu Ser Ala Ala Gly Ser Leu Pro Asp Thr Phe Thr Asp
        340                 345                 350 gcg tca cct ggc ttc ggc ctg cac gca tct ccg gtg ccc gcc tgc acg    1104
Ala Ser Pro Gly Phe Gly Leu His Ala Ser Pro Val Pro Ala Cys Thr
    355                 360                 365 gac gag agt ctg ctg agc agc ctg aat ggg ggc tcg ggc ccc tcc gag    1152
Asp Glu Ser Leu Leu Ser Ser Leu Asn Gly Gly Ser Gly Pro Ser Glu
370                 375                 380 cct gat ggg cta gac tct gag aag gac aag atg ctg gtg gag aag cag    1200
Pro Asp Gly Leu Asp Ser Glu Lys Asp Lys Met Leu Val Glu Lys Gln
385                 390                 395                 400 aaa gtg atc aac cag ctc acc tgg aag ctg cgg caa gag cag cgg cag    1248
Lys Val Ile Asn Gln Leu Thr Trp Lys Leu Arg Gln Glu Gln Arg Gln
            405                 410                 415 gtg gaa gag ctg aga atg caa ctg cag aag cag aag agc agc tgc agc    1296
Val Glu Glu Leu Arg Met Gln Leu Gln Lys Gln Lys Ser Ser Cys Ser
```

-continued

```
                  420                 425                 430
gac cag aag cca ctc ccc ttc ttg gcc acc acc atc aaa cag gaa gat    1344
Asp Gln Lys Pro Leu Pro Phe Leu Ala Thr Thr Ile Lys Gln Glu Asp
            435                 440                 445 gtc tcc agc tgc ccc ttc gca ccc cag cag gcg tct ggg aag gga cag    1392
Val Ser Ser Cys Pro Phe Ala Pro Gln Gln Ala Ser Gly Lys Gly Gln
        450                 455                 460 ggc cac agc tct gac agt ccc cct ccg gct tgt gag acg gct cag ctg    1440
Gly His Ser Ser Asp Ser Pro Pro Pro Ala Cys Glu Thr Ala Gln Leu
465                 470                 475                 480 ctg cct cac tgt gtg gag tcc tca ggt caa acc cat gta ctc tcg tcc    1488
Leu Pro His Cys Val Glu Ser Ser Gly Gln Thr His Val Leu Ser Ser
                485                 490                 495 acg ttt ctc agc ccc cag tgc tcc cct cag cac tcg ccc cgt ggg ggc    1536
Thr Phe Leu Ser Pro Gln Cys Ser Pro Gln His Ser Pro Arg Gly Gly
            500                 505                 510 ctg aag agc ccg cag cac atc agc ctg cct cca tca ccc aac aac cat    1584
Leu Lys Ser Pro Gln His Ile Ser Leu Pro Pro Ser Pro Asn Asn His
        515                 520                 525 tac ttc ctg gct tcc tct tcg gga gct cag aga gag aac cat ggg gtc    1632
Tyr Phe Leu Ala Ser Ser Ser Gly Ala Gln Arg Glu Asn His Gly Val
530                 535                 540 tct tca ccc agc agc agc caa ggg tgc gca cag atg act ggt tta caa    1680
Ser Ser Pro Ser Ser Ser Gln Gly Cys Ala Gln Met Thr Gly Leu Gln
545                 550                 555                 560 tct tct gac aag gtg ggg cca acg ttt tca att cca tcc cca act ttt    1728
Ser Ser Asp Lys Val Gly Pro Thr Phe Ser Ile Pro Ser Pro Thr Phe
                565                 570                 575 tct aag tca agt tca gca gtt tca gat atc acc cag ccc cca tcc tat    1776
Ser Lys Ser Ser Ser Ala Val Ser Asp Ile Thr Gln Pro Pro Ser Tyr
            580                 585                 590 gaa gat gca gtg aag cag caa atg act cgg agt cag cag atg gac gaa    1824
Glu Asp Ala Val Lys Gln Gln Met Thr Arg Ser Gln Gln Met Asp Glu
        595                 600                 605 ctc ctg gat gtc ctc att gaa agt gga gaa atg cca gcc gat gcc agg    1872
Leu Leu Asp Val Leu Ile Glu Ser Gly Glu Met Pro Ala Asp Ala Arg
610                 615                 620 gaa gat cat tca tgt ctt cag aaa att cca aag atc cct ggg tcc tcc    1920
Glu Asp His Ser Cys Leu Gln Lys Ile Pro Lys Ile Pro Gly Ser Ser
625                 630                 635                 640 tgc agc cca act gcc atc ccc ccg aag ccc tcg gct tcc ttt gag cag    1968
Cys Ser Pro Thr Ala Ile Pro Pro Lys Pro Ser Ala Ser Phe Glu Gln
                645                 650                 655 gca tct tcg gga ggc cag atg gcc ttc gat cac tac gca aac gac agt    2016
Ala Ser Ser Gly Gly Gln Met Ala Phe Asp His Tyr Ala Asn Asp Ser
            660                 665                 670 gac gaa cac ctg gaa gtc tta ttg aat tct cac agc ccc atc gga aag    2064
Asp Glu His Leu Glu Val Leu Leu Asn Ser His Ser Pro Ile Gly Lys
        675                 680                 685 gtg agc gat gtt acc ctc ctc aaa atc gga agc gag gag cct cct ttt    2112
Val Ser Asp Val Thr Leu Leu Lys Ile Gly Ser Glu Glu Pro Pro Phe
690                 695                 700 gac agc atc atg gat ggc ttc cca ggg aag gct gcg gaa gat ctc ttc    2160
Asp Ser Ile Met Asp Gly Phe Pro Gly Lys Ala Ala Glu Asp Leu Phe
705                 710                 715                 720 agt gct cac gag ctc ttg cct ggg ccc ctc tcc ccg atg cat gca cag    2208
Ser Ala His Glu Leu Leu Pro Gly Pro Leu Ser Pro Met His Ala Gln
                725                 730                 735 ttg tca cct cct tct gtg gac agc agt ggt ctg cag ctg agc tta ccg    2256
```

-continued

```
Leu Ser Pro Pro Ser Val Asp Ser Ser Gly Leu Gln Leu Ser Leu Pro
                740                 745                 750 gaa tct cct tgg gaa aca atg gaa tgg ctg gac ctc act cca cct agt      2304
Glu Ser Pro Trp Glu Thr Met Glu Trp Leu Asp Leu Thr Pro Pro Ser
            755                 760                 765 tcc acg cca ggc ttc agc aac ctt acc tcc agt ggg ccc agc att ttc      2352
Ser Thr Pro Gly Phe Ser Asn Leu Thr Ser Ser Gly Pro Ser Ile Phe
        770                 775                 780 aac atc gat ttt ctg gat gtt aca gat ctt aat ctg aat tcc cct atg      2400
Asn Ile Asp Phe Leu Asp Val Thr Asp Leu Asn Leu Asn Ser Pro Met
785                 790                 795                 800 gat ctc cac tta cag cag tgg taa                                      2424
Asp Leu His Leu Gln Gln Trp
                805
```

<210> SEQ ID NO 26
<211> LENGTH: 807
<212> TYPE: PRT
<213> ORGANISM: Homo sapiens
<220> FEATURE:
<221> NAME/KEY: modified_base
<222> LOCATION: (233)
<223> OTHER INFORMATION: Xaa = any

<400> SEQUENCE: 26

```
Met Asp Ser Ser Val Lys Glu Ala Ile Lys Gly Thr Glu Val Ser Leu
  1               5                  10                  15

Ser Lys Ala Ala Asp Ala Phe Ala Phe Glu Asp Asp Ser Ser Arg Asp
             20                  25                  30

Gly Leu Ser Pro Asp Gln Ala Arg Ser Glu Asp Pro Gln Gly Ser Thr
         35                  40                  45

Gly Ser Thr Pro Asp Ile Lys Ser Thr Glu Ala Pro Leu Asp Thr Ile
     50                  55                  60

Gln Asp Leu Thr Pro Gly Ser Glu Ser Asp Lys Asn Asp Ala Ala Ser
 65                  70                  75                  80

Gln Pro Gly Asn Gln Ser Asp Pro Gly Lys Gln Val Leu Gly Pro Leu
                 85                  90                  95

Ser Thr Pro Ile Pro Val His Thr Ala Val Lys Ser Lys Ser Leu Gly
            100                 105                 110

Asp Ser Lys Asn Arg His Lys Lys Pro Lys Asp Pro Lys Pro Lys Val
        115                 120                 125

Lys Lys Leu Lys Tyr His Gln Tyr Ile Pro Pro Asp Gln Lys Ala Glu
    130                 135                 140

Asn Ser Pro Pro Pro Met Asp Ser Ala Tyr Ala Arg Leu Leu Gln Gln
145                 150                 155                 160

Gln Gln Leu Phe Leu Gln Leu Gln Ile Leu Ser Gln Gln Gln Gln Gln
                165                 170                 175

Gln Gln Gln Gln Gln Gln Gln Gln Gln Gln Gln Gln Gln Gln Gln Gln
            180                 185                 190

Arg Phe Ser Tyr Pro Gly Met His Gln Thr His Leu Lys Glu Pro Asn
        195                 200                 205

Glu Gln Met Ala Arg Asn Pro Asn Pro Ser Ser Thr Pro Leu Ser Asn
    210                 215                 220

Thr Pro Leu Ser Pro Val Lys Asn Xaa Ile Ser Gly Gln Thr Gly Val
225                 230                 235                 240

Ser Ser Leu Lys Pro Gly Pro Leu Pro Pro Asn Leu Asp Asp Leu Lys
                245                 250                 255
```

```
Val Ser Glu Leu Arg Gln Gln Leu Arg Ile Arg Gly Leu Pro Val Ser
            260                 265                 270

Gly Thr Lys Thr Ala Leu Val Asp Arg Leu Arg Pro Phe Gln Asp Cys
            275                 280                 285

Ala Gly Asn Pro Val Pro Asn Phe Gly Asp Ile Thr Thr Val Thr Phe
            290                 295                 300

Pro Val Thr Pro Asn Thr Leu Pro Ser Tyr Gln Ser Ser Pro Thr Gly
305                 310                 315                 320

Phe Tyr His Phe Gly Ser Thr Ser Ser Pro Pro Ile Ser Pro Ala
                325                 330                 335

Ser Ser Asp Leu Ser Ala Ala Gly Ser Leu Pro Asp Thr Phe Thr Asp
            340                 345                 350

Ala Ser Pro Gly Phe Gly Leu His Ala Ser Pro Val Pro Ala Cys Thr
            355                 360                 365

Asp Glu Ser Leu Leu Ser Ser Leu Asn Gly Gly Ser Gly Pro Ser Glu
            370                 375                 380

Pro Asp Gly Leu Asp Ser Glu Lys Asp Lys Met Leu Val Glu Lys Gln
385                 390                 395                 400

Lys Val Ile Asn Gln Leu Thr Trp Lys Leu Arg Gln Glu Gln Arg Gln
                405                 410                 415

Val Glu Glu Leu Arg Met Gln Leu Gln Lys Gln Lys Ser Ser Cys Ser
            420                 425                 430

Asp Gln Lys Pro Leu Pro Phe Leu Ala Thr Thr Ile Lys Gln Glu Asp
            435                 440                 445

Val Ser Ser Cys Pro Phe Ala Pro Gln Gln Ala Ser Gly Lys Gly Gln
            450                 455                 460

Gly His Ser Ser Asp Ser Pro Pro Ala Cys Glu Thr Ala Gln Leu
465                 470                 475                 480

Leu Pro His Cys Val Glu Ser Ser Gly Gln Thr His Val Leu Ser Ser
                485                 490                 495

Thr Phe Leu Ser Pro Gln Cys Ser Pro Gln His Ser Pro Arg Gly Gly
            500                 505                 510

Leu Lys Ser Pro Gln His Ile Ser Leu Pro Pro Ser Pro Asn Asn His
            515                 520                 525

Tyr Phe Leu Ala Ser Ser Ser Gly Ala Gln Arg Glu Asn His Gly Val
            530                 535                 540

Ser Ser Pro Ser Ser Ser Gln Gly Cys Ala Gln Met Thr Gly Leu Gln
545                 550                 555                 560

Ser Ser Asp Lys Val Gly Pro Thr Phe Ser Ile Pro Ser Pro Thr Phe
                565                 570                 575

Ser Lys Ser Ser Ala Val Ser Asp Ile Thr Gln Pro Pro Ser Tyr
            580                 585                 590

Glu Asp Ala Val Lys Gln Gln Met Thr Arg Ser Gln Gln Met Asp Glu
            595                 600                 605

Leu Leu Asp Val Leu Ile Glu Ser Gly Glu Met Pro Ala Asp Ala Arg
            610                 615                 620

Glu Asp His Ser Cys Leu Gln Lys Ile Pro Lys Ile Pro Gly Ser Ser
625                 630                 635                 640

Cys Ser Pro Thr Ala Ile Pro Pro Lys Pro Ser Ala Ser Phe Glu Gln
                645                 650                 655

Ala Ser Ser Gly Gly Gln Met Ala Phe Asp His Tyr Ala Asn Asp Ser
            660                 665                 670

Asp Glu His Leu Glu Val Leu Leu Asn Ser His Ser Pro Ile Gly Lys
```

```
                   675                 680                 685
     Val Ser Asp Val Thr Leu Leu Lys Ile Gly Ser Glu Pro Pro Phe
         690                 695                 700

Asp Ser Ile Met Asp Gly Phe Pro Gly Lys Ala Ala Glu Asp Leu Phe
     705                 710                 715                 720

Ser Ala His Glu Leu Leu Pro Gly Pro Leu Ser Pro Met His Ala Gln
                     725                 730                 735

Leu Ser Pro Pro Ser Val Asp Ser Ser Gly Leu Gln Leu Ser Leu Pro
                 740                 745                 750

Glu Ser Pro Trp Glu Thr Met Glu Trp Leu Asp Leu Thr Pro Pro Ser
             755                 760                 765

Ser Thr Pro Gly Phe Ser Asn Leu Thr Ser Ser Gly Pro Ser Ile Phe
         770                 775                 780

Asn Ile Asp Phe Leu Asp Val Thr Asp Leu Asn Leu Asn Ser Pro Met
     785                 790                 795                 800

Asp Leu His Leu Gln Gln Trp
                     805

<210> SEQ ID NO 27
<211> LENGTH: 3063
<212> TYPE: DNA
<213> ORGANISM: Homo sapiens
<220> FEATURE:
<221> NAME/KEY: CDS
<222> LOCATION: (247)..(3060)

<400> SEQUENCE: 27
gacgtcgcat gctcccggcc gccatggcgg ccgcgggaat tcgattgact cctggagccc     60
gtcagtatcg gcggaattcg cggccgcgtc gacctggctg ccactgtact cctacccagg    120
ggagctcacg gagagttgga tgaattctgg gttgttagct gcggtcagct gggctcccgg    180
gagcctgttg ctggtggaga acagggggcg cctggccaag ggaccagcgg cttgctgaga    240 ctcaac atg aca ctc ctg ggg tct gag cat tcc ttg ctg att agg agc      288
       Met Thr Leu Leu Gly Ser Glu His Ser Leu Leu Ile Arg Ser
         1               5                  10 aag ttc aga tca gtt tta cag tta aga ctt caa caa aga agg acc cag     336
Lys Phe Arg Ser Val Leu Gln Leu Arg Leu Gln Gln Arg Arg Thr Gln
 15                  20                  25                  30 gaa caa ctg gct aac caa ggc ata ata cca cca ctg aaa cgt cca gct     384
Glu Gln Leu Ala Asn Gln Gly Ile Ile Pro Pro Leu Lys Arg Pro Ala
                 35                  40                  45 gaa ttc cat gag caa aga aaa cat ttg gat agt gac aag gct aaa aat     432
Glu Phe His Glu Gln Arg Lys His Leu Asp Ser Asp Lys Ala Lys Asn
             50                  55                  60 tcc ctg aag cgc aaa gcc aga aac agg tgc aac agt gcc gac ttg gtt     480
Ser Leu Lys Arg Lys Ala Arg Asn Arg Cys Asn Ser Ala Asp Leu Val
         65                  70                  75 aat atg cac ata ctc caa gct tcc act gca gag agg tcc att cca act     528
Asn Met His Ile Leu Gln Ala Ser Thr Ala Glu Arg Ser Ile Pro Thr
     80                  85                  90 gct cag atg aag ctg aaa aga gcc cga ctc gcc gat gat ctc aat gaa     576
Ala Gln Met Lys Leu Lys Arg Ala Arg Leu Ala Asp Asp Leu Asn Glu
 95                 100                 105                 110 aaa att gct cta cga cca ggg cca ctg gag ctg gtg gaa aaa aac att     624
Lys Ile Ala Leu Arg Pro Gly Pro Leu Glu Leu Val Glu Lys Asn Ile
                115                 120                 125 ctt cct gtg gat tct gct gtg aaa gag gcc ata aaa ggt aac cag gtg     672
Leu Pro Val Asp Ser Ala Val Lys Glu Ala Ile Lys Gly Asn Gln Val
```

```
                130                 135                 140
agt ttc tcc aaa tcc acg gat gct ttt gcc ttt gaa gag gac agc agc      720
Ser Phe Ser Lys Ser Thr Asp Ala Phe Ala Phe Glu Glu Asp Ser Ser
        145                 150                 155 agc gat ggg ctt tct ccg gat cag act cga agt gaa gac ccc caa aac      768
Ser Asp Gly Leu Ser Pro Asp Gln Thr Arg Ser Glu Asp Pro Gln Asn
    160                 165                 170 tca gcg gga tcc ccg cca gac gct aaa gcc tca gat acc cct tcg aca      816
Ser Ala Gly Ser Pro Pro Asp Ala Lys Ala Ser Asp Thr Pro Ser Thr
175                 180                 185                 190 ggt tct ctg ggg aca aac cag gat ctt gct tct ggc tca gaa aat gac      864
Gly Ser Leu Gly Thr Asn Gln Asp Leu Ala Ser Gly Ser Glu Asn Asp
                195                 200                 205 aga aat gac tca gcc tca cag ccc agc cac cag tca gat gcg ggg aag      912
Arg Asn Asp Ser Ala Ser Gln Pro Ser His Gln Ser Asp Ala Gly Lys
            210                 215                 220 cag ggg ctt ggc ccc ccc agc acc ccc ata gcc gtg cat gct gct gta      960
Gln Gly Leu Gly Pro Pro Ser Thr Pro Ile Ala Val His Ala Ala Val
        225                 230                 235 aag tcc aaa tcc ttg ggt gac agt aag aac cgc cac aaa aag ccc aag     1008
Lys Ser Lys Ser Leu Gly Asp Ser Lys Asn Arg His Lys Lys Pro Lys
    240                 245                 250 gac ccc aag cca aag gtg aag aag ctt aaa tat cac cag tac att ccc     1056
Asp Pro Lys Pro Lys Val Lys Lys Leu Lys Tyr His Gln Tyr Ile Pro
255                 260                 265                 270 cca gac cag aag gca gag aag tcc cct cca cct atg gac tca gcc tac     1104
Pro Asp Gln Lys Ala Glu Lys Ser Pro Pro Pro Met Asp Ser Ala Tyr
                275                 280                 285 gct cgg ctg ctc cag caa cag cag ctg ttc ctg cag ctc caa atc ctc     1152
Ala Arg Leu Leu Gln Gln Gln Gln Leu Phe Leu Gln Leu Gln Ile Leu
            290                 295                 300 agc cag cag cag cag cag cag caa cac cga ttc agc tac cta ggg atg     1200
Ser Gln Gln Gln Gln Gln Gln Gln His Arg Phe Ser Tyr Leu Gly Met
        305                 310                 315 cac caa gct cag ctt aag gaa cca aat gaa cag atg gtc aga aat cca     1248
His Gln Ala Gln Leu Lys Glu Pro Asn Glu Gln Met Val Arg Asn Pro
    320                 325                 330 aac tct tct tca acg cca ctg agc aat acc ccc ttg tct cct gtc aaa     1296
Asn Ser Ser Ser Thr Pro Leu Ser Asn Thr Pro Leu Ser Pro Val Lys
335                 340                 345                 350 aac agt ttt tct gga caa act ggt gtc tct tct ttc aaa cca ggc cca     1344
Asn Ser Phe Ser Gly Gln Thr Gly Val Ser Ser Phe Lys Pro Gly Pro
                355                 360                 365 ctc cca cct aac ctg gat gat ctg aag gtc tct gaa tta aga caa cag     1392
Leu Pro Pro Asn Leu Asp Asp Leu Lys Val Ser Glu Leu Arg Gln Gln
            370                 375                 380 ctt cga att cgg ggc ttg cct gtg tca ggc acc aaa acg gct ctc atg     1440
Leu Arg Ile Arg Gly Leu Pro Val Ser Gly Thr Lys Thr Ala Leu Met
        385                 390                 395 gac cgg ctt cga ccc ttc cag gac tgc tct ggc aac cca gtg ccg aac     1488
Asp Arg Leu Arg Pro Phe Gln Asp Cys Ser Gly Asn Pro Val Pro Asn
    400                 405                 410 ttt ggg gat ata acg act gtc act ttt cct gtc aca ccc aac acg ctg     1536
Phe Gly Asp Ile Thr Thr Val Thr Phe Pro Val Thr Pro Asn Thr Leu
415                 420                 425                 430 ccc aat tac cag tct tcc tct tct acc agt gcc ctg tcc aac ggc ttc     1584
Pro Asn Tyr Gln Ser Ser Ser Ser Thr Ser Ala Leu Ser Asn Gly Phe
                435                 440                 445 tac cac ttt ggc agc acc agc tcc agc ccc ccg atc tcc cca gcc tcc     1632
```

```
                Tyr His Phe Gly Ser Thr Ser Ser Pro Ile Ser Pro Ala Ser
                            450                 455                 460 tct gac ctg tca gtc gct ggg tcc ctg ccg gac acc ttc aat gat gcc       1680
Ser Asp Leu Ser Val Ala Gly Ser Leu Pro Asp Thr Phe Asn Asp Ala
            465                 470                 475 tcc ccc tcc ttc ggc ctg cac ccg tcc cca gtc cac gtg tgc acg gag       1728
Ser Pro Ser Phe Gly Leu His Pro Ser Pro Val His Val Cys Thr Glu
    480                 485                 490 gaa agt ctc atg agc agc ctg aat ggg ggc tct gtt cct tct gag ctg       1776
Glu Ser Leu Met Ser Ser Leu Asn Gly Gly Ser Val Pro Ser Glu Leu
495                 500                 505                 510 gat ggg ctg gac tcc gag aag gac aag atg ctg gtg gag aag cag aag       1824
Asp Gly Leu Asp Ser Glu Lys Asp Lys Met Leu Val Glu Lys Gln Lys
                515                 520                 525 gtg atc aat gaa ctc acc tgg aaa ctc cag caa gag cag agg cag gtg       1872
Val Ile Asn Glu Leu Thr Trp Lys Leu Gln Gln Glu Gln Arg Gln Val
            530                 535                 540 gag gag ctg agg atg cag ctt cag aag cag aaa agg aat aac tgt tca       1920
Glu Glu Leu Arg Met Gln Leu Gln Lys Gln Lys Arg Asn Asn Cys Ser
        545                 550                 555 gag aag aag ccg ctg cct ttc ctg gct gcc tcc atc aag cag gaa gag       1968
Glu Lys Lys Pro Leu Pro Phe Leu Ala Ala Ser Ile Lys Gln Glu Glu
    560                 565                 570 gct gtc tcc agc tgt cct ttt gca tcc caa gta cct gtg aaa aga caa       2016
Ala Val Ser Ser Cys Pro Phe Ala Ser Gln Val Pro Val Lys Arg Gln
575                 580                 585                 590 agc agc agc tca gag tgt cac cca ccg gct tgt gaa gct gct caa ctc       2064
Ser Ser Ser Ser Glu Cys His Pro Pro Ala Cys Glu Ala Ala Gln Leu
                595                 600                 605 cag cct ctt gga aat gct cat tgt gtg gag tcc tca gat caa acc aat       2112
Gln Pro Leu Gly Asn Ala His Cys Val Glu Ser Ser Asp Gln Thr Asn
            610                 615                 620 gta ctt tct tcc aca ttt ctc agc ccc cag tgt tcc cct cag cat tca       2160
Val Leu Ser Ser Thr Phe Leu Ser Pro Gln Cys Ser Pro Gln His Ser
        625                 630                 635 ccg ctg ggg gct gtg aaa agc cca cag cac atc agt ttg ccc cca tca       2208
Pro Leu Gly Ala Val Lys Ser Pro Gln His Ile Ser Leu Pro Pro Ser
    640                 645                 650 ccc aac aac cct cac ttt ctg ccc tca tcc tcc ggg gcc cag gga gaa       2256
Pro Asn Asn Pro His Phe Leu Pro Ser Ser Ser Gly Ala Gln Gly Glu
655                 660                 665                 670 ggg cac agg gtc tcc tcg ccc atc agc agc cag gtg tgc act gca cag       2304
Gly His Arg Val Ser Ser Pro Ile Ser Ser Gln Val Cys Thr Ala Gln
                675                 680                 685 atg gct ggt tta cac tct tct gat aag gtg ggg cca aag ttt tca att       2352
Met Ala Gly Leu His Ser Ser Asp Lys Val Gly Pro Lys Phe Ser Ile
            690                 695                 700 cca tcc cca act ttt tct aag tca agt tca gca att tca gag gta aca       2400
Pro Ser Pro Thr Phe Ser Lys Ser Ser Ser Ala Ile Ser Glu Val Thr
        705                 710                 715 cag cct cca tcc tat gaa gat gcc gta aag cag caa atg acc cgg agt       2448
Gln Pro Pro Ser Tyr Glu Asp Ala Val Lys Gln Gln Met Thr Arg Ser
    720                 725                 730 cag cag atg gat gaa ctc ctg gac gtg ctt att gaa agc gga gaa atg       2496
Gln Gln Met Asp Glu Leu Leu Asp Val Leu Ile Glu Ser Gly Glu Met
735                 740                 745                 750 cca gca gac gct aga gag gat cac tca tgt ctt caa aaa gtc cca aag       2544
Pro Ala Asp Ala Arg Glu Asp His Ser Cys Leu Gln Lys Val Pro Lys
                755                 760                 765
```

-continued

| | | |
|---|---|---|
| ata ccc aga tct tcc cga agt cca act gct gtc ctc acc aag ccc tcg | | 2592 |
| Ile Pro Arg Ser Ser Arg Ser Pro Thr Ala Val Leu Thr Lys Pro Ser | | |
| 770 775 780 | | |
| gct tcc ttt gaa caa gcc tct tca ggc agc cag atc ccc ttt gat ccc | | 2640 |
| Ala Ser Phe Glu Gln Ala Ser Ser Gly Ser Gln Ile Pro Phe Asp Pro | | |
| 785 790 795 | | |
| tat gcc acc gac agt gat gag cat ctt gaa gtc tta tta aat tcc cag | | 2688 |
| Tyr Ala Thr Asp Ser Asp Glu His Leu Glu Val Leu Leu Asn Ser Gln | | |
| 800 805 810 | | |
| agc ccc cta gga aag atg agt gat gtc acc ctt cta aaa att ggg agc | | 2736 |
| Ser Pro Leu Gly Lys Met Ser Asp Val Thr Leu Leu Lys Ile Gly Ser | | |
| 815 820 825 830 | | |
| gaa gag cct cac ttt gat ggg ata atg gat gga ttc tct ggg aag gct | | 2784 |
| Glu Glu Pro His Phe Asp Gly Ile Met Asp Gly Phe Ser Gly Lys Ala | | |
| 835 840 845 | | |
| gca gaa gac ctc ttc aat gca cat gag atc ttg cca ggc ccc ctc tct | | 2832 |
| Ala Glu Asp Leu Phe Asn Ala His Glu Ile Leu Pro Gly Pro Leu Ser | | |
| 850 855 860 | | |
| cca atg cag aca cag ttt tca ccc tct tct gtg gac agc aat ggg ctg | | 2880 |
| Pro Met Gln Thr Gln Phe Ser Pro Ser Ser Val Asp Ser Asn Gly Leu | | |
| 865 870 875 | | |
| cag tta agc ttc act gaa tct ccc tgg gaa acc atg gag tgg ctg gac | | 2928 |
| Gln Leu Ser Phe Thr Glu Ser Pro Trp Glu Thr Met Glu Trp Leu Asp | | |
| 880 885 890 | | |
| ctc act ccg cca aat tcc aca cca ggc ttt agc gcc ctc acc acc agc | | 2976 |
| Leu Thr Pro Pro Asn Ser Thr Pro Gly Phe Ser Ala Leu Thr Thr Ser | | |
| 895 900 905 910 | | |
| agc ccc agc atc ttc aac atc gat ttc ctg gat gtc act gat ctc aat | | 3024 |
| Ser Pro Ser Ile Phe Asn Ile Asp Phe Leu Asp Val Thr Asp Leu Asn | | |
| 915 920 925 | | |
| ttg aat tct tcc atg gac ctt cac ttg cag cag tgg tag | | 3063 |
| Leu Asn Ser Ser Met Asp Leu His Leu Gln Gln Trp | | |
| 930 935 | | |

<210> SEQ ID NO 28
<211> LENGTH: 938
<212> TYPE: PRT
<213> ORGANISM: Homo sapiens

<400> SEQUENCE: 28

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

-continued

```
Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
            165                 170                 175

Gly Ser Pro Pro Asp Ala Lys Ala Ser Asp Thr Pro Ser Thr Gly Ser
                180                 185                 190

Leu Gly Thr Asn Gln Asp Leu Ala Ser Gly Ser Glu Asn Asp Arg Asn
            195                 200                 205

Asp Ser Ala Ser Gln Pro Ser His Gln Ser Asp Ala Gly Lys Gln Gly
            210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
                260                 265                 270

Gln Lys Ala Glu Lys Ser Pro Pro Met Asp Ser Ala Tyr Ala Arg
            275                 280                 285

Leu Leu Gln Gln Gln Leu Phe Leu Gln Leu Gln Ile Leu Ser Gln
            290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
                340                 345                 350

Phe Ser Gly Gln Thr Gly Val Ser Ser Phe Lys Pro Gly Pro Leu Pro
            355                 360                 365

Pro Asn Leu Asp Asp Leu Lys Val Ser Glu Leu Arg Gln Gln Leu Arg
370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
                420                 425                 430

Tyr Gln Ser Ser Ser Ser Thr Ser Ala Leu Ser Asn Gly Phe Tyr His
            435                 440                 445

Phe Gly Ser Thr Ser Ser Ser Pro Pro Ile Ser Pro Ala Ser Ser Asp
450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
            485                 490                 495

Leu Met Ser Ser Leu Asn Gly Gly Ser Val Pro Ser Glu Leu Asp Gly
            500                 505                 510

Leu Asp Ser Glu Lys Asp Lys Met Leu Val Glu Lys Gln Lys Val Ile
            515                 520                 525

Asn Glu Leu Thr Trp Lys Leu Gln Gln Glu Arg Gln Val Glu Glu
            530                 535                 540

Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
```

```
                      565                 570                 575
Ser Ser Cys Pro Phe Ala Ser Gln Val Pro Val Lys Arg Gln Ser Ser
            580                 585                 590
Ser Ser Glu Cys His Pro Pro Ala Cys Glu Ala Ala Gln Leu Gln Pro
        595                 600                 605
Leu Gly Asn Ala His Cys Val Glu Ser Ser Asp Gln Thr Asn Val Leu
    610                 615                 620
Ser Ser Thr Phe Leu Ser Pro Gln Cys Ser Pro Gln His Ser Pro Leu
625                 630                 635                 640
Gly Ala Val Lys Ser Pro Gln His Ile Ser Leu Pro Pro Ser Pro Asn
                645                 650                 655
Asn Pro His Phe Leu Pro Ser Ser Gly Ala Gln Gly Glu Gly His
            660                 665                 670
Arg Val Ser Ser Pro Ile Ser Ser Gln Val Cys Thr Ala Gln Met Ala
        675                 680                 685
Gly Leu His Ser Ser Asp Lys Val Gly Pro Lys Phe Ser Ile Pro Ser
    690                 695                 700
Pro Thr Phe Ser Lys Ser Ser Ala Ile Ser Glu Val Thr Gln Pro
705                 710                 715                 720
Pro Ser Tyr Glu Asp Ala Val Lys Gln Gln Met Thr Arg Ser Gln Gln
                725                 730                 735
Met Asp Glu Leu Leu Asp Val Leu Ile Glu Ser Gly Glu Met Pro Ala
            740                 745                 750
Asp Ala Arg Glu Asp His Ser Cys Leu Gln Lys Val Pro Lys Ile Pro
        755                 760                 765
Arg Ser Ser Arg Ser Pro Thr Ala Val Leu Thr Lys Pro Ser Ala Ser
    770                 775                 780
Phe Glu Gln Ala Ser Ser Gly Ser Gln Ile Pro Phe Asp Pro Tyr Ala
785                 790                 795                 800
Thr Asp Ser Asp Glu His Leu Glu Val Leu Leu Asn Ser Gln Ser Pro
                805                 810                 815
Leu Gly Lys Met Ser Asp Val Thr Leu Leu Lys Ile Gly Ser Glu Glu
            820                 825                 830
Pro His Phe Asp Gly Ile Met Asp Gly Phe Ser Gly Lys Ala Ala Glu
        835                 840                 845
Asp Leu Phe Asn Ala His Glu Ile Leu Pro Gly Pro Leu Ser Pro Met
    850                 855                 860
Gln Thr Gln Phe Ser Pro Ser Ser Val Asp Ser Asn Gly Leu Gln Leu
865                 870                 875                 880
Ser Phe Thr Glu Ser Pro Trp Glu Thr Met Glu Trp Leu Asp Leu Thr
                885                 890                 895
Pro Pro Asn Ser Thr Pro Gly Phe Ser Ala Leu Thr Thr Ser Ser Pro
            900                 905                 910
Ser Ile Phe Asn Ile Asp Phe Leu Asp Val Thr Asp Leu Asn Leu Asn
        915                 920                 925
Ser Ser Met Asp Leu His Leu Gln Gln Trp
    930                 935

<210> SEQ ID NO 29
<211> LENGTH: 938
<212> TYPE: PRT
<213> ORGANISM: Homo sapiens

<400> SEQUENCE: 29
```

-continued

```
Met Thr Leu Leu Gly Ser Glu His Ser Leu Leu Ile Arg Ser Lys Phe
 1               5                  10                  15

Arg Ser Val Leu Gln Leu Arg Leu Gln Gln Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
 65                 70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
        275                 280                 285

Leu Leu Gln Gln Gln Gln Leu Phe Leu Gln Leu Gln Ile Leu Ser Gln
    290                 295                 300

Gln Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
        355                 360                 365

Pro Asn Leu Asp Asp Leu Lys Val Ser Glu Leu Arg Gln Gln Leu Arg
    370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
```

-continued

```
                420                 425                 430
Tyr Gln Ser Ser Ser Thr Ser Ala Leu Ser Asn Gly Phe Tyr His
            435                 440                 445
Phe Gly Ser Thr Ser Ser Ser Pro Ile Ser Pro Ala Ser Ser Asp
450                 455                 460
Leu Ser Val Ala Gly Ser Leu Pro Asp Thr Phe Asn Asp Ala Ser Pro
465                 470                 475                 480
Ser Phe Gly Leu His Pro Ser Pro Val His Val Cys Thr Glu Glu Ser
                485                 490                 495
Leu Met Ser Ser Leu Asn Gly Gly Ser Val Pro Ser Glu Leu Asp Gly
            500                 505                 510
Leu Asp Ser Glu Lys Asp Lys Met Leu Val Glu Lys Gln Lys Val Ile
            515                 520                 525
Asn Glu Leu Thr Trp Lys Leu Gln Gln Glu Gln Arg Gln Val Glu Glu
            530                 535                 540
Leu Arg Met Gln Leu Gln Lys Gln Lys Arg Asn Asn Cys Ser Glu Lys
545                 550                 555                 560
Lys Pro Leu Pro Phe Leu Ala Ala Ser Ile Lys Gln Glu Glu Ala Val
                565                 570                 575
Ser Ser Cys Pro Phe Ala Ser Gln Val Pro Val Lys Arg Gln Ser Ser
            580                 585                 590
Ser Ser Glu Cys His Pro Pro Ala Cys Glu Ala Ala Gln Leu Gln Pro
            595                 600                 605
Leu Gly Asn Ala His Cys Val Glu Ser Ser Asp Gln Thr Asn Val Leu
            610                 615                 620
Ser Ser Thr Phe Leu Ser Pro Gln Cys Ser Pro Gln His Ser Pro Leu
625                 630                 635                 640
Gly Ala Val Lys Ser Pro Gln His Ile Ser Leu Pro Pro Ser Pro Asn
                645                 650                 655
Asn Pro His Phe Leu Pro Ser Ser Gly Ala Gln Gly Glu Gly His
            660                 665                 670
Arg Val Ser Ser Pro Ile Ser Ser Gln Val Cys Thr Ala Gln Met Ala
            675                 680                 685
Gly Leu His Ser Ser Asp Lys Val Gly Pro Lys Phe Ser Ile Pro Ser
            690                 695                 700
Pro Thr Phe Ser Lys Ser Ser Ala Ile Ser Glu Val Thr Gln Pro
705                 710                 715                 720
Pro Ser Tyr Glu Asp Ala Val Lys Gln Gln Met Thr Arg Ser Gln Gln
                725                 730                 735
Met Asp Glu Leu Leu Asp Val Leu Ile Glu Ser Gly Glu Met Pro Ala
            740                 745                 750
Asp Ala Arg Glu Asp His Ser Cys Leu Gln Lys Val Pro Lys Ile Pro
            755                 760                 765
Arg Ser Ser Arg Ser Pro Thr Ala Val Leu Thr Lys Pro Ser Ala Ser
            770                 775                 780
Phe Glu Gln Ala Ser Ser Gly Ser Gln Ile Pro Phe Asp Pro Tyr Ala
785                 790                 795                 800
Thr Asp Ser Asp Glu His Leu Glu Val Leu Leu Asn Ser Gln Ser Pro
                805                 810                 815
Leu Gly Lys Met Ser Asp Val Thr Leu Leu Lys Ile Gly Ser Glu Glu
            820                 825                 830
Pro His Phe Asp Gly Ile Met Asp Gly Phe Ser Gly Lys Ala Ala Glu
            835                 840                 845
```

```
Asp Leu Phe Asn Ala His Glu Ile Leu Pro Gly Pro Leu Ser Pro Met
    850                 855                 860

Gln Thr Gln Phe Ser Pro Ser Val Asp Ser Asn Gly Leu Gln Leu
865                 870                 875                 880

Ser Phe Thr Glu Ser Pro Trp Glu Thr Met Glu Trp Leu Asp Leu Thr
                885                 890                 895

Pro Pro Asn Ser Thr Pro Gly Phe Ser Ala Leu Thr Thr Ser Ser Pro
                900                 905                 910

Ser Ile Phe Asn Ile Asp Phe Leu Asp Val Thr Asp Leu Asn Leu Asn
        915                 920                 925

Ser Ser Met Asp Leu His Leu Gln Gln Trp
930                 935

<210> SEQ ID NO 30
<211> LENGTH: 4960
<212> TYPE: DNA
<213> ORGANISM: Mus musculus
<220> FEATURE:
<221> NAME/KEY: CDS
<222> LOCATION: (258)..(3062)

<400> SEQUENCE: 30
ggaattcggc acgaggccac cctcagagga ggagggtcct gcctgctggg agttaattag      60
cctcgcgagc ggcgaggggg gaggcgccag ttttctgggg acactggcgg ccactgtgcg     120
tcctcctacc caagggagct ccccaagagt tggatgaatt ctgggttgtt agctgctgtc     180
ctctgggctc ccgggagcca gtttctggtg aaagcgggg cgcctggcca acgaccagcg      240
gcttgctgag actcacc atg aca ctc ctg ggg tct gaa cac tct ttg ctg        290
                   Met Thr Leu Leu Gly Ser Glu His Ser Leu Leu
                    1               5                   10 att aga agg aag ttc cga tca gtc tta cag tta cgg ctt caa cag aga      338
Ile Arg Arg Lys Phe Arg Ser Val Leu Gln Leu Arg Leu Gln Gln Arg
            15                  20                  25 agg acc cag gag cag ctg gct aac caa ggc tta ata ccg cca ctg aaa      386
Arg Thr Gln Glu Gln Leu Ala Asn Gln Gly Leu Ile Pro Pro Leu Lys
        30                  35                  40 ggt cca act gaa ttc cat gac ccg aga aaa caa ttg gat agt gcc aag      434
Gly Pro Thr Glu Phe His Asp Pro Arg Lys Gln Leu Asp Ser Ala Lys
    45                  50                  55 act gaa gat tcc ctg agg cgc aag ggc aga aac agg tcc gac cgt gcc      482
Thr Glu Asp Ser Leu Arg Arg Lys Gly Arg Asn Arg Ser Asp Arg Ala
60                  65                  70                  75 agc ctg gtt act atg cac att ctc caa gcc tcc acg gca gaa agg tcc      530
Ser Leu Val Thr Met His Ile Leu Gln Ala Ser Thr Ala Glu Arg Ser
                80                  85                  90 att cca act gct cag atg aag ctc aaa aga gcc cgc ctt gca gat gac      578
Ile Pro Thr Ala Gln Met Lys Leu Lys Arg Ala Arg Leu Ala Asp Asp
            95                  100                 105 ctc aat gag aag atc gct ctc cgc caa ggg ccc ttg gaa ctg gtg gag      626
Leu Asn Glu Lys Ile Ala Leu Arg Gln Gly Pro Leu Glu Leu Val Glu
        110                 115                 120 aag aac att ctg ccg atg gat tct tcc gtg aaa gag gct ata aaa ggt      674
Lys Asn Ile Leu Pro Met Asp Ser Ser Val Lys Glu Ala Ile Lys Gly
    125                 130                 135 act gag gtg agc ctc tcc aag gca gca gat gca ttc gcc ttt gag gat      722
Thr Glu Val Ser Leu Ser Lys Ala Ala Asp Ala Phe Ala Phe Glu Asp
140                 145                 150                 155 gac agc agt aga gat ggg ctc tct cca gat cag gct agg agc gag gac      770
```

```
                    -continued

Asp Ser Ser Arg Asp Gly Leu Ser Pro Asp Gln Ala Arg Ser Glu Asp
            160                 165                 170 ccc cag ggc tct aca gga tcc acc cca gac atc aaa tcc act gag gct       818
Pro Gln Gly Ser Thr Gly Ser Thr Pro Asp Ile Lys Ser Thr Glu Ala
            175                 180                 185 cct ctg gac aca atc cag gat ctc act cct ggc tca gaa agt gac aag       866
Pro Leu Asp Thr Ile Gln Asp Leu Thr Pro Gly Ser Glu Ser Asp Lys
            190                 195                 200 aat gat gca gcc tcc cag cca ggc aac cag tca gac cct ggg aag cag       914
Asn Asp Ala Ala Ser Gln Pro Gly Asn Gln Ser Asp Pro Gly Lys Gln
            205                 210                 215 gtt ctc ggc ccc ctc agc acc ccg att cct gtg cac act gct gta aag       962
Val Leu Gly Pro Leu Ser Thr Pro Ile Pro Val His Thr Ala Val Lys
220                 225                 230                 235 tcc aag tct ttg ggt gac agt aag aac cgc cac aaa aag ccc aaa gac      1010
Ser Lys Ser Leu Gly Asp Ser Lys Asn Arg His Lys Lys Pro Lys Asp
                240                 245                 250 ccc aaa cca aag gtg aag aag ctc aaa tac cat cag tac atc ccc cca      1058
Pro Lys Pro Lys Val Lys Lys Leu Lys Tyr His Gln Tyr Ile Pro Pro
            255                 260                 265 gac cag aag gca gag aag tct ccc cca ccc atg gac tct gcc tat gcc      1106
Asp Gln Lys Ala Glu Lys Ser Pro Pro Pro Met Asp Ser Ala Tyr Ala
            270                 275                 280 cgg ctg ctc cag caa cag cag cta ttc ctg cag cta cag atc ctc agc      1154
Arg Leu Leu Gln Gln Gln Gln Leu Phe Leu Gln Leu Gln Ile Leu Ser
            285                 290                 295 cag cag cag caa cag cag cag caa cag cag cag caa cag cag cag          1202
Gln Gln Gln Gln Gln Gln Gln Gln Gln Gln Gln Gln Gln Gln Gln
300                 305                 310                 315 cag cag cag cag cag cgg ttc agc tac cct ggg atg cac caa aca cac      1250
Gln Gln Gln Gln Gln Arg Phe Ser Tyr Pro Gly Met His Gln Thr His
            320                 325                 330 ctc aaa gaa cca aat gaa cag atg gcc aga aat ccg aat cct tct tca      1298
Leu Lys Glu Pro Asn Glu Gln Met Ala Arg Asn Pro Asn Pro Ser Ser
                335                 340                 345 aca cca ctg agc aat acc cct cta tcc cct gtc aaa aat agc att tct      1346
Thr Pro Leu Ser Asn Thr Pro Leu Ser Pro Val Lys Asn Ser Ile Ser
            350                 355                 360 gga caa act ggt gtt tct tct ctc aaa cca ggc ccc ctc cca ccc aac      1394
Gly Gln Thr Gly Val Ser Ser Leu Lys Pro Gly Pro Leu Pro Pro Asn
            365                 370                 375 ctg gat gat ctc aag gtg tca gag tta aga caa cag ctt cga atc cgg      1442
Leu Asp Asp Leu Lys Val Ser Glu Leu Arg Gln Gln Leu Arg Ile Arg
380                 385                 390                 395 ggc ttg cca gtg tca ggc acc aag aca gcg ctg gtg gac cgg ctt cgt      1490
Gly Leu Pro Val Ser Gly Thr Lys Thr Ala Leu Val Asp Arg Leu Arg
                400                 405                 410 ccc ttc cag gat tgt gct ggc aac cct gtg ccc aac ttt ggg gac atc      1538
Pro Phe Gln Asp Cys Ala Gly Asn Pro Val Pro Asn Phe Gly Asp Ile
            415                 420                 425 aca act gtc acc ttt cct gtc acg ccc aac acc ttg ccc agt tat cag      1586
Thr Thr Val Thr Phe Pro Val Thr Pro Asn Thr Leu Pro Ser Tyr Gln
            430                 435                 440 tcc tcc ccg aca ggc ttc tac cac ttt ggc agc aca agc tcc agc cca      1634
Ser Ser Pro Thr Gly Phe Tyr His Phe Gly Ser Thr Ser Ser Ser Pro
            445                 450                 455 ccc atc tcc ccc gcc tca tct gac ttg tcc gct gca ggg tcc ctg cca      1682
Pro Ile Ser Pro Ala Ser Ser Asp Leu Ser Ala Ala Gly Ser Leu Pro
460                 465                 470                 475
```

-continued

```
gac acc ttc acc gat gcg tca cct ggc ttc ggc ctg cac gca tct ccg    1730
Asp Thr Phe Thr Asp Ala Ser Pro Gly Phe Gly Leu His Ala Ser Pro
                480                 485                 490 gtg ccc gcc tgc acg gac gag agt ctg ctg agc agc ctg aat ggg ggc    1778
Val Pro Ala Cys Thr Asp Glu Ser Leu Leu Ser Ser Leu Asn Gly Gly
            495                 500                 505 tcg ggc ccc tcc gag cct gat ggg cta gac tct gag aag gac aag atg    1826
Ser Gly Pro Ser Glu Pro Asp Gly Leu Asp Ser Glu Lys Asp Lys Met
        510                 515                 520 ctg gtg gag aag cag aaa gtg atc aac cag ctc acc tgg aag ctg cgg    1874
Leu Val Glu Lys Gln Lys Val Ile Asn Gln Leu Thr Trp Lys Leu Arg
525                 530                 535 caa gag cag cgg cag gtg gaa gag ctg aga atg caa ctg cag aag cag    1922
Gln Glu Gln Arg Gln Val Glu Glu Leu Arg Met Gln Leu Gln Lys Gln
540                 545                 550                 555 aag agc agc tgc agc gac cag aag cca ctg ccc ttc ttg gcc acc acc    1970
Lys Ser Ser Cys Ser Asp Gln Lys Pro Leu Pro Phe Leu Ala Thr Thr
                560                 565                 570 atc aaa cag gaa gat gtc tcc agc tgc ccc ttc gca ccc cag cag gcg    2018
Ile Lys Gln Glu Asp Val Ser Ser Cys Pro Phe Ala Pro Gln Gln Ala
            575                 580                 585 tct ggg aag gga cag ggc cac agc tct gac agt ccc cct ccg gct tgt    2066
Ser Gly Lys Gly Gln Gly His Ser Ser Asp Ser Pro Pro Pro Ala Cys
        590                 595                 600 gag acg gct cag ctg ctg cct cac tgt gtg gag tcc tca ggt caa acc    2114
Glu Thr Ala Gln Leu Leu Pro His Cys Val Glu Ser Ser Gly Gln Thr
605                 610                 615 cat gta ctc tcg tcc acg ttt ctc agc ccc cag tgc tcc cct cag cac    2162
His Val Leu Ser Ser Thr Phe Leu Ser Pro Gln Cys Ser Pro Gln His
620                 625                 630                 635 tcg ccc ctg ggg ggc ctg aag agc ccg cag cac atc agc ctg cct cca    2210
Ser Pro Leu Gly Gly Leu Lys Ser Pro Gln His Ile Ser Leu Pro Pro
                640                 645                 650 tca ccc aac aac cat tac ttc ctg gct tcc tct tcg gga gct cag aga    2258
Ser Pro Asn Asn His Tyr Phe Leu Ala Ser Ser Ser Gly Ala Gln Arg
            655                 660                 665 gag aac cat ggg gtc tct tca ccc agc agc agc caa ggg tgc gca cag    2306
Glu Asn His Gly Val Ser Ser Pro Ser Ser Ser Gln Gly Cys Ala Gln
        670                 675                 680 atg act ggt tta caa tct tct gac aag gtg ggg cca acg ttt tca att    2354
Met Thr Gly Leu Gln Ser Ser Asp Lys Val Gly Pro Thr Phe Ser Ile
685                 690                 695 cca tcc cca act ttt tct aag tca agt tca gca gtt tca gat atc acc    2402
Pro Ser Pro Thr Phe Ser Lys Ser Ser Ser Ala Val Ser Asp Ile Thr
700                 705                 710                 715 cag ccc cca tcc tat gaa gat gca gtg aag cag caa atg act cgg agt    2450
Gln Pro Pro Ser Tyr Glu Asp Ala Val Lys Gln Gln Met Thr Arg Ser
                720                 725                 730 cag cag atg gac gaa ctc ctg gat gtc ctc att gaa agt gga gaa atg    2498
Gln Gln Met Asp Glu Leu Leu Asp Val Leu Ile Glu Ser Gly Glu Met
            735                 740                 745 cca gcc gat gcc agg gaa gat cat tca tgt ctt cag aaa att cca aag    2546
Pro Ala Asp Ala Arg Glu Asp His Ser Cys Leu Gln Lys Ile Pro Lys
        750                 755                 760 atc cct ggg tcc tcc tgc agc cca act gcc atc ccc ccg aag ccc tcg    2594
Ile Pro Gly Ser Ser Cys Ser Pro Thr Ala Ile Pro Pro Lys Pro Ser
765                 770                 775 gct tcc ttt gag cag gca tct tcg gga ggc cag atg gcc ttc gat cac    2642
Ala Ser Phe Glu Gln Ala Ser Ser Gly Gly Gln Met Ala Phe Asp His
780                 785                 790                 795
```

-continued

| | |
|---|---|
| tac gcc aac gac agt gac gaa cac ctg gaa gtc tta ttg aat tct cac<br>Tyr Ala Asn Asp Ser Asp Glu His Leu Glu Val Leu Leu Asn Ser His<br>800                      805                    810 | 2690 |
| agc ccc atc gga aag gtg agc gat gtt acc ctc ctc aaa atc gga agc<br>Ser Pro Ile Gly Lys Val Ser Asp Val Thr Leu Leu Lys Ile Gly Ser<br>815                      820                    825 | 2738 |
| gag gag cct cct ttt gac agc atc atg gat ggc ttc cca ggg aag gct<br>Glu Glu Pro Pro Phe Asp Ser Ile Met Asp Gly Phe Pro Gly Lys Ala<br>830                      835                    840 | 2786 |
| gcg gaa gat ctc ttc agt gct cac gag ctc ttg cct ggg ccc ctc tcc<br>Ala Glu Asp Leu Phe Ser Ala His Glu Leu Leu Pro Gly Pro Leu Ser<br>845                      850                    855 | 2834 |
| ccg atg cat gca cag ttg tca cct cct tct gtg gac agc agt ggt ctg<br>Pro Met His Ala Gln Leu Ser Pro Pro Ser Val Asp Ser Ser Gly Leu<br>860                      865                    870                    875 | 2882 |
| cag ctg agc ttc acg gaa tct cct tgg gaa aca atg gaa tgg ctg gac<br>Gln Leu Ser Phe Thr Glu Ser Pro Trp Glu Thr Met Glu Trp Leu Asp<br>880                      885                    890 | 2930 |
| ctc act cca cct agt tcc acg cca ggc ttc agc aac ctt acc tcc agt<br>Leu Thr Pro Pro Ser Ser Thr Pro Gly Phe Ser Asn Leu Thr Ser Ser<br>895                      900                    905 | 2978 |
| ggg ccc agc att ttc aac atc gat ttt ctg gat gtt aca gat ctt aat<br>Gly Pro Ser Ile Phe Asn Ile Asp Phe Leu Asp Val Thr Asp Leu Asn<br>910                      915                    920 | 3026 |
| ctg aat tcc cct atg gat ctc cac tta cag cag tgg taaacaccg<br>Leu Asn Ser Pro Met Asp Leu His Leu Gln Gln Trp<br>925                      930                    935 | 3072 |
| aggtacaaga gctacgagag ctcagtggga attcaatgga ggaaagcacg ataccggaaa | 3132 |
| tgtgtgttcc aaaagatgaa ggggggaaaa tggggaggga aaaaaaaaaa cagcaacgga | 3192 |
| ggttttgtg acaactaacc agaacaaaca gaagtcagct attaaaatat gtctaaatgt | 3252 |
| aatatctacc agcattcagt aactgttaat aacttcagtg atgcattcaa aaatgtgctt | 3312 |
| tgtcagaata agaatgccaa aaatgttttt tcgctgcctt atctcatacc agttttttg | 3372 |
| ggttttttt tgtttgtttg tttttggtt tttttttttt tgtgtgtgtt gttatttggt | 3432 |
| tttcttttg cccacagttt gtctcaggca atactgggac ataggctgac cccattagct | 3492 |
| tttgttatga atttactaaa ctttctgtgg aaggagaaca gagcctctgc cgcgggtgtg | 3552 |
| gggaagccat cctgtgcttg aggcagcaca cgtgtgtcca tcatcatcag tcagaagagc | 3612 |
| agggcctgtc tcacccaatc gagtccttaa gacagaataa tcagaatggt cagagggaca | 3672 |
| gaccaatcaa ttcccaggaa agcaaaagtg actcaatgtc ccttgactcc caaatggtcc | 3732 |
| cactggactg gtgatcactg gtgacaacta actagctttg tccagagaat ccacccagaa | 3792 |
| cacggtgctt tttagccagt agtccacctc tatgtgcatc agcaatgcat agcaggtgag | 3852 |
| aacttgaatc acagaaactt catgccatgg atggagactc ctgaggcgct caaatactac | 3912 |
| tacctctagt tccaaagact agagctagat gatcagaaag gcaactggag gcccagggag | 3972 |
| ccgtactggg acaagttaga attagagaac gatgtcattt aacattccga gaaagaaata | 4032 |
| accatgaatt gctattacag gagtaacaca cagggccagc ttcttttttc ttctttttta | 4092 |
| tttttcttt cttattgtga gcagagggaa ttcacctcag ttcatctttc tctcagtact | 4152 |
| tttctttcaa gatatcaatc ctttatgact cttttgcttt taattctctc tctctctctc | 4212 |
| tctctctctc tctctctttc tctcaaagga gaggtttcag ttctaacaag ctaccatagt | 4272 |
| cctattaaag ccatttttttt ttttagaata ttaaaagtcc aaactctctt gccaaactct | 4332 |

-continued

```
ttcttcacat gcgcattggc tgaaaacaga atttacaaga atttctttag gaagaaactg    4392
gggatgtggc ccattggtca caaagttttt ttgtttgttt ttgttttgt ttcaattctt    4452 gtttgattta tggacaatct ttggtttgta ttgctctgga gaaattggaa atcattgcag    4512
agtgaagata aatcagggca ccatgtatag tagagaatgt ttcagtagtt ttccaaacga    4572
gaacacaatt gcacactgta acaacagga gtgtgaagga ccacagtctt gaggagttct    4632
tgttgccctg tgtttggtga aggcgttggg gaccgaggag acaacatac agtttggcca    4692 aggctctcag aggcttgctg tggcgccaat tcaagtatta caatgttgca tgctgtagaa    4752
agtagctgtt gctgttgttt tgttttgttt taatttaagt caccaaggca ctgttttatt    4812
cttttgtaaa aaaaaaaaa gttcactgtg cacttataga gaaataatc aacaatgttg    4872 tgaattttg agaagacttt ttttttttg ataaaccaaa gatttagaaa tcattccatt    4932
gtcaacttgt aaaaaaaaaa aaaaaaa                                      4960
```

<210> SEQ ID NO 31
<211> LENGTH: 935
<212> TYPE: PRT
<213> ORGANISM: Mus musculus

<400> SEQUENCE: 31

```
Met Thr Leu Leu Gly Ser Glu His Ser Leu Leu Ile Arg Arg Lys Phe
  1               5                  10                  15

Arg Ser Val Leu Gln Leu Arg Leu Gln Gln Arg Thr Gln Glu Gln
             20                  25                  30

Leu Ala Asn Gln Gly Leu Ile Pro Pro Leu Lys Gly Pro Thr Glu Phe
         35                  40                  45

His Asp Pro Arg Lys Gln Leu Asp Ser Ala Lys Thr Glu Asp Ser Leu
     50                  55                  60

Arg Arg Lys Gly Arg Asn Arg Ser Asp Arg Ala Ser Leu Val Thr Met
 65                  70                  75                  80

His Ile Leu Gln Ala Ser Thr Ala Glu Arg Ser Ile Pro Thr Ala Gln
                 85                  90                  95

Met Lys Leu Lys Arg Ala Arg Leu Ala Asp Asp Leu Asn Glu Lys Ile
            100                 105                 110

Ala Leu Arg Gln Gly Pro Leu Glu Leu Val Glu Lys Asn Ile Leu Pro
        115                 120                 125

Met Asp Ser Ser Val Lys Glu Ala Ile Lys Gly Thr Glu Val Ser Leu
    130                 135                 140

Ser Lys Ala Ala Asp Ala Phe Ala Phe Glu Asp Asp Ser Ser Arg Asp
145                 150                 155                 160

Gly Leu Ser Pro Asp Gln Ala Arg Ser Glu Asp Pro Gln Gly Ser Thr
                165                 170                 175

Gly Ser Thr Pro Asp Ile Lys Ser Thr Glu Ala Pro Leu Asp Thr Ile
            180                 185                 190

Gln Asp Leu Thr Pro Gly Ser Glu Ser Asp Lys Asn Asp Ala Ala Ser
        195                 200                 205

Gln Pro Gly Asn Gln Ser Asp Pro Gly Lys Gln Val Leu Gly Pro Leu
    210                 215                 220

Ser Thr Pro Ile Pro Val His Thr Ala Val Lys Ser Lys Ser Leu Gly
225                 230                 235                 240

Asp Ser Lys Asn Arg His Lys Lys Pro Lys Asp Pro Lys Pro Lys Val
                245                 250                 255

Lys Lys Leu Lys Tyr His Gln Tyr Ile Pro Pro Asp Gln Lys Ala Glu
```

-continued

```
                260                 265                 270
Lys Ser Pro Pro Met Asp Ser Ala Tyr Ala Arg Leu Leu Gln Gln
        275                 280                 285
Gln Gln Leu Phe Leu Gln Leu Gln Ile Leu Ser Gln Gln Gln Gln
        290                 295                 300
Gln Gln Gln Gln Gln Gln Gln Gln Gln Gln Gln Gln Gln Gln Gln
305                 310                 315                 320
Arg Phe Ser Tyr Pro Gly Met His Gln Thr His Leu Lys Glu Pro Asn
                325                 330                 335
Glu Gln Met Ala Arg Asn Pro Asn Pro Ser Ser Thr Pro Leu Ser Asn
        340                 345                 350
Thr Pro Leu Ser Pro Val Lys Asn Ser Ile Ser Gly Gln Thr Gly Val
        355                 360                 365
Ser Ser Leu Lys Pro Gly Pro Leu Pro Pro Asn Leu Asp Asp Leu Lys
        370                 375                 380
Val Ser Glu Leu Arg Gln Gln Leu Arg Ile Arg Gly Leu Pro Val Ser
385                 390                 395                 400
Gly Thr Lys Thr Ala Leu Val Asp Arg Leu Arg Pro Phe Gln Asp Cys
                405                 410                 415
Ala Gly Asn Pro Val Pro Asn Phe Gly Asp Ile Thr Thr Val Thr Phe
                420                 425                 430
Pro Val Thr Pro Asn Thr Leu Pro Ser Tyr Gln Ser Ser Pro Thr Gly
        435                 440                 445
Phe Tyr His Phe Gly Ser Thr Ser Ser Ser Pro Pro Ile Ser Pro Ala
        450                 455                 460
Ser Ser Asp Leu Ser Ala Ala Gly Ser Leu Pro Asp Thr Phe Thr Asp
465                 470                 475                 480
Ala Ser Pro Gly Phe Gly Leu His Ala Ser Pro Val Pro Ala Cys Thr
                485                 490                 495
Asp Glu Ser Leu Leu Ser Ser Leu Asn Gly Gly Ser Gly Pro Ser Glu
                500                 505                 510
Pro Asp Gly Leu Asp Ser Glu Lys Asp Lys Met Leu Val Glu Lys Gln
        515                 520                 525
Lys Val Ile Asn Gln Leu Thr Trp Lys Leu Arg Gln Glu Gln Arg Gln
        530                 535                 540
Val Glu Glu Leu Arg Met Gln Leu Gln Lys Gln Lys Ser Ser Cys Ser
545                 550                 555                 560
Asp Gln Lys Pro Leu Pro Phe Leu Ala Thr Thr Ile Lys Gln Glu Asp
                565                 570                 575
Val Ser Ser Cys Pro Phe Ala Pro Gln Gln Ala Ser Gly Lys Gly Gln
                580                 585                 590
Gly His Ser Ser Asp Ser Pro Pro Ala Cys Glu Thr Ala Gln Leu
        595                 600                 605
Leu Pro His Cys Val Glu Ser Ser Gly Gln Thr His Val Leu Ser Ser
        610                 615                 620
Thr Phe Leu Ser Pro Gln Cys Ser Pro Gln His Ser Pro Leu Gly Gly
625                 630                 635                 640
Leu Lys Ser Pro Gln His Ile Ser Leu Pro Pro Ser Pro Asn Asn His
                645                 650                 655
Tyr Phe Leu Ala Ser Ser Ser Gly Ala Gln Arg Glu Asn His Gly Val
                660                 665                 670
Ser Ser Pro Ser Ser Ser Gln Gly Cys Ala Gln Met Thr Gly Leu Gln
        675                 680                 685
```

```
Ser Ser Asp Lys Val Gly Pro Thr Phe Ser Ile Pro Ser Pro Thr Phe
    690                 695                 700
Ser Lys Ser Ser Ser Ala Val Ser Asp Ile Thr Gln Pro Pro Ser Tyr
705                 710                 715                 720
Glu Asp Ala Val Lys Gln Gln Met Thr Arg Ser Gln Gln Met Asp Glu
                    725                 730                 735
Leu Leu Asp Val Leu Ile Glu Ser Gly Glu Met Pro Ala Asp Ala Arg
                740                 745                 750
Glu Asp His Ser Cys Leu Gln Lys Ile Pro Lys Ile Pro Gly Ser Ser
            755                 760                 765
Cys Ser Pro Thr Ala Ile Pro Pro Lys Pro Ser Ala Ser Phe Glu Gln
    770                 775                 780
Ala Ser Ser Gly Gly Gln Met Ala Phe Asp His Tyr Ala Asn Asp Ser
785                 790                 795                 800
Asp Glu His Leu Glu Val Leu Leu Asn Ser His Ser Pro Ile Gly Lys
                805                 810                 815
Val Ser Asp Val Thr Leu Leu Lys Ile Gly Ser Glu Pro Pro Phe
                820                 825                 830
Asp Ser Ile Met Asp Gly Phe Pro Gly Lys Ala Ala Glu Asp Leu Phe
            835                 840                 845
Ser Ala His Glu Leu Leu Pro Gly Pro Leu Ser Pro Met His Ala Gln
    850                 855                 860
Leu Ser Pro Pro Ser Val Asp Ser Ser Gly Leu Gln Leu Ser Phe Thr
865                 870                 875                 880
Glu Ser Pro Trp Glu Thr Met Glu Trp Leu Asp Leu Thr Pro Pro Ser
                885                 890                 895
Ser Thr Pro Gly Phe Ser Asn Leu Thr Ser Ser Gly Pro Ser Ile Phe
            900                 905                 910
Asn Ile Asp Phe Leu Asp Val Thr Asp Leu Asn Leu Asn Ser Pro Met
    915                 920                 925
Asp Leu His Leu Gln Gln Trp
    930                 935

<210> SEQ ID NO 32
<211> LENGTH: 935
<212> TYPE: PRT
<213> ORGANISM: Mus musculus

<400> SEQUENCE: 32

Met Thr Leu Leu Gly Ser Glu His Ser Leu Leu Ile Arg Arg Lys Phe
 1               5                  10                  15
Arg Ser Val Leu Gln Leu Arg Leu Gln Gln Arg Arg Thr Gln Glu Gln
                20                  25                  30
Leu Ala Asn Gln Gly Leu Ile Pro Pro Leu Lys Gly Pro Thr Glu Phe
            35                  40                  45
His Asp Pro Arg Lys Gln Leu Asp Ser Ala Lys Thr Glu Asp Ser Leu
    50                  55                  60
Arg Arg Lys Gly Arg Asn Arg Ser Asp Arg Ala Ser Leu Val Thr Met
65                  70                  75                  80
His Ile Leu Gln Ala Ser Thr Ala Glu Arg Ser Ile Pro Thr Ala Gln
                85                  90                  95
Met Lys Leu Lys Arg Ala Arg Leu Ala Asp Asp Leu Asn Glu Lys Ile
                100                 105                 110
Ala Leu Arg Gln Gly Pro Leu Glu Leu Val Glu Lys Asn Ile Leu Pro
```

-continued

```
            115                 120                 125
Met Asp Ser Ser Val Lys Glu Ala Ile Lys Gly Thr Glu Val Ser Leu
    130                 135                 140

Ser Lys Ala Ala Asp Ala Phe Ala Phe Glu Asp Ser Ser Arg Asp
145                 150                 155                 160

Gly Leu Ser Pro Asp Gln Ala Arg Ser Glu Asp Pro Gln Gly Ser Thr
                165                 170                 175

Gly Ser Thr Pro Asp Ile Lys Ser Thr Glu Ala Pro Leu Asp Thr Ile
                180                 185                 190

Gln Asp Leu Thr Pro Gly Ser Glu Ser Asp Lys Asn Asp Ala Ala Ser
            195                 200                 205

Gln Pro Gly Asn Gln Ser Asp Pro Gly Lys Gln Val Leu Gly Pro Leu
    210                 215                 220

Ser Thr Pro Ile Pro Val His Thr Ala Val Lys Ser Lys Ser Leu Gly
225                 230                 235                 240

Asp Ser Lys Asn Arg His Lys Lys Pro Lys Asp Pro Lys Pro Lys Val
                245                 250                 255

Lys Lys Leu Lys Tyr His Gln Tyr Ile Pro Pro Asp Gln Lys Ala Glu
                260                 265                 270

Lys Ser Pro Pro Pro Met Asp Ser Ala Tyr Ala Arg Leu Leu Gln Gln
    275                 280                 285

Gln Gln Leu Phe Leu Gln Leu Gln Ile Leu Ser Gln Gln Gln Gln Gln
    290                 295                 300

Gln Gln Gln Gln Gln Gln Gln Gln Gln Gln Gln Gln Gln Gln Gln Gln
305                 310                 315                 320

Arg Phe Ser Tyr Pro Gly Met His Gln Thr His Leu Lys Glu Pro Asn
                325                 330                 335

Glu Gln Met Ala Arg Asn Pro Asn Pro Ser Ser Thr Pro Leu Ser Asn
                340                 345                 350

Thr Pro Leu Ser Pro Val Lys Asn Ser Ile Ser Gly Gln Thr Gly Val
            355                 360                 365

Ser Ser Leu Lys Pro Gly Pro Leu Pro Pro Asn Leu Asp Asp Leu Lys
370                 375                 380

Val Ser Glu Leu Arg Gln Gln Leu Arg Ile Arg Gly Leu Pro Val Ser
385                 390                 395                 400

Gly Thr Lys Thr Ala Leu Val Asp Arg Leu Arg Pro Phe Gln Asp Cys
                405                 410                 415

Ala Gly Asn Pro Val Pro Asn Phe Gly Asp Ile Thr Thr Val Thr Phe
                420                 425                 430

Pro Val Thr Pro Asn Thr Leu Pro Ser Tyr Gln Ser Ser Pro Thr Gly
                435                 440                 445

Phe Tyr His Phe Gly Ser Thr Ser Ser Ser Pro Pro Ile Ser Pro Ala
    450                 455                 460

Ser Ser Asp Leu Ser Ala Ala Gly Ser Leu Pro Asp Thr Phe Thr Asp
465                 470                 475                 480

Ala Ser Pro Gly Phe Gly Leu His Ala Ser Pro Val Pro Ala Cys Thr
                485                 490                 495

Asp Glu Ser Leu Leu Ser Ser Leu Asn Gly Gly Ser Gly Pro Ser Glu
            500                 505                 510

Pro Asp Gly Leu Asp Ser Glu Lys Asp Lys Met Leu Val Glu Lys Gln
            515                 520                 525

Lys Val Ile Asn Gln Leu Thr Trp Lys Leu Arg Gln Glu Gln Arg Gln
530                 535                 540
```

-continued

```
Val Glu Glu Leu Arg Met Gln Leu Gln Lys Gln Lys Ser Ser Cys Ser
545                 550                 555                 560

Asp Gln Lys Pro Leu Pro Phe Leu Ala Thr Thr Ile Lys Gln Glu Asp
                565                 570                 575

Val Ser Ser Cys Pro Phe Ala Pro Gln Gln Ala Ser Gly Lys Gly Gln
                580                 585                 590

Gly His Ser Ser Asp Ser Pro Pro Ala Cys Glu Thr Ala Gln Leu
                595                 600                 605

Leu Pro His Cys Val Glu Ser Ser Gly Gln Thr His Val Leu Ser Ser
            610                 615                 620

Thr Phe Leu Ser Pro Gln Cys Ser Pro Gln His Ser Pro Leu Gly Gly
625                 630                 635                 640

Leu Lys Ser Pro Gln His Ile Ser Leu Pro Pro Ser Pro Asn Asn His
                645                 650                 655

Tyr Phe Leu Ala Ser Ser Ser Gly Ala Gln Arg Glu Asn His Gly Val
                660                 665                 670

Ser Ser Pro Ser Ser Ser Gln Gly Cys Ala Gln Met Thr Gly Leu Gln
            675                 680                 685

Ser Ser Asp Lys Val Gly Pro Thr Phe Ser Ile Pro Ser Pro Thr Phe
690                 695                 700

Ser Lys Ser Ser Ser Ala Val Ser Asp Ile Thr Gln Pro Pro Ser Tyr
705                 710                 715                 720

Glu Asp Ala Val Lys Gln Gln Met Thr Arg Ser Gln Gln Met Asp Glu
                725                 730                 735

Leu Leu Asp Val Leu Ile Glu Ser Gly Glu Met Pro Ala Asp Ala Arg
                740                 745                 750

Glu Asp His Ser Cys Leu Gln Lys Ile Pro Lys Ile Pro Gly Ser Ser
                755                 760                 765

Cys Ser Pro Thr Ala Ile Pro Pro Lys Pro Ser Ala Ser Phe Glu Gln
770                 775                 780

Ala Ser Ser Gly Gly Gln Met Ala Phe Asp His Tyr Ala Asn Asp Ser
785                 790                 795                 800

Asp Glu His Leu Glu Val Leu Leu Asn Ser His Ser Pro Ile Gly Lys
                805                 810                 815

Val Ser Asp Val Thr Leu Leu Lys Ile Gly Ser Glu Glu Pro Pro Phe
                820                 825                 830

Asp Ser Ile Met Asp Gly Phe Pro Gly Lys Ala Ala Glu Asp Leu Phe
                835                 840                 845

Ser Ala His Glu Leu Leu Pro Gly Pro Leu Ser Pro Met His Ala Gln
850                 855                 860

Leu Ser Pro Pro Ser Val Asp Ser Ser Gly Leu Gln Leu Ser Phe Thr
865                 870                 875                 880

Glu Ser Pro Trp Glu Thr Met Glu Trp Leu Asp Leu Thr Pro Pro Ser
                885                 890                 895

Ser Thr Pro Gly Phe Ser Asn Leu Thr Ser Ser Gly Pro Ser Ile Phe
                900                 905                 910

Asn Ile Asp Phe Leu Asp Val Thr Asp Leu Asn Leu Asn Ser Pro Met
                915                 920                 925

Asp Leu His Leu Gln Gln Trp
930                 935
```